(12) United States Patent
Pamer et al.

(10) Patent No.: US 11,471,495 B2
(45) Date of Patent: Oct. 18, 2022

(54) **METHODS AND COMPOSITIONS FOR REDUCING *CLOSTRIDIUM DIFFICILE* INFECTION**

(71) Applicant: MEMORIAL SLOAN-KETTERING CANCER CENTER, New York, NY (US)

(72) Inventors: Eric Pamer, Guilford, CT (US); Charlie Buffie, New York, NY (US); Peter McKenney, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/523,414

(22) Filed: Jul. 26, 2019

(65) Prior Publication Data
US 2019/0381113 A1    Dec. 19, 2019

Related U.S. Application Data

(63) Continuation of application No. 15/312,610, filed as application No. PCT/US2015/031627 on May 19, 2015, now abandoned.

(60) Provisional application No. 62/000,308, filed on May 19, 2014.

(51) Int. Cl.
| | |
|---|---|
| *A61K 35/74* | (2015.01) |
| *C12Q 1/26* | (2006.01) |
| *A61K 38/44* | (2006.01) |
| *A61K 45/06* | (2006.01) |
| *C12N 9/00* | (2006.01) |
| *C12N 9/04* | (2006.01) |

(52) U.S. Cl.
CPC ............ *A61K 35/74* (2013.01); *A61K 38/443* (2013.01); *A61K 45/06* (2013.01); *C12N 9/0006* (2013.01); *C12Q 1/26* (2013.01); *C12Y 101/01159* (2013.01)

(58) Field of Classification Search
None
See application file for complete search history.

(56) References Cited

U.S. PATENT DOCUMENTS

| | | |
|---|---|---|
| 7,326,551 B2 | 2/2008 | Maupin-Furlow et al. |
| 2004/0028689 A1* | 2/2004 | Borody .............. A61K 9/5005 424/184.1 |
| 2011/0280847 A1* | 11/2011 | Sorg ................... A61P 1/00 424/93.41 |
| 2014/0199281 A1* | 7/2014 | Henn ................. A23P 10/30 424/93.46 |

FOREIGN PATENT DOCUMENTS

| | | |
|---|---|---|
| WO | WO 2010/0623 69 A2 | 6/2010 |
| WO | WO 2012/142605 A1 | 10/2012 |
| WO | WO 2013/053836 A1 | 4/2013 |
| WO | WO 2013/080561 A1 | 6/2013 |
| WO | WO 2013/171515 A1 | 11/2013 |

OTHER PUBLICATIONS

U.S. Appl. No. 15/312,610 (Abandoned), filed Nov. 18, 2016.
U.S. Appl., No. 15/312,610, filed Jul. 27, 2019 Abandonment.
Abt et al., "Commensal Bacteria Calibrate the Activation Threshold of Innate Antiviral Immunity," Immunity, 37(1):158-170 (2012).
Bakken et al., "Treating Clostridium difficile infection with Fecal Microbiota Transplantation," Clin Gastroenterol Hepatol., 9(12):1044-1049 (2011).
Barrasa et al., "Bile acids in the colon, from healthy to cytotoxic molecules," Toxicology In Vitro 27:964-977 (2013).
Bartlett et al., "Antibiotic-Associated Pseudomembranous Colitis Due To Toxin-Producing Clostridia," N. Engl. J. Med. 298(10):531-534 (1978).
Basler et al., "Tit-for-tat: Type VI secretion system counterattack during bacterial cell-cell interactions," Cell, 152(4):884-894 (2013).
Basler et al., "Type VI secretion requires a dynamic contractile phage tail-like structure," Nature, 483(7388):182-186 (2013).
U.S. Appl. No. 15/312,610, filed May 7, 2019 Advisory Action.
U.S. Appl. No. 15/312,610, filed Apr. 26, 2019 Response after Final Office Action.
U.S. Appl. No. 15/312,610, filed Feb. 26, 2019 Final Office Action.
U.S. Appl. No. 15/312,610, filed Dec. 12, 2018 Response to Non-Final Office Action.
U.S. Appl. No. 15/312,610, filed Jul. 10, 2018 Non-Final Office Action.
U.S. Appl. No. 15/312,610, filed Nov. 13, 2017 Response to Restriction Requirement.
U.S. Appl. No. 15/312,610, filed Sep. 13, 2017 Restriction Requirement.
Bernstein et al., "Bile acids as carcinogens in human gastrointestinal cancers," Mutation Res 589:47-65 (2005).
Brandl et al., "Vancomycin-resistant enterococci exploit antibiotic-induced innate immune deficit,". Nature 455(7214):804-807 (2008).
Britton et al., "Role of the Intestinal Microbiota in Resistance to Colonization by Clostridium difficile," Gastroenterology 146:1547-1553 (2014).
Buffie et al., "Profound Alterations of Intestinal Microbiota following a Single Dose of Clindamycin Results in Sustained Susceptibility to *Clostridium difficile*-Induced Colitis," Infection and Immunity 80:62-73 (2012).

(Continued)

*Primary Examiner* — Oluwatosin A Ogunbiyi
(74) *Attorney, Agent, or Firm* — Baker Botts L.L.P.

(57) ABSTRACT

The present invention relates to methods and compositions for reducing the risk and severity of *C. difficile* infection. It is based, at least in part, on the discovery that a restricted fraction of the gut microbiota, including the bacterium *Clostridium scindens*, contributes substantially to resistance against *C. difficile* infection. Without being bound by any particular theory, it is believed that this is achieved through the biosynthesis of secondary bile acids.

16 Claims, 29 Drawing Sheets

Figure 2A:
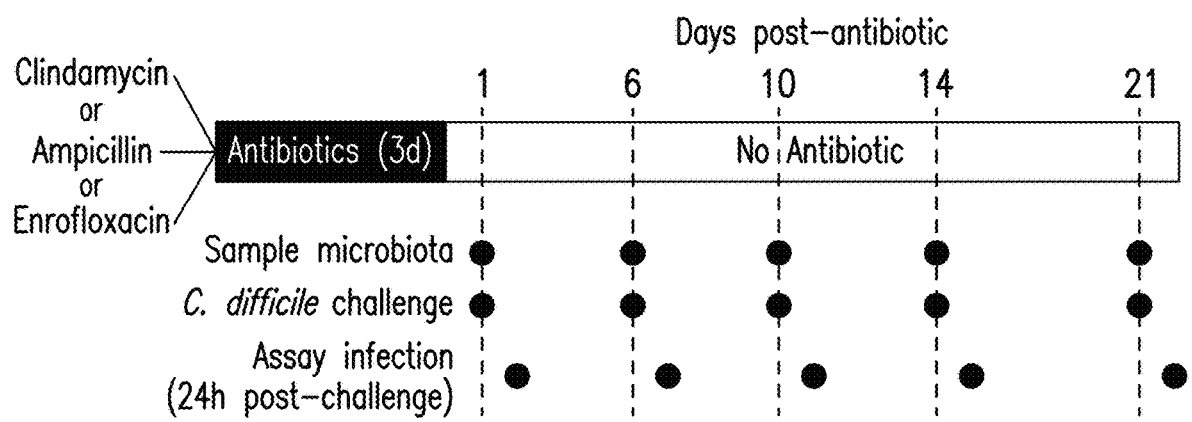

Specification includes a Sequence Listing.

(56) References Cited

OTHER PUBLICATIONS

Buffie et al., "Microbiota-mediated colonization resistance against intestinal pathogens," Nature Reviews Immunology 13(11):790-801 (2013).
Buffie et al., "Precision microbiome reconstitution restores bile acid mediated resistance to *Clostridium difficile*," Nature 517:205-208 (2015).
Caporaso et al., "QIIME allows analysis of high-throughput community sequencing data," Nat Methods. 7(5):335-336 (2010).
Caporaso et al., "Ultra-high-throughput microbial community analysis on the Illumina HiSeq and MiSeq platforms," The ISME Journal 6:1621-1624 (2012).
Carlier et al., "Proposal to unify *Clostridium orbiscindens* Winter et al. 1991 and *Eubacterium plautii* (Sèguin 1928) Hofstad and Aasjord 1982, with description of *Flavonifractor plautii* gen. nov., comb. nov., and reassignment of *Bacteroides capillosus* to *Pseudoflavonifractor capillosus* gen. nov., comb, nov.," Int J Syst Evol Microbiol 60:585-590 (2010).
Chang et al., "Decreased Diversity of the Fecal Microbiome in Recurrent *Clostridium difficile*-Associated Diarrhea," J Infect Dis 197:435-438 (2008).
Chen et al., "A Mouse Model of *Clostridium difficile*-Associated Disease," Gastroenterology 135:1984-1992 (2008).
Chen et al., "Overview of *Clostridium difficile* infection: implications for China," Gastroenterology Report 1:153-158 (2013).
Chung et al., "Gut Immune Maturation Depends on Colonization with a Host-Specific Microbiota," Cell 149(7):1578-1593 (2012).
Cohen, Statistical Power Analysis for the Behavioral Sciences, Second Edition (Routledge, Hillsdale, NJ, 1988).
Collins et al., "The Phylogeny of the Genus *Clostridium*: Proposal of Five New Genera and Eleven New Species Combinations," Int J Syst Bacteriol 44(4):812-826 (1994).
Cruz et al. Antimicrob. Agents Chemother.Jan. 2000 vol. 44 No. 1 143-149.
De Aguiar Vallim et al., "Pleiotropic Roles of Bile Acids in Metabolism," Cell Metab. 17(5):657-669 (2013).
Dethlefsen et al., "Incomplete recovery and individualized responses of the human distal gut microbiota to repeated antibiotic perturbation," PNAS 108(Suppl. 1):4554-4561 (2011).
Diehl et al., "Microbiota Restricts Trafficking of Bacteria to Mesenteric Lymph Nodes by CX(3)CRI(hi) Cells," Nature 494(7435):116-120 (2013).
Duan et al., "Microbial colonization drives expansion of IL-1 receptor 1 expressing, IL-17 producing gamma/delta T cells," Cell Host Microbe, 7(2):140-150 (2010).
Edgar et al., "UCHIME improves sensitivity and speed of chimera detection," Bioinformatics 27(16):2194-2200 (2011).
Farache et al., "Luminal Bacteria Recruit CD103(+) Dendritic Cells into the Intestinal Epithelium to Sample Bacterial Antigens for Presentation," Immunity, 38(3):581-595 (2013).
Ferreira et al., "The Intestinal Microbiota Plays a Role in *Salmonella*-Induced Colitis Independent of Pathogen Colonization," PLoS One 6(5):e20338 (2011).
Giel et al., "Metabolism of Bile Salts in Mice Influences Spore Germination in Clostridium difficile," PLoS ONE, 5(1):e8740 (2010).
"Gut" definition. Merriam Webster Dictionary. https://www.merriam-webster.com/dictionary/gut retrieved Feb. 20, 2019.
Hall, "Building Phylogenetic Trees from Molecular Data with MEGA," Mol. Biol. Evol. 30(5):1229-1235 (2013).
Hamilton et al., "High-throughput DNA sequence analysis reveals stable engraftment of gut microbiota following transplantation of previously frozen fecal bacteria," Gut Microbes 4(2):125-135 (2013).
Hand et al., "Acute Gastrointestinal Infection Induces Long-Lived Microbiota-Specific T Cell Responses," Science, 337(6101):1553-1556 (2012).
Heeg et al., "Spores of *Clostridium difficile* Clinical Isolates Display a Diverse Germination Response to Bile Salts," PLoS One 7(2):e32381 (2012).
Hill et al., "Commensal bacteria-derived signals regulate basophil hematopoiesis and allergic inflammation," Nat Med., 18(4):538-546 (2012).
Huse et al., "Exploring Microbial Diversity and Taxonomy Using SSU rRNA Hypervariable Tag Sequencing," PLoS Genet 4(11):e1000255 (2008).
International Search Report dated Sep. 8, 2015 in International Application No. PCT/US15/31627.
Ivanov et al., "Induction of intestinal Th17 cells by segmented filamentous bacteria," Cell, 139(3):485-498 (2009).
Kang et al., "*Clostridium scindens* baiCD and baiH genes encode stereo-specific 7α/7β-hydroxy-3-oxo-Δ4-cholenoic acid oxidoreductases," Biochim Biophys Acta 1781(1-2):16-25 (2008).
Kinnebrew et al., "Early *Clostridium difficile* Infection during Allogeneic Hematopoietic Stem Cell Transplantation," PLoS One 9(3):e90158 (2014).
Kitahara et al., "Assignment of *Eubacterium* sp. VPI 12708 and related strains with high bile acid 7α-dehydroxylating activity to *Clostridium scindens* and proposal of *Clostridium hylemonae* sp. nov., isolated from human faeces," Int J Syst Evol Microbial 50:971-978 (2000).
Koeth et al., "Intestinal microbiota metabolism of L-carnitine, a nutrient in red meat, promotes atherosclerosis," Nat Med. 19(5):576-585 (2013).
Krishna et al., "Risk Factors, preemptive therapy, and antiperistaltic agents for *Clostridium difficile* infection in cancer patients," Transplant Infect Dis., 15:493-501 (2013).
Kyne et al., "Health Care Costs and Mortality Associated with Nosocomial Diarrhea Due to *Clostridium difficile*," Clin Infect Dis 34:346-353 (2002).
Langille et al., "Predictive functional profiling of microbial communities using 16S rRNA marker gene sequences," Nat Biotechnol 31(9):814-821 (2013).
Lathrop et al., "Peripheral education of the immune system by colonic commensal microbiota," Nature, 478(7368):250-254 (2012).
Lawley et al., "Targeted Restoration of the Intestinal Microbiota with a Simple, Defined Bacteriotherapy Resolves Relapsing *Clostridium difficile* Disease in Mice," PLoS Pathog 8(10):e1002995 (2012).
Liu et al., "Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces," Int J Syst Evol Microbiol 58:1896-1902 (2008).
Louie et al., "Tolevamer, a Novel Nonantibiotic Polymer, Compared with Vancomycin in the Treatment of Mild to Moderately Severe *Clostridium difficile*-Associated Diarrhea," Clin Infect Dis 43:411-420 (2006).
Lozupone et al., "UniFrac: a New Phylogenetic Method for Comparing Microbial Communities," Appl Environ Microbiol 71(12):8228-823 5 (2005).
Macpherson et al., "Induction of Protective IgA by Intestinal Dendritic Cells Carrying Commensal Bacteria," Science, 303:1662-1665 (2004).
Manges et al., "Comparative Metagenomic Study of Alterations to the Intestinal Microbiota and Risk of Nosocomial *Clostridum difficil*-Associated Disease," Journal of Infectious Diseases, 202(12):1877-1884 (2010).
Marcus et al. Gut, 1988, 29, 522-533.
Marsh et al., "Association of Relapse of *Clostridium difficile* Disease with BI/NAP1/027," J Clin Microbial 50(12):4078-4082 (2012).
Olszak et al., "Microbial Exposure During Early Life has Persistent Effects on Natural Killer T Cell Function," Science, 336(6080):489-493 (2012).
Ott et al., "Quantification of Intestinal Bacterial Populations by Real-Time PCR with a Universal Primer Set and Minor Groove Binder Probes: a Global Approach to the Enteric Flora," Journal of Clinical Microbiology, 42(6):2566-2572 (2004).
Out et al., "Bile acid sequestrants: more than simple resins," Curr Opin Lipidol 23:43-55 (2012).

(56) References Cited

OTHER PUBLICATIONS

Pamer, "Fecal microbiota transplantation: effectiveness, complexities, and lingering concerns," Mucosal Immunol 7(2):210-214 (2014).
Partial Supplementary European Search Report dated Jan. 4, 2018 in Application No. 15796000.6.
Petrof et al., "Stool substitute transplant therapy for the eradication of Clostridium difficile infection: 'RePOOPulating' the gut," Microbiome 1:3, pp. 1-12 (2013).
Rakoff-Nahoum et al., "Recognition of Commensal Microflora by Toll-Like Receptors Is Required for Intestinal Homeostasis," Cell, 118:229-241 (2004).
Rasti et al. Journal of Food Agriculture and Environment 11(2):127-131, Apr. 2013.
Rea et al., "Effect of broad- and narrow-spectrum antimicrobials on Clostridium difficile and microbial diversity in a model of the distal colon," PNAS 108(Suppl. 1):4639-4644 (2011).
Rea et al., "Thuricin CD, a posttranslationally modified bacteriocin with a narrow spectrum of activity against *Clostridium difficile*," PNAS, 107(20):9352-9357 (2010).
Reeves et al., "The interplay between microbiome dynamics and pathogen dynamics in a murine model of *Clostridium difficile* infection," Gut Microbes 2(3):145-158 (2011).
Ridlon et al., "Bile salt biotransformations by human intestinal bacteria," J Lipid Res 47:241-259 (2006).
Ridlon et al., "*Clostridium scindens*: a human gut microbe with a high potential to convert glucocorticoids into androgens," J. Lipid Res. 54:2437-2449 (2013).
Ridlon et al., "Identification and characterization of two bile-acid coenzyme A transferases from *Clostridium scindens*, a bile acid 7α-dehydroxylating intestinal bacterium," J. Lipid Res. 53:66-76 (2012).
Ridlon, "Enzymology and Molecular Biology of Bile Acid 7alpha- And 7beta-Dehydroxylation By The Intestinal Bacteria Clostridium Scindens And Clostridium Hylemonae," VCU Theses and Dissertations, Paper 736 (2008).
Rupnik et al., "*Clostridium difficile* infection: new developments in epidemiology and pathogenesis," Nat Rev Microbiol 7:526-536 (2009).
Schloss et al., "Introducing mothur: Open-Source, Platform-Independent, Community-Supported Software for Describing and Comparing Microbial Communities," Appl Environ Microbiol 75(23):7537-7541 (2009).
Sheneman et al., "Clearcut: a fast implementation of relaxed neighbor joining," Bioinformatics 22(22):2823-2824 (2006).
Sorg et al., "Bile Salts and Glycine as Cogerminants for *Clostridium difficile* Spores," J. Bacteriology 190(7):2505-2512 (2008).
Sorg et al., "Chenodeoxycholate is an Inhibitor of *Clostridium difficile* Spore Germination," J Bacteriol 191(3):1115-1117 (2009).
Stein et al., "Ecological Modeling from Time-Series Inference: Insight into Dynamics and Stability of Intestinal Microbiota," PLoS Comput Biol 9(12):e1003388 (2013).
Surawicz et al., "Treatment of refractory and recurrent *Clostridium difficile* infection," Nat Rev Gastroenterology & Hepatology 8:330-339 (2011).
Taur et al., "Intestinal Domination and the Risk of Bacteremia in Patients Undergoing Allogeneic Hematopoietic Stem Cell Transplantation," Clin Infect Dis 55(7):905-914 (2012).
The Human Microbiome Project Consortium: "Structure, Function and Diversity of the Healthy Human Microbiome," Nature 486(7402):207-214 (2013).
Theriot et al., "Antibiotic-induced shifts in the mouse gut microbiome and metabolome increase susceptibility to *Clostridium difficile* infection," Nature Communications 5:3114 pp. 1-22 (2014).
Turnbaugh et al., "A core gut microbiome in obese and lean twins," Nature 457(7228):480-484 (2009).
Ubeda et al., "Intestinal Microbiota Containing *Barnesiella* Species Cures Vancomycin-Resistant *Enterococcus faecium* Colonization," Infection and Immunity 81(3):965-973 (2013).
Ubeda et al., "Vancomycin-resistant *Enterococcus* domination of intestinal microbiota is enabled by antibiotic treatment in mice and precedes bloodstream invasion in humans," J Clin Invest 120(12):4332-4341 (2010).
Van Nood et al., "Duodenal Infusion of Donor Feces for Recurrent *Clostridium difficile*," N Engl. J Med 368(5):407-415 (2013).
Vogt et al. Anaerobe 34 (2015)106-115.
Weingarden et al., "Microbiota transplantation restores normal fecal bile acid composition in recurrent *Clostridium difficile* infection," Am. J Physiol Gastrointest Liver Physiol 306:G310-G319 (2014).
Wells et al., "Development and application of a polymerase chain reaction assay for the detection and enumeration of bile acid 7α-dehydroxylating bacteria in human feces," Clinica Chimica Acta, 331:127-134 (2003).
Wells et al., "Identification and Characterization of a Bile Acid 7α-Dehydroxylation Operon in *Clostridium* sp. Strain TO-931, a Highly Active 7α-Dehydroxylating Strain Isolated from Human Feces," Applied and Environmental Microbiology 66(3):1107-1113 (2000).
Wingender et al., "Intestinal Microbes Affect Phenotypes and Functions of Invariant Natural Killer T Cells in Mice," Gastroenterology, 143(2):418-428 (2012).
Yutin et al., "A genomic update on clostridial phylogeny: Gram-negative spore formers and other misplaced clostridia," Environ Microbiol. 15(10):2631-2641 (2013).
Zar et al., "A Comparison of Vancomycin and Metronidazole for the Treatment of *Clostridium difficile*-Associated Diarrhea, Stratified by Disease Severity," Clin. Infect. Dis. 45:302-307 (2007).
Zhao et al., "RAPSearch2: a fast and memory-efficient protein similarity search tool for next-generation sequencing data," Bioinformatics 28(1):125-126 (2012).
Zilberberg et al., "Increase in Adult *Clostridium difficile*-related Hospitalizations and Case-Fatality Rate, United States, 2000-2005," Emerg Infect Dis 14(6):929-931 (2008).
Atarashi et al., "Treg induction by a rationally selected mixture of Clostridia strains from the human microbiota," Nature, 500:232-236 (2013).

\* cited by examiner

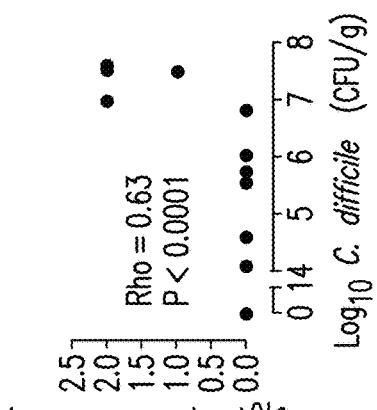
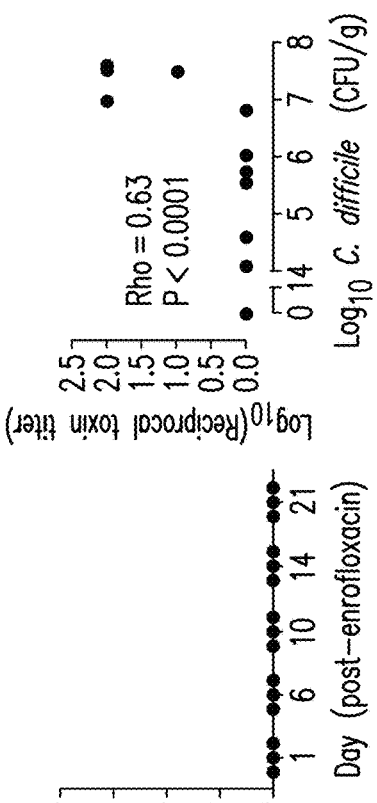
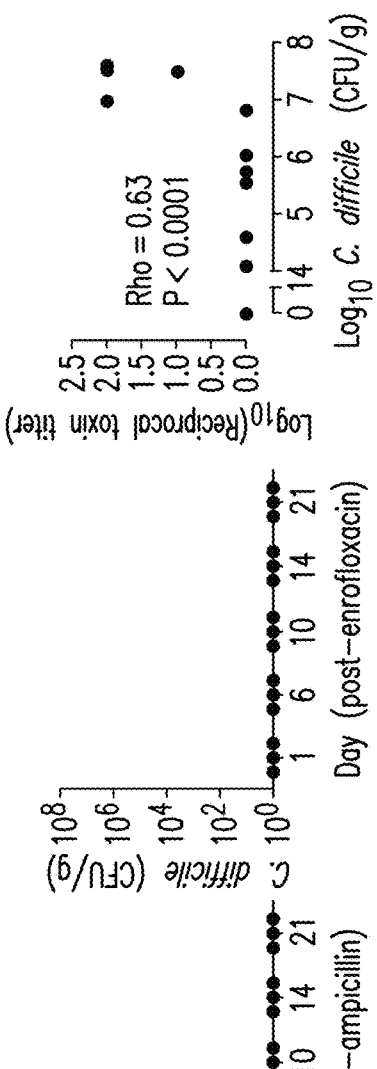
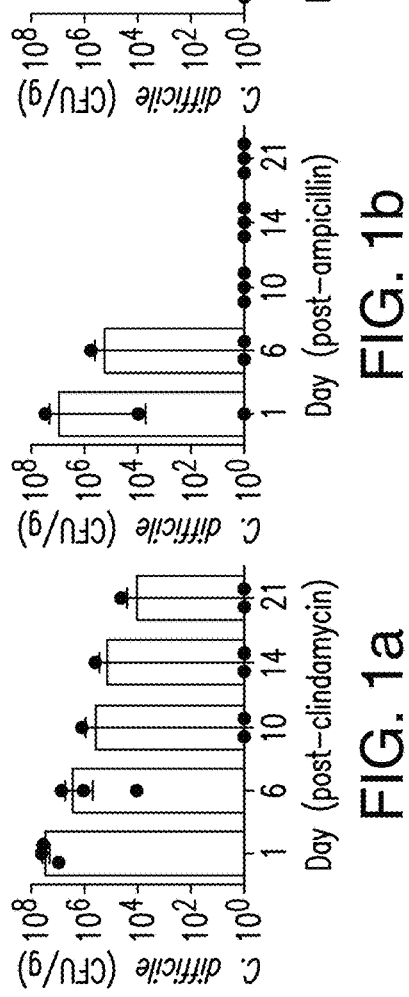
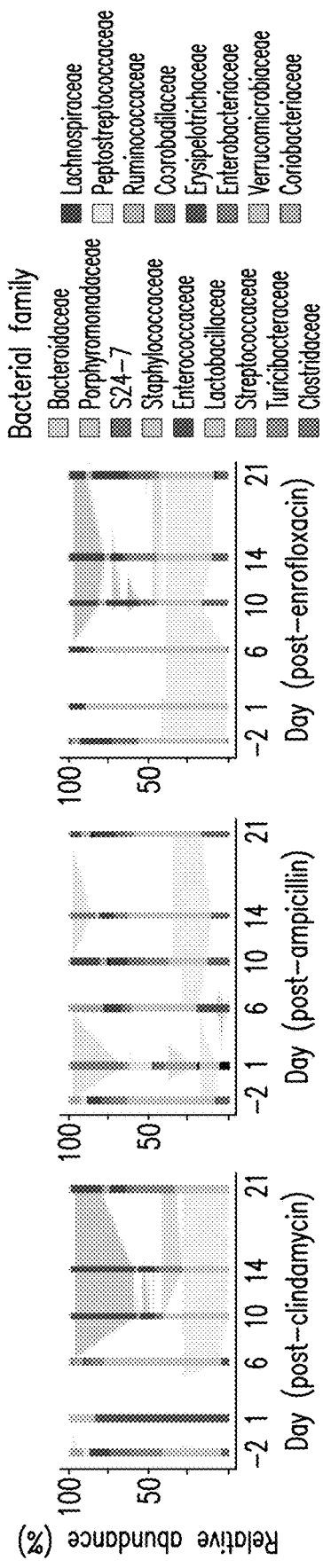

Precise murine microbiota features correlate with *C. difficile* infection resistance Table 1. Characteristics of patients and transplant course.

| Parameter | No. (% of patients) |
|---|---|
| Age (years) | |
| ≤29 | 2/24 (8.3%) |
| 30–39 | 5/24 (20.8%) |
| 40–49 | 2/24 (8.3%) |
| 50–59 | 6/24 (25.0%) |
| ≥60 | 9/24 (37.5%) |
| Sex (female) | 10/24 (41.7%) |
| Underlying Disease | |
| Leukemia | 11/24 (45.8%) |
| Lymphoma | 5/24 (20.8%) |
| Multiple Myeloma | 3/24 (12.5%) |
| Myelodysplastic Syndrome | 3/24 (12.5%) |
| Other | 2/24 (8.3%) |
| Conditioning Intensity | |
| Nonmyeloablative | 4/24 (16.7%) |
| Reduced intensity | 4/24 (16.7%) |
| Myeloablative | 16/24 (66.7%) |
| T-cell depletion | 13/24 (54.2%) |
| Stem cell source (cord vs. other) | 5/24 (20.8%) |
| Time to engraftment (≥14d)[1],[2] | 5/24 (20.8%) |
| Fever (T≥100.4)[2] | 21/24 (87.5%) |
| Vital Status: Dead[2] | 1/24 (4.2%) |
| Total | 24/24 (100.0%) |

[1] Engraftment was defined as an absolute neutrophil count of >500 cells/µL for 3 consecutive days.

[2] Assessed during inpatient allogeneic hematopoietic stem cell trans-plantation hospitalization (from 15 days before transplant to 35 days after transplant).

FIG. 4 Continued

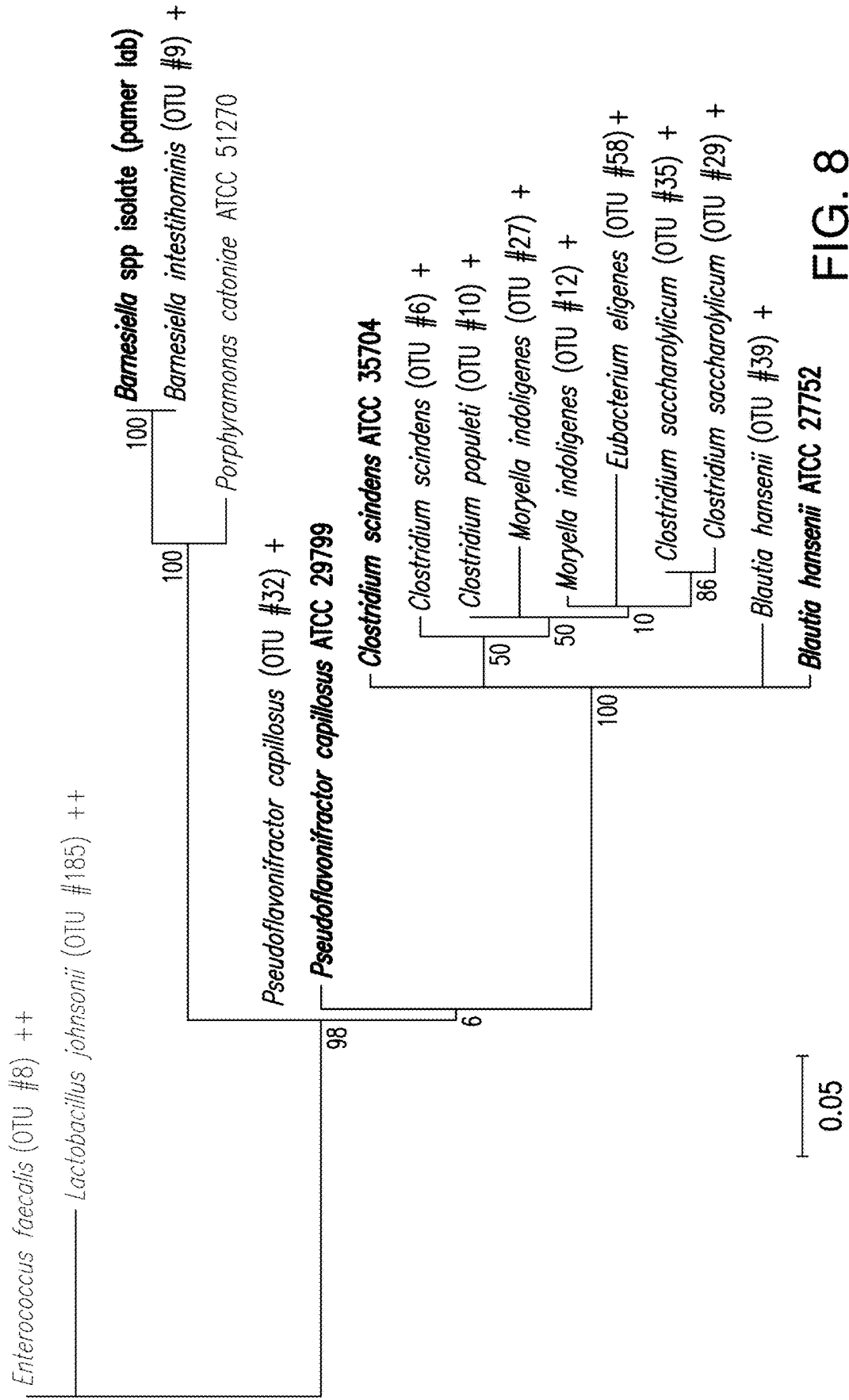

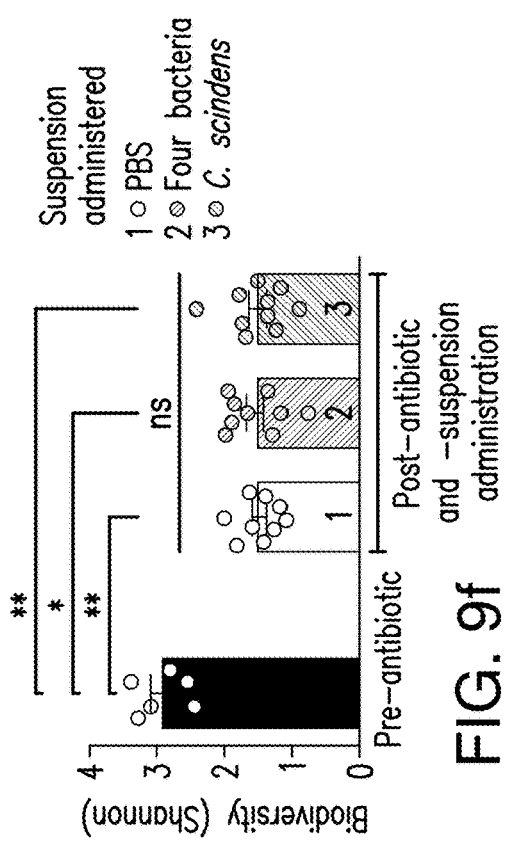
FIG. 9f
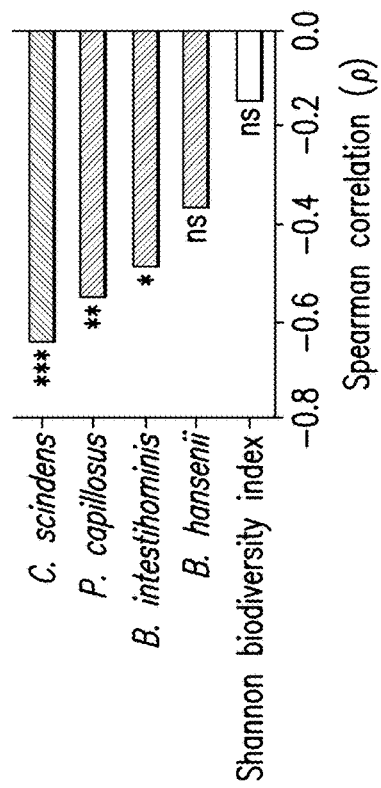
FIG. 9e
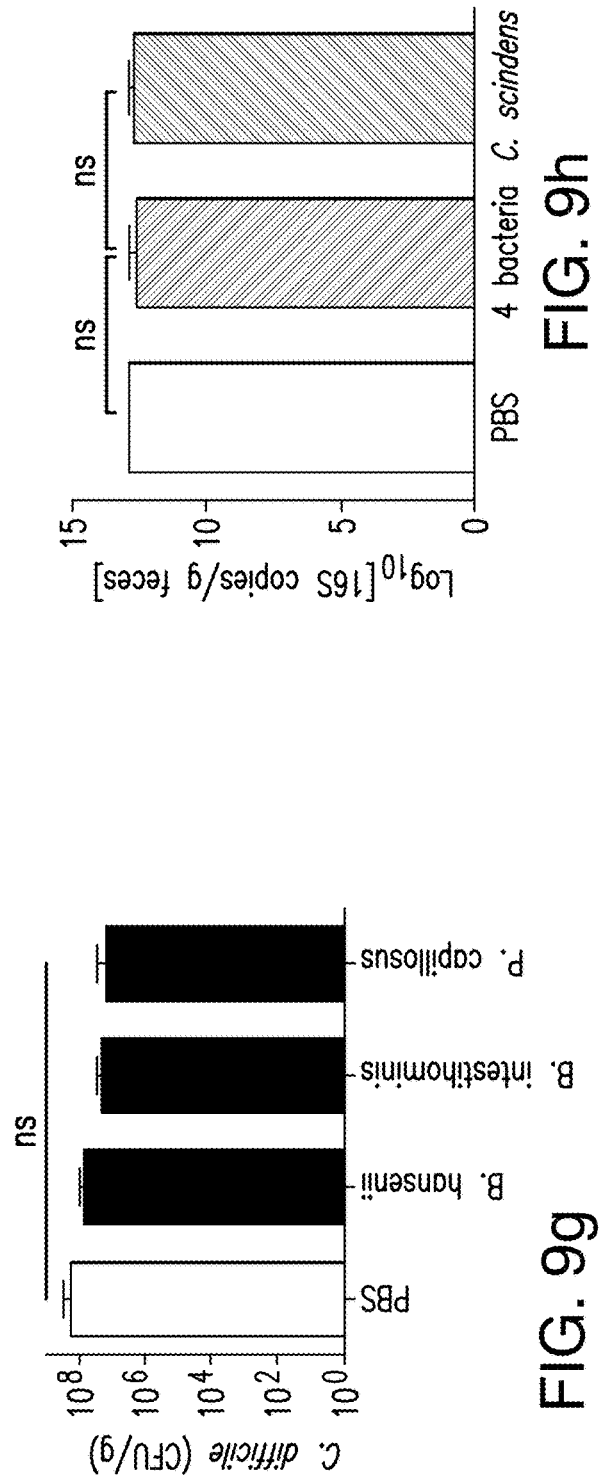
FIG. 9h
FIG. 9g

*C. scindens*-mediated *c. difficile* inhibition is associated with secondary bile acid synthesis and dependent on bile endogenous to intestinal content

Figure 16A:
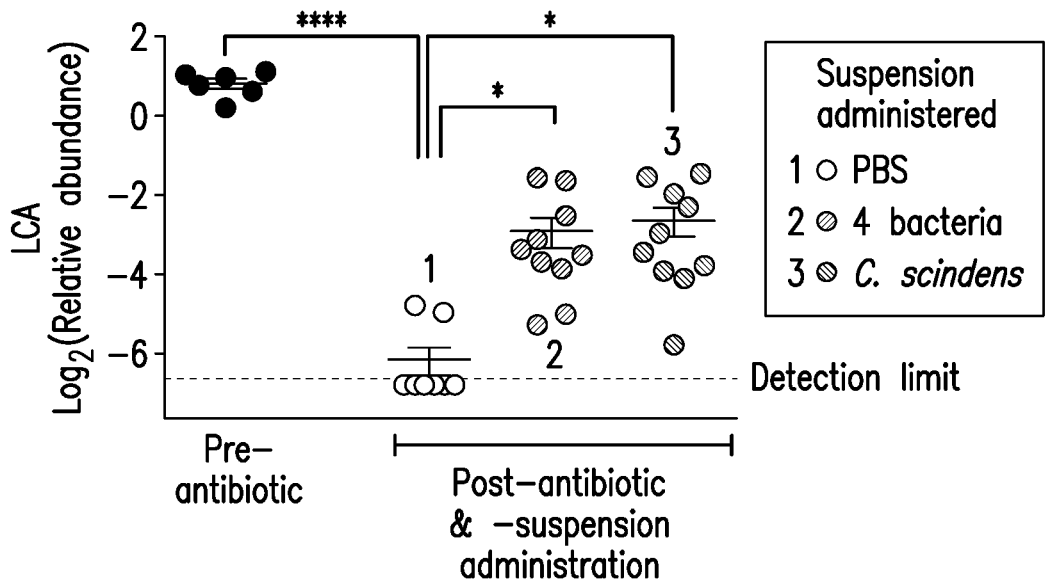
Figure 16B:
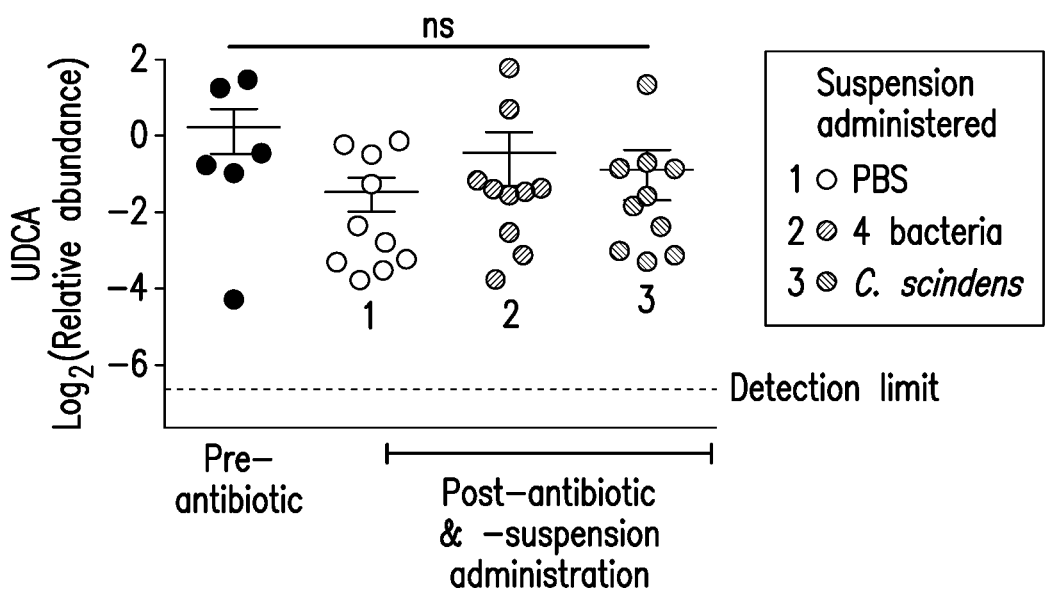

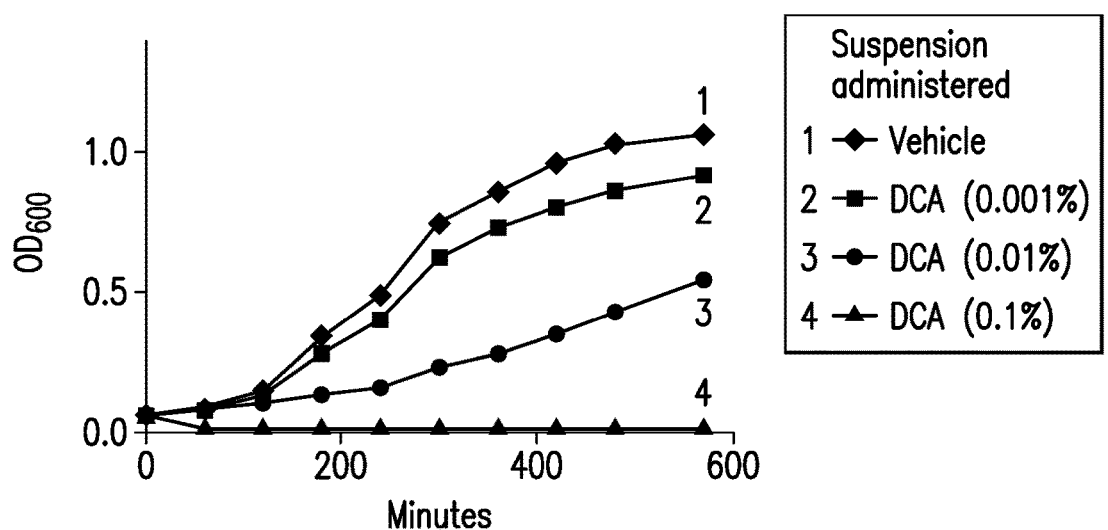
FIG. 16g
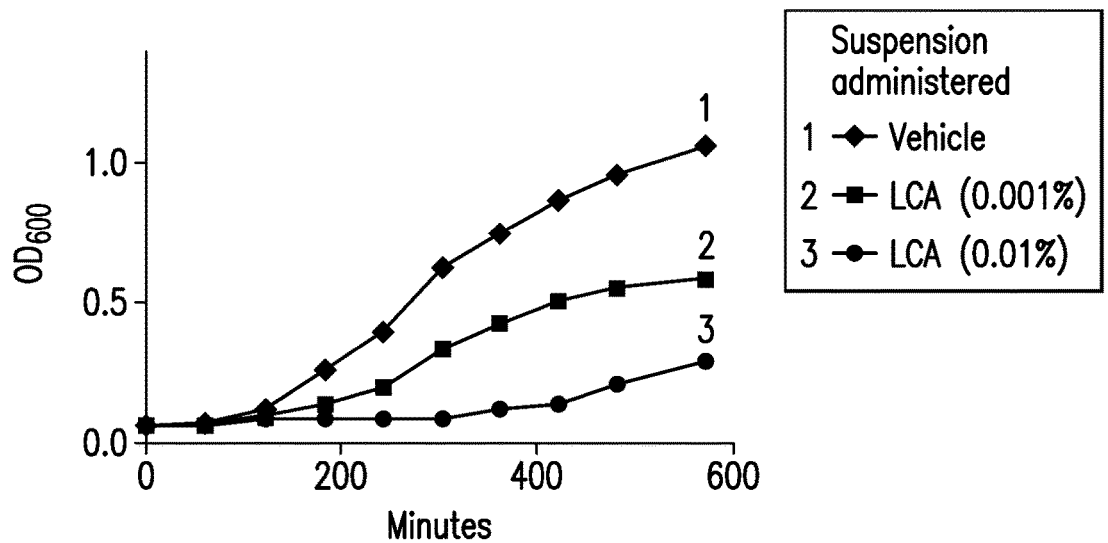
FIG. 16h
Table 2. Retention times for bile acids quantified by HPLC-MS.
| Compound | Molecular formula | Accurate mass | Retention time (min) | CAS number |
|---|---|---|---|---|
| LCA | $C_{24}H_{40}O_3$ | 376.29775 | 24.16 | 434-13-9 |
| UDCA | $C_{24}H_{40}O_4$ | 392.29266 | 16.59 | 128-13-2 |
| DCA | $C_{24}H_{40}O_4$ | 392.29266 | 20.42 | 83-44-3 |
FIG. 16i

```
   1 ggccggaatg cagaagttgt ccctggcgtt tttatgaagg cgaccggcat gagatattga
  61 acgagacaga ccgggaacag gtatatgaag acctgttcca atggattgaa gatcagaaaa
 121 tgacgcagca aaattaggac gctatactta agaaaagtat ccggataatg attacatgaa
 181 tatgaaagat atctggaata ctaaaaataa atcatatgga gggattacac atgaggttaa
 241 aagacaaagt gattctggtt acagcatcca ccagaggcat tggcctggct atcgctcagg
 301 catgtgcgaa agaaggagcc aaagtctaca tgggcgccag gaatctggaa cgcgccaagg
 361 cacgggctga cgagatgaat gcggcaggcg caatgtaaa gtatgtttac aatgatgcga
 421 caaaagaaga gacatacgtg acgatgattg aggaaatcat cgagcaagaa gggcgcatag
 481 acgtgcttgt aaataatttc ggctcatcaa atcccaagaa agatcttgga attgccaata
 541 cagacccgga ggtattcatc aagacggtaa atatcaacct aaagagcgta tttatcgcaa
 601 gccagacggc tgttaagtat atggcggaaa atggaggtgg aagcatcatc aatatctcat
 661 ccgtaggagg cctgatacca gatatctctc agattgccta tggaaccagc aaagcggcaa
 721 tcaactatct gacgaaactg atagccgtac acgaggcaag gcataacatc agatgcaatg
 781 cggtacttcc aggaatgacg gcaacagatg cggtgcagga taatctgacg gatgacttcc
 841 gaaacttctt cttgaagcat acgccaattc agcgtatggg gctcccggaa gagatcgcgg
 901 cagccgtagt atacttcgca agcgatgatg ccgcatatac cacaggacag attcttaccg
 961 tatctggcgg tttcggactg gcaacgccga tatttggaga tctgtctgaa cgctcagatg
1021 cccgcgggta gaatttcatg ggttaactta atcaaaagca gaatcaggaa aagagacagc
1081 cgggagcggc tgtctctttt atctatagtg cgcctagcgg cgcacgtttc taactttata
1141 ggaaagttct cctttcggag aacttgggga ctaaaatagc ccgctcaaaa gcgggcatag
1201 tgaatcagac ggtttggatt aaaagatgta aaagccctct tcaccaaaat cgtcatcatc
1261 aaggttatca aattcatgta agaaataatc catatccaga agttc (SEQ ID NO: 2)
```

FIG. 17

SEQUENCE LISTING

```
<160> NUMBER OF SEQ ID NOS: 2

<210> SEQ ID NO 1
<211> LENGTH: 266
<212> TYPE: PRT
<213> ORGANISM: Clostridium scindens
<220> FEATURE:
<221> NAME/KEY: 7alpha-hydroxysteroid dehydrogenase
<222> LOCATION: (1)..(266)

<400> SEQUENCE: 1

Met Arg Leu Lys Asp Lys Val Ile Leu Val Thr Ala Ser Thr Arg Gly
 1               5                  10                  15
```

Ile Gly Leu Ala Ile Ala Gln Ala Cys Ala Lys Glu Gly Ala Lys Val
            20                  25                  30

Tyr Met Gly Ala Arg Asn Leu Glu Arg Ala Lys Ala Arg Ala Asp Glu
        35                  40                  45

Met Asn Ala Ala Gly Gly Asn Val Lys Tyr Val Tyr Asn Asp Ala Thr
    50                  55                  60

Lys Glu Glu Thr Tyr Val Thr Met Ile Glu Glu Ile Glu Gln Glu
65                  70                  75                  80

Gly Arg Ile Asp Val Leu Val Asn Asn Phe Gly Ser Ser Asn Pro Lys
                85                  90                  95

Lys Asp Leu Gly Ile Ala Asn Thr Asp Pro Glu Val Phe Ile Lys Thr
            100                 105                 110

Val Asn Ile Asn Leu Lys Ser Val Phe Ile Ala Ser Gln Thr Ala Val
        115                 120                 125

Lys Tyr Met Ala Glu Asn Gly Gly Ser Ile Ile Asn Ile Ser Ser
    130                 135                 140

Val Gly Gly Leu Ile Pro Asp Ile Ser Gln Ile Ala Tyr Gly Thr Ser
145                 150                 155                 160

Lys Ala Ala Ile Asn Tyr Leu Thr Lys Leu Ile Ala Val His Glu Ala
                165                 170                 175

Arg His Asn Ile Arg Cys Asn Ala Val Leu Pro Gly Met Thr Ala Thr
            180                 185                 190

Asp Ala Val Gln Asp Asn Leu Thr Asp Asp Phe Arg Asn Phe Phe Leu
        195                 200                 205

Lys His Thr Pro Ile Gln Arg Met Gly Leu Pro Glu Glu Ile Ala Ala
    210                 215                 220

Ala Val Val Tyr Phe Ala Ser Asp Asp Ala Ala Tyr Thr Thr Gly Gln
225                 230                 235                 240

Ile Leu Thr Val Ser Gly Gly Phe Gly Leu Ala Thr Pro Ile Phe Gly
                245                 250                 255

Asp Leu Ser Glu Arg Ser Asp Ala Arg Gly
            260                 265

```
<210> SEQ ID NO 2
<211> LENGTH: 1305
<212> TYPE: DNA
<213> ORGANISM: Clostridium scindens
<220> FEATURE:
<221> NAME/KEY: 7alpha-hydroxysteroid dehydrogenase
<222> LOCATION: (1)..(1305)

<400> SEQUENCE: 2
ggccggaatg cagaagttgt ccctggcgtt tttatgaagg cgaccggcat gagatattga      60
acgagacaga ccgggaacag gtatatgaag acctgttcca atggattgaa gatcagaaaa     120
tgacgcagca aaattaggac gctatactta agaaaagtat ccggataatg attacatgaa     180
tatgaaagat atctggaata ctaaaaataa atcatatgga gggattacac atgaggttaa     240 agacaaagt gattctggtt acagcatcca ccagaggcat tggcctggct atcgctcagg      300
catgtgcgaa agaaggagcc aaagtctaca tgggcgccag gaatctggaa cgcgccaagg     360
cacgggctga cgagatgaat gcggcaggcg gcaatgtaaa gtatgtttac aatgatgcga     420
caaaagaaga gacatacgtg acgatgattg aggaaatcat cgagcaagaa gggcgcatag     480
acgtgcttgt aaataatttc ggctcatcaa atcccaagaa agatcttgga attgccaata     540
cagacccgga ggtattcatc aagacggtaa atatcaacct aaagagcgta tttatcgcaa     600
```

-continued

```
gccagacggc tgttaagtat atggcggaaa atggaggtgg aagcatcatc aatatctcat      660
ccgtaggagg cctgatacca gatatctctc agattgccta tggaaccagc aaagcggcaa      720
tcaactatct gacgaaactg atagccgtac acgaggcaag gcataacatc agatgcaatg      780
cggtacttcc aggaatgacg gcaacagatg cggtgcagga taatctgacg gatgacttcc      840
gaaacttctt cttgaagcat acgccaattc agcgtatggg gctcccggaa gagatcgcgg      900
cagccgtagt atacttcgca agcgatgatg ccgcatatac cacaggacag attcttaccg      960
tatctggcgg tttcggactg gcaacgccga tatttggaga tctgtctgaa cgctcagatg     1020
cccgcgggta gaatttcatg ggttaactta atcaaaagca gaatcaggaa aagagacagc     1080
cgggagcggc tgtctctttt atctatagtg cgcctagcgg cgcacgtttc taactttata     1140
ggaaagttct cctttcggag aacttgggga ctaaaatagc ccgctcaaaa gcgggcatag     1200
tgaatcagac ggtttggatt aaaagatgta aaagccctct tcaccaaaat cgtcatcatc     1260
aaggttatca aattcatgta agaaataatc catatccaga agttc                    1305
```

METHODS AND COMPOSITIONS FOR REDUCING *CLOSTRIDIUM DIFFICILE* INFECTION

CROSS-REFERENCE TO RELATED APPLICATIONS

This application is a continuation of U.S. patent application Ser. No. 15/312,610, filed Nov. 18, 2016, which is a U.S. National Stage Application under 35 U.S.C. § 371 of International Application No. PCT/US15/31627, filed May 19, 2015, which claims priority to U.S. Provisional Application Ser. No. 62/000,308, filed May 19, 2014, the content of each of which is incorporated by reference in its entirety herein, and priority to each of which is claimed.

GRANT INFORMATION

This invention was made with government support under grants AI042135, AI095706 and GM007739 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 26, 2019, is named 0727340917seqlist_ST25.txt and is 4,665 bytes in size.

1. INTRODUCTION

The present invention relates to compositions and methods for decreasing the risk of developing *Clostridium difficile* infection and for treating *Clostridium difficile* infection, should it occur.

2. BACKGROUND OF THE INVENTION

The gastrointestinal tract of mammals is densely colonized by hundreds of microbial species that coexist symbiotically with their hosts. The microbes, collectively referred to as the microbiota, contribute to numerous aspects of host health, including nutrient metabolism (Turnbaugh, Nature 457, 480-484 (2009); Koeth, Nat Med (2013)), homeostasis of intestinal tissues (Rakoff Nahoum, Cell 118, 229-241 (2004)), development of innate and adaptive immune responses (Ivanov, Cell 139, 485-498 (2009); Chung, Cell 149, 1578-1593 (2012); Diehl, Nature 494, 116-120 (2013); Duan, Cell Host Microbe 7, 140-150 (2010); Farache, Immunity 38, 581-595 (2013); Olszak, Science 336, 489-493 (2012); Wingender, Gastroenterology 143, 418-428 (2012); Hand, Science 337, 1553-1556 (2012); Hill, Nat Med 18, 538-546 (2012); Lathrop, Nature 478, 250-254 (2011); Macpherson, Science 303, 1662-1665 (2004)), and more generally, defense against intestinal infection. Bacteria antagonize intestinal pathogens directly, through contact-dependent (Basler, Cell 152, 884-894 (2013); Basler, Nature 483, 182-186 (2012)) and soluble factor-mediated inhibition (Rea, Proc Natl Acad Sci USA 108 Suppl 1, 4639-4644 (2011); Rea, Proc Natl Acad Sci USA 107, 9352-9357 (2010)), as well as indirectly by calibrating and inducing host immune responses (Ivanov, Cell 139, 485-498 (2009); Farache, Immunity 38, 581-595 (2013); Macpherson, Science 303, 1662-1665 (2004); Abt, Immunity 37, 158-170 (2012)), but the contributions of individual bacteria to colonization resistance against specific pathogens are not well understood.

Antibiotic therapies are used for prophylaxis and treatment of a variety of infections with great success in clinical settings, but can eliminate broad swaths of intestinal commensals as collateral damage (Huse, PLoS Genet 4, e1000255 (2008); Dethlefsen, Proc Natl Acad Sci USA 108 Suppl 1, 4554-4561 (2011); Buffie, Infect Immun 80, 62-73 (2012)). Consequently, microbiota-mediated colonization resistance is frequently diminished following antibiotic therapy and may paradoxically enhance susceptibility to a range of life-threatening intestinal pathogens (Brandl, Nature 455, 804-807 (2008); Ubeda, J Clin Invest 120, 4332-4341 (2010); Ferreira, PLoS One 6, e20338 (2011)). *Clostridium difficile* (*C. difficile*) infection is almost universally associated with preceding antibiotic treatment and results in a spectrum of potentially fatal disease (Rupnik, Nat Rev Microbiol 7, 526-536 (2009)), including diarrhea and pseuodomembranous colitis (Bartlett, N. Engl. J. Med. 298:531-534 (1978), as cited in Chen, Gastroenterology Report 1:153-158 (2013)). The incidence, mortality, and costs associated with *C. difficile* infection in the United States and Europe are substantial and increasing (Kyne, Clin Infect Dis 34, 346-353 (2002); Zilberberg, Emerg Infect Dis 14, 929-931 (2008)). Treatment of *C. difficile* infection with vancomycin and metronidazole regimens is frequently successful (Surawicz, Nat Rev Gastroenterol Hepatol 8, 330-339 (2011)), but rates of relapse are high (14-35%) and recurrent infections are often refractory to additional antibiotic therapy (Rupnik, Nat Rev Microbiol 7, 526-536 (2009); Surawicz, Nat Rev Gastroenterol Hepatol 8, 330-339 (2011); Marsh, J Clin Microbiol 50, 4078-4082 (2012)).

The paucity of effective antibiotic treatments, coupled with the prevailing hypothesis that infection susceptibility derives from antibiotic-induced deficits in intestinal microbiota, have prompted numerous independent attempts to treat recurrent *C. difficile* infection by transplanting fecal microbiota obtained from healthy donors. Despite considerable variation among transplantation protocols, reports collected over the past 50 years indicate that fecal microbiota transplantation (FMT) is roughly 90% effective in curing recurrent *C. difficile* infection (Bakken, Clin Gastroenterol Hepatol 9, 1044-1049 (2011)), and a recently completed randomized clinical trial evaluating FMT demonstrated comparably high therapeutic success, superior to standard treatment with vancomycin (VanNood, N Engl J Med 368, 407-415 (2013)). However, since the compositions of fecal transplants are complex, unstandardized, and incompletely defined, concerns about the transmission of undetected pathogens, regulatory complications, and other microbiome-influenced health outcomes (ex. obesity and inflammatory bowel disease) have limited widespread adoption of FMT (Pamer, Mucosal Immunol. 2014 March; 7(2): 210-4). Other attempts to treat *C. difficile* infection have proposed administering secondary bile acids, or at least one strain of bacteria that is capable of metabolizing primary bile salts to secondary bile salts, for example, *Clostridium scindens*, *Clostridium leptum*, and *Clostridium hiranonis* (also known as TO931). (U.S. Publication No. 2011/028847). Massively parallel DNA sequencing technologies have recently facilitated culture-independent characterization of intestinal microbial communities, including those found in microbiota transplants and antibiotic-treated, *C. difficile*-infected hosts (Reeves, Gut Microbes 2, 145-158 (2011); Lawley, PLoS Pathog 8, e1002995 (2012); Petrof, Microbiome 1, 3 (2013); Hamilton, Gut Microbes 4, 125-135

(2013)), but the specific bacteria that are critical for protection against *C. difficile* infection and the mechanisms through which they perform this function have remained largely unknown.

3. SUMMARY OF THE INVENTION

The present invention relates to methods and compositions for reducing the risk and severity of *C. difficile* infection.

In certain non-limiting embodiments, the present invention provides for a recombinant cell expressing a bile acid-inducible (bai) 7α/β-dehydroxylation operon, wherein the recombinant cell comprises one or more exogenous nucleic acids encoding the bile acid-inducible (bai) 7α/β-dehydroxylation operon, wherein the one or more exogenous nucleic acids are operably linked to a promoter. The bile acid-inducible (bai) 7α/β-dehydroxylation operon can include, for example a baiCD gene encoding a 7α-hydroxysteroid dehydrogenase enzyme. The promoter can be an inducible promoter or a constitutively active promoter. The promoter can be a bai operon promoter, or can be another promoter active in the recombinant cell.

The recombinant cell can further comprise one or more nucleic acids encoding a bile salt hydrolase enzyme, antibiotic resistance gene and/or antibiotic susceptibility gene. In certain embodiments, said nucleic acids are comprised in a second recombinant cell that does not include the nucleic acid encoding the bile acid-inducible (bai) 7α/β-dehydroxylation operon.

In certain embodiments, the 7α-hydroxysteroid dehydrogenase is a bacterial 7α-hydroxysteroid dehydrogenase, wherein the bacteria is selected from the group consisting of *Clostridium scindens*, *Clostridium hiranonis*, *Clostridium hylemonae*, *Clostridium perfringens*, *Clostridium sordellii*, *Proteocatella sphenisci*, Lachnospiraceae 5_1_57FAA, Clostridiales VE202-26, Clostridiales VE202-05 and combinations thereof.

In certain non-limiting embodiments, the present invention provides for a composition comprising an isolated *Clostridium scindens* bacterium. In one embodiment, the bacterium is in a formulation for administration to a subject. In other embodiments, the composition further comprising a second bacterium selected from the group consisting of *Barnesiella intestihominis*, *Blautia hansenii*, *Pseudoflavonifractor capillosus* and combinations thereof.

In certain non-limiting embodiments, the present invention provides for a composition comprising one, two, three, or four bacteria, or spores thereof, selected from the group consisting of an isolated *Clostridium scindens* bacterium, an isolated *Barnesiella intestihominis* bacterium, an isolated *Blautia hansenii* bacterium, and an isolated *Pseudoflavonifractor capillosus* bacterium.

In other non-limiting embodiments, the present invention provides for a method for reducing the risk of *C. difficile* infection and/or improving resistance to *C. difficile* infection, as well as for a method for reducing the severity of *C. difficile* infection and/or decreasing the amount of *C. difficile* toxin, comprising administering, to a subject in need of such treatment, an effective amount of a recombinant cell expressing a bile acid-inducible (bai) 7α/β-dehydroxylation operon, or a composition as described herein.

In certain non-limiting embodiments, the present invention provides for a method for reducing the risk of *C. difficile* infection and/or improving resistance to *C. difficile* infection, comprising administering, to a subject in need of such treatment, an effective amount of *Clostridium scindens* (*C. scindens*) bacteria.

In various non-limiting embodiments of the invention, bacteria may be administered in the proliferative state or as spores, or a mixture thereof.

In certain non-limiting embodiments, the present invention provides for a method for reducing the severity of *C. difficile* infection and/or decreasing the amount of *C. difficile* toxin, comprising administering, to a subject in need of such treatment, an effective amount of *C. scindens* bacteria.

In certain non-limiting embodiments, the present invention provides for a method for reducing the risk of *C. difficile* infection and/or improving resistance to *C. difficile* infection, comprising administering, to a subject in need of such treatment, an effective amount of an enzyme that converts a primary bile acid or salt to a secondary bile acid.

In certain non-limiting embodiments, the present invention provides for a method for reducing the severity of *C. difficile* infection and/or decreasing the amount of *C. difficile* toxin, comprising administering, to a subject in need of such treatment, an effective amount of an enzyme that converts a bile salt to a secondary bile acid.

In certain non-limiting embodiments, the present invention provides for a method for reducing the risk of *C. difficile* infection and/or improving resistance to *C. difficile* infection, comprising administering, to a subject in need of such treatment, an effective amount of a secondary bile acid.

In certain non-limiting embodiments, the present invention provides for a method for reducing the severity of *C. difficile* infection and/or decreasing the amount of *C. difficile* toxin, comprising administering, to a subject in need of such treatment, an effective amount of a secondary bile acid.

In one non-limiting embodiment, the present disclosure provides for a method for decreasing the severity of one or more symptoms of an intestinal disorder comprising administering, to a subject in need of such treatment, an effective amount of one or more of a recombinant cell as described herein; a composition comprising *C. scindens* (optionally in combination with one or more other therapeutic bacteria as described herein); and agent selected from the group consisting of an enzyme that converts a bile acid to a secondary bile acid, a secondary bile acid, purified bacteria or spores thereof expressing an enzyme that converts a bile acid to a secondary bile acid, and combinations thereof, wherein the symptoms and/or clinical signs are selected from the group consisting of frequency and/or volume of diarrhea; fever; abdominal cramping, pain, and/or tenderness; elevated level of white blood cells in the blood; loss of serum albumin; weight loss; appearance of pseudomembrane in the intestinal and/or rectal mucosa; and combinations thereof.

The present invention also provides for methods of diagnosing or identifying a subject with a *C. difficile* infection, or at risk for *C. difficile* infection, comprising determining the level one or more bacterium present in the intestinal microbiota sample that can convert a primary bile acid or salt to a secondary bile acid, wherein the subject is diagnosed or identified as having a *C. difficile* infection, or at risk for *C. difficile* infection, when the level or amount of the one or more bacterium present in the intestinal microbiota sample that can convert a primary bile acid or salt to a secondary bile acid is lower than a bacterium reference level. In certain embodiments, the one or more bacterium is selected from the group consisting of *Clostridium scindens*, *Clostridium hiranonis*, *Clostridium hylemonae*, *Clostridium perfringens*, *Clostridium sordellii*, *Proteocatella sphenisci*,

*Lachnospiraceae* 5_1_57FAA, Clostridiales VE202-05, Clostridiales VE202-26, and combinations thereof.

In certain non-limiting embodiments, the method of diagnosing or identifying a subject with a *C. difficile* infection, or at risk for *C. difficile* infection, comprises determining the activity or level of 7α-hydroxysteroid dehydrogenase enzyme present in the intestinal microbiota of a subject, wherein the subject is diagnosed or identified as having a *C. difficile* infection, or at risk for *C. difficile* infection, when the activity or level of 7α-hydroxysteroid dehydrogenase enzyme in the subject's microbiota is lower than a 7α-hydroxysteroid dehydrogenase enzyme reference level.

In certain non-limiting embodiments, the method of diagnosing or identifying a subject with a *C. difficile* infection, or at risk for *C. difficile* infection, comprises quantifying the level of bile acid-inducible (bai) 7α/β-dehydroxylation operon nucleic acid present in the fecal sample of a subject, wherein the subject is diagnosed or identified as having a *C. difficile* infection, or at risk for *C. difficile* infection, when the level of bile acid-inducible (bai) 7α/β-dehydroxylation operon nucleic acid present in the fecal sample is lower than a reference bile acid-inducible (bai) 7α/β-dehydroxylation operon nucleic acid level.

The present invention further provides for kits comprising a recombinant cell expressing a bile acid-inducible (bai) 7α/β-dehydroxylation operon, a *Clostridium scindens* bacteria (and/or any other therapeutic bacteria described herein), an enzyme that converts a primary bile acid or salt to a secondary bile acid, and/or a secondary bile acid.

4. BRIEF DESCRIPTION OF THE FIGURES

FIG. 1A-G. Different antibiotics induce distinct changes to *C. difficile* infection resistance and intestinal microbiota composition.
Susceptibility to *C. difficile* infection following 3-day exposures to clindamycin (a), ampicillin (b), or enrofloxacin (c). Correlation of *C. difficile* colony-forming units (CFU) and *C. difficile* toxin expression in the cecum following challenge (d). Changes in intestinal microbiota composition as measured by fecal sampling prior to *C. difficile* infection challenge at time points indicated (e, f, and g). Each stacked bar represents the mean microbiota composition of three independently-housed animals for a given timepoint and group. ****$P<0.0001$, Spearman (two-tailed) (d). n=3 separately-housed animals per timepoint per group. Center values (mean), error bars (s.e.m.) (a, b, c). Results were representative of two independent experiments.

Figure 2B:
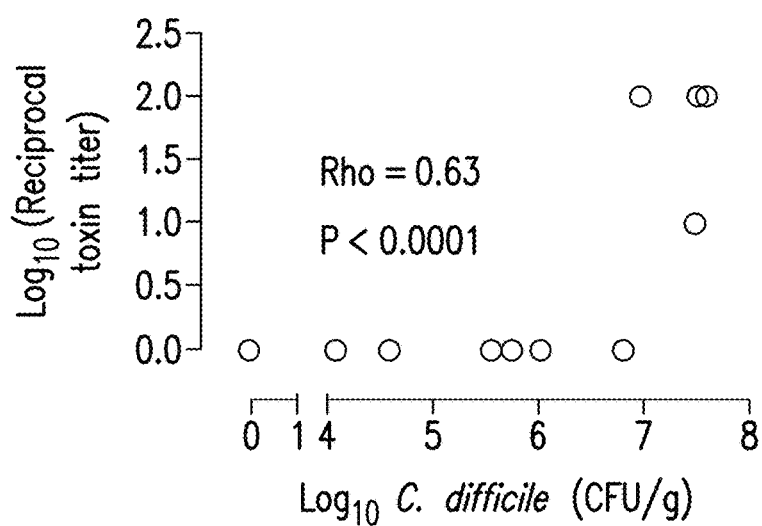
Figure 2C:
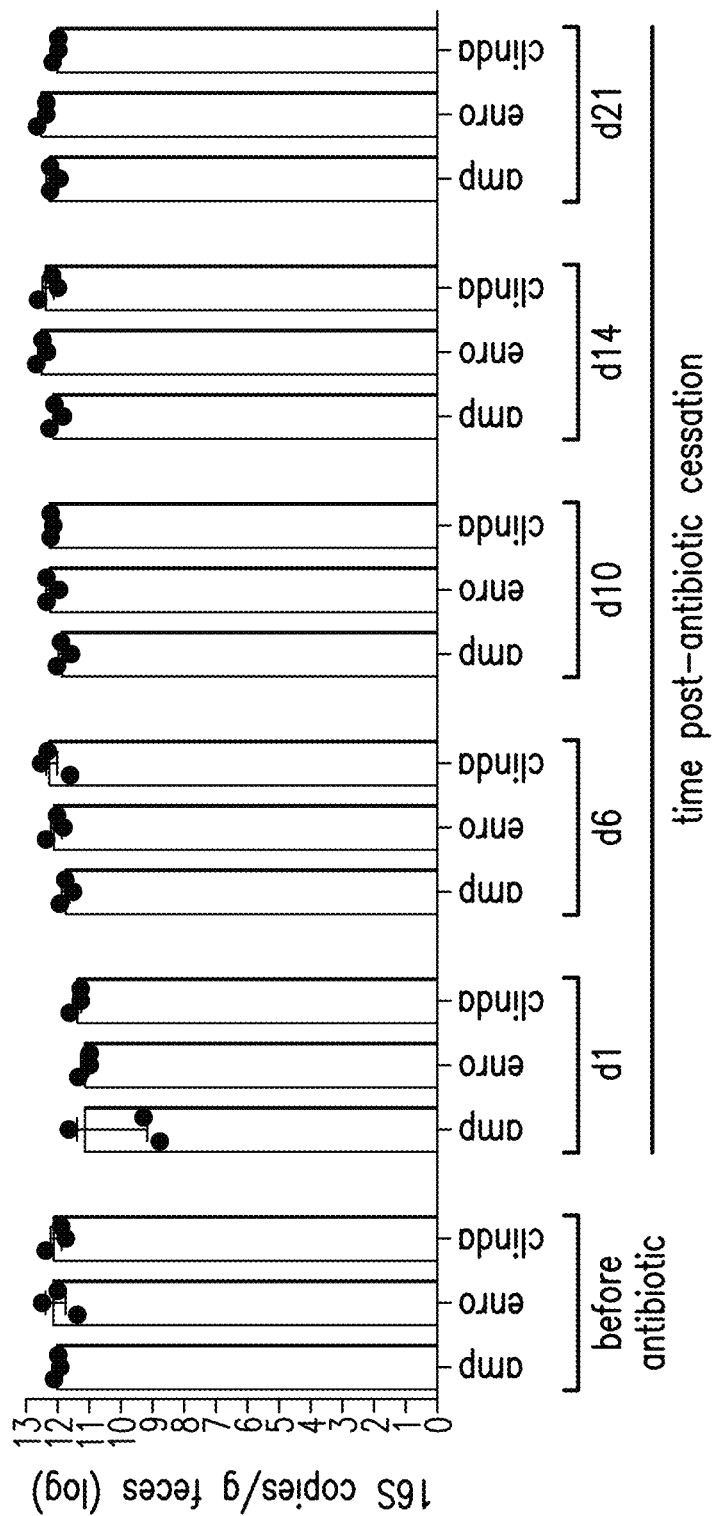

FIG. 2A-C. Stability of bacterial density following antibiotic administration. (a) Strategy for determining *C. difficile* susceptibility duration post-antibiotic exposure (n=3 separately-housed mouse colonies per antibiotic arm) and relating infection resistance to microbiota structure. (b) Correlation of *C. difficile* cfu and toxin in intestinal content following infection. (c) Bacterial density in intestinal content samples (feces) was quantified by quantitative RT-PCR of 16S rRNA genes using degenerate primers obtained at timepoints indicated following three-day exposure to ampicillin (amp), clindamycin (clinda) or enrofloxacin (enro). Results were representative of two independent experiments. Center values (mean), error bars (s.e.m.).

Figure 3A:
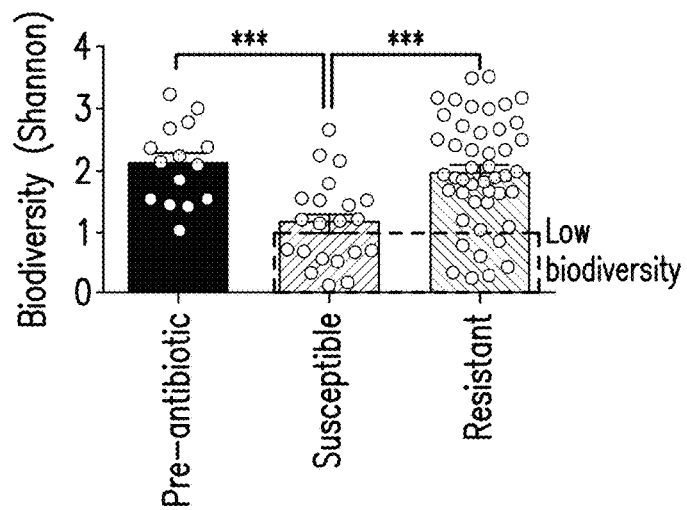
Figure 3B:
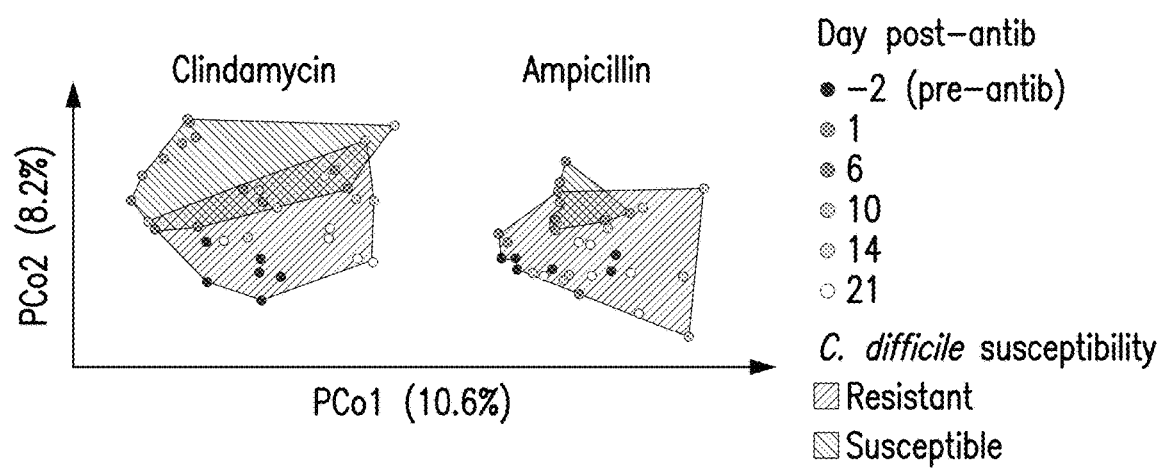
Figure 3C:
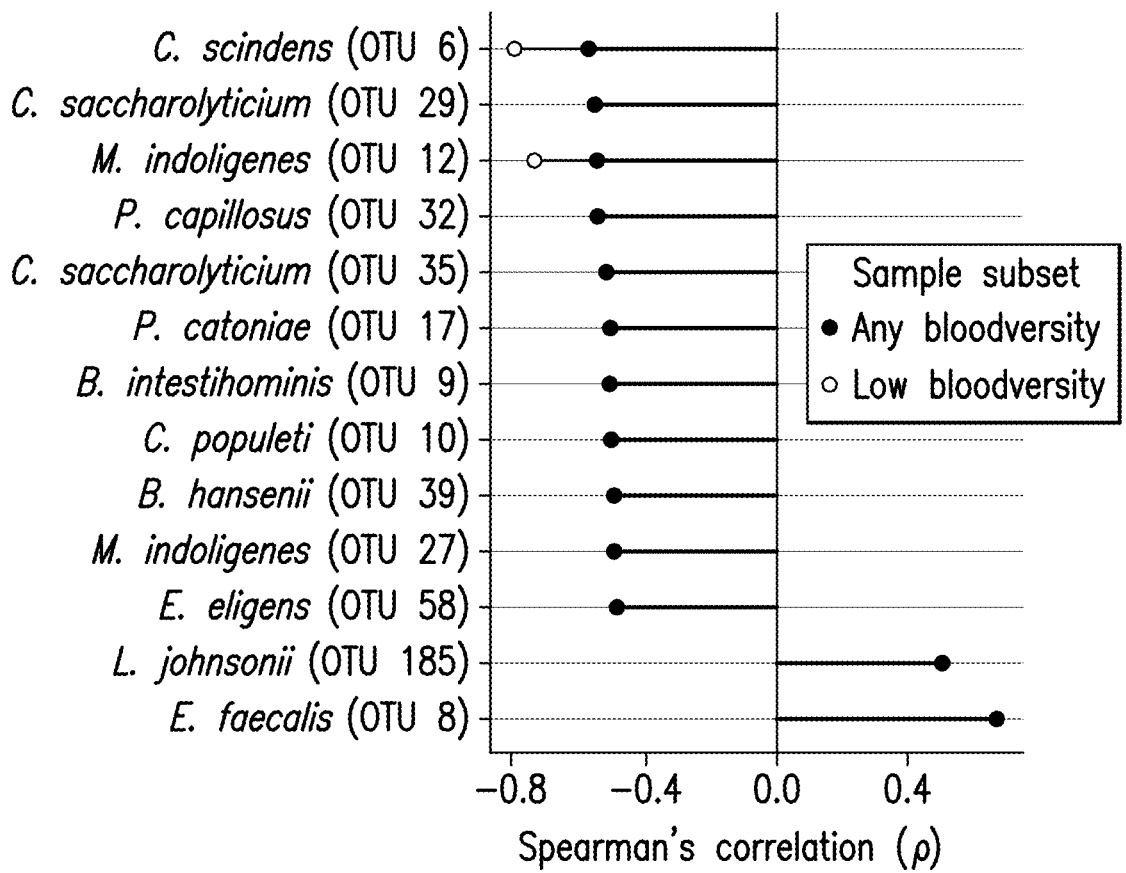

FIG. 3A-C. Precise murine microbiota features correlate with *C. difficile* infection resistance. Intestinal microbiota alpha diversity (Shannon index) (a) and Beta diversity as measured by unweighted UniFrac distances (b) of intestinal microbiota from antibiotic-exposed *C. difficile* susceptible (n=21), resistant (n=47), and pre-antibiotic exposed (n=15) animals. Correlation of individual bacterial OTUs with susceptibility to *C. difficile* infection (c). ***$P<0.001$, Mann-Whitney (two-tailed) (a). In (c), for "Any biodiversity" (n=68 animals, 173 OTUs). $P<0.0005$ for OTUs listed; for "Low biodiversity" (red dashed-line box) where Shannon≤1 (n=16 animals, 61 OTUs), $P<0.05$ for all OTUs listed; Spearman (two-tailed) with Benjamini-Hochberg correction. Center values (mean), error bars (s.e.m.) (a). Results were representative of two independent experiments.

Figure 4:
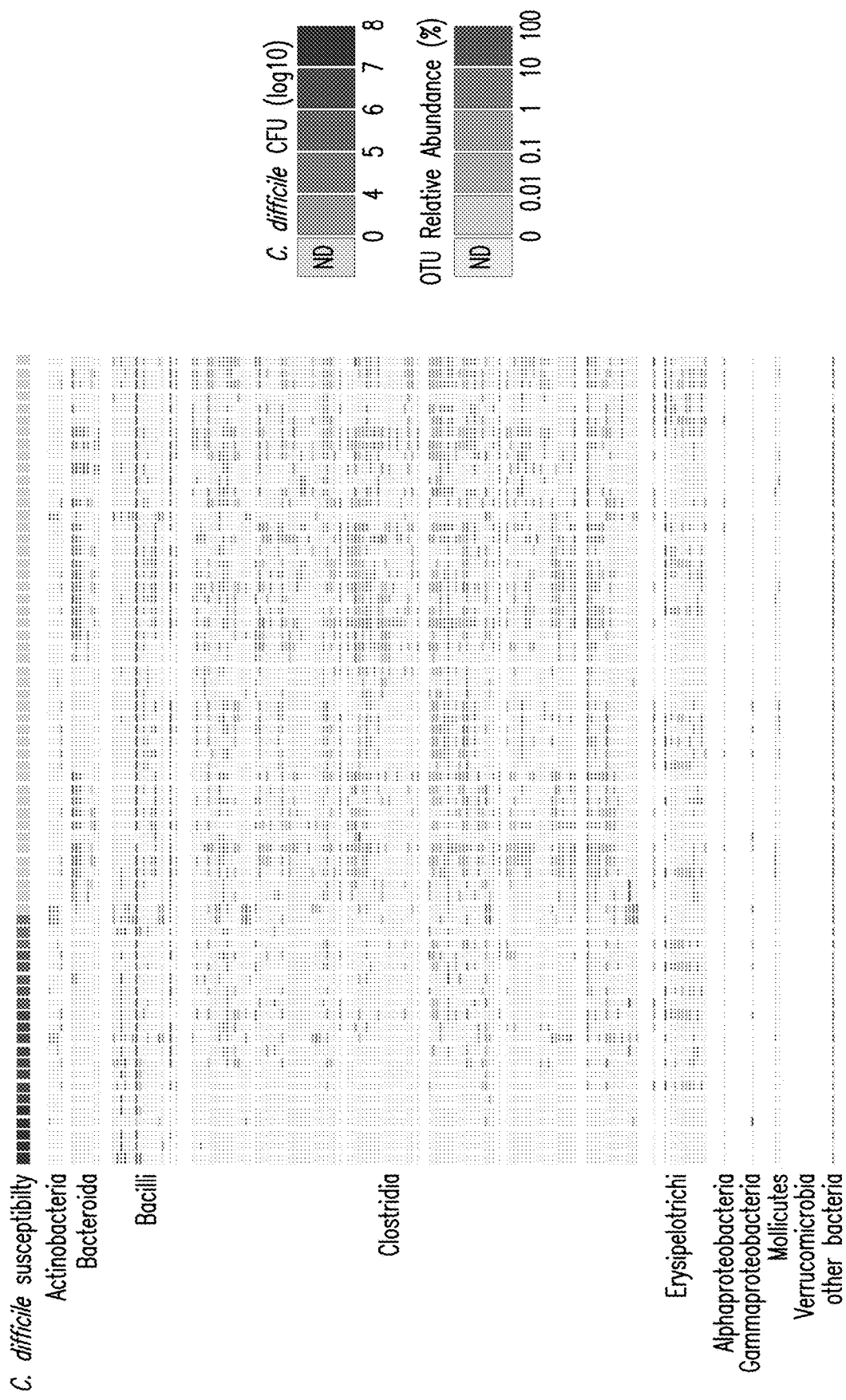

FIG. 4. Correlation of intestinal bacterial species with resistance to *C. difficile* infection. Relative abundance of bacterial OTUs (≥97% sequence identity, >0.01% relative abundance; red), organized by class, among antibiotic-exposed mice (n=68) allowed to recover for variable time intervals prior to *C. difficile* infection challenge with 1,000 spores. Infection susceptibility of animals was evaluated by enumeration of *C. difficile* CFU recovered from the ceca of animals 24-hours post-challenge (blue) by selective, quantitative culture. Results were representative of two independent experiments.

Figure 5A:
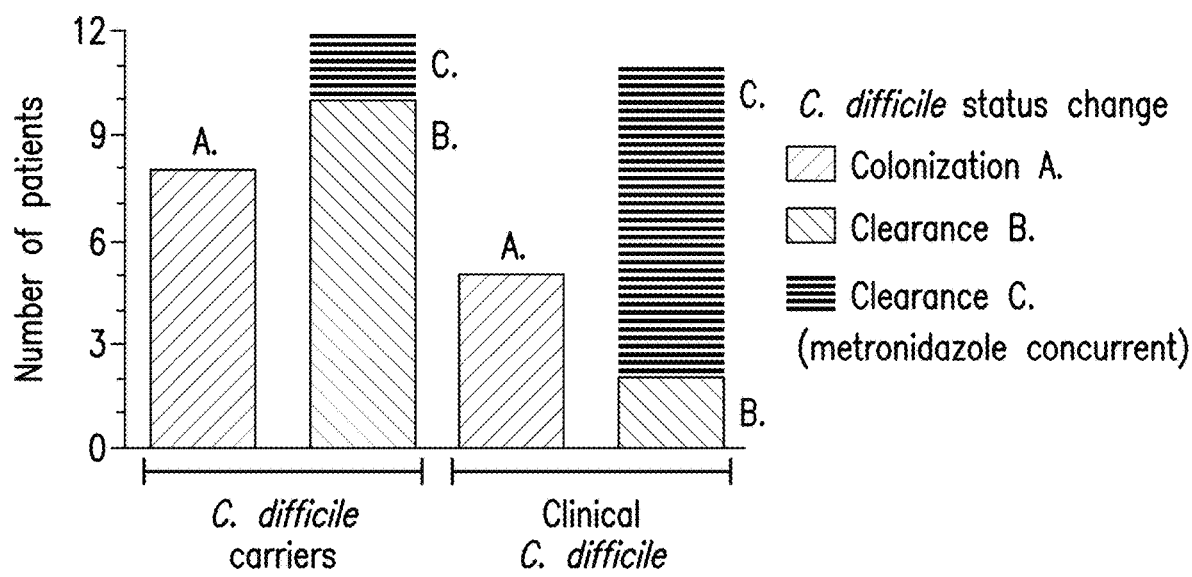
Figure 5B:
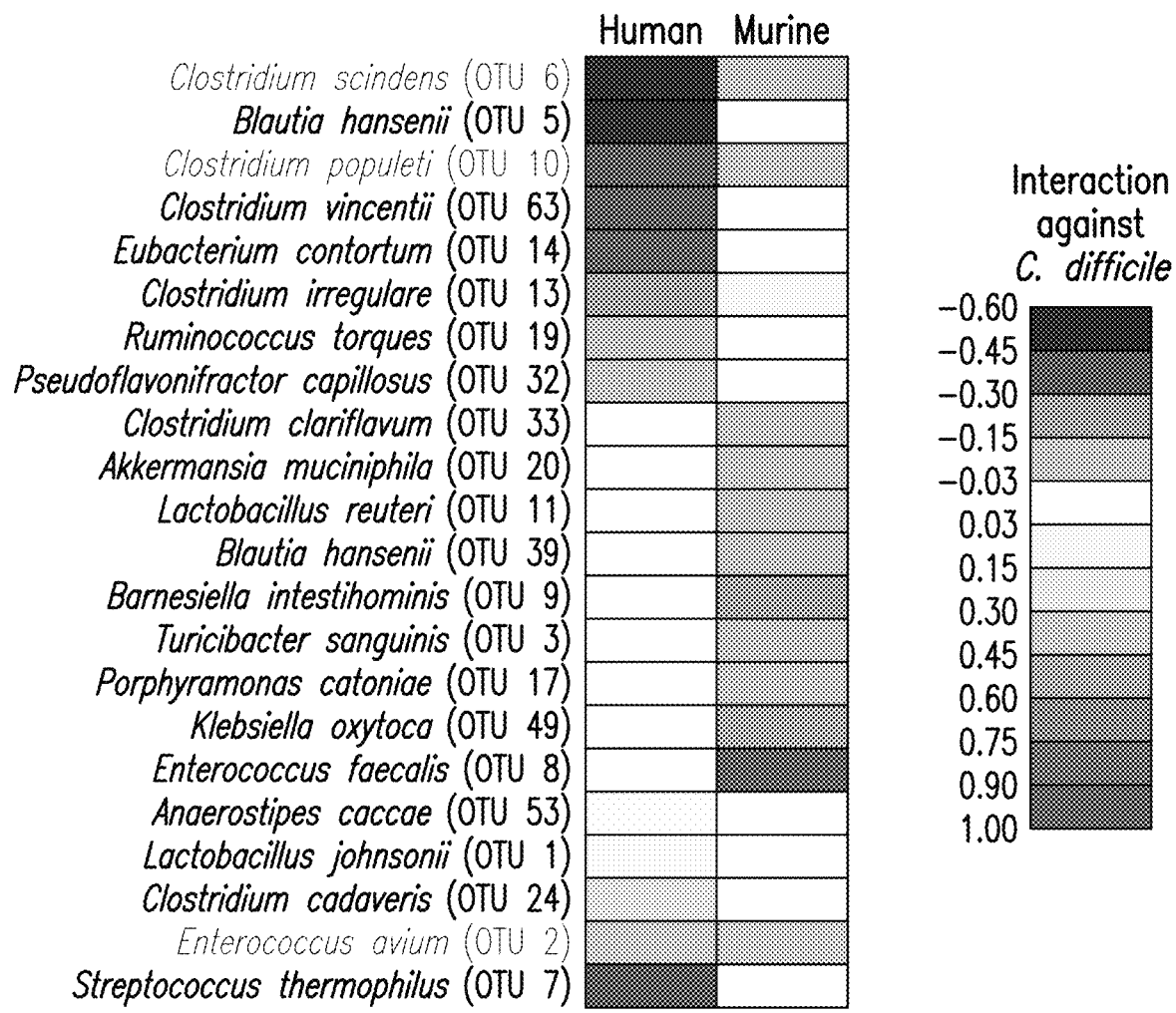
Figure 5C:
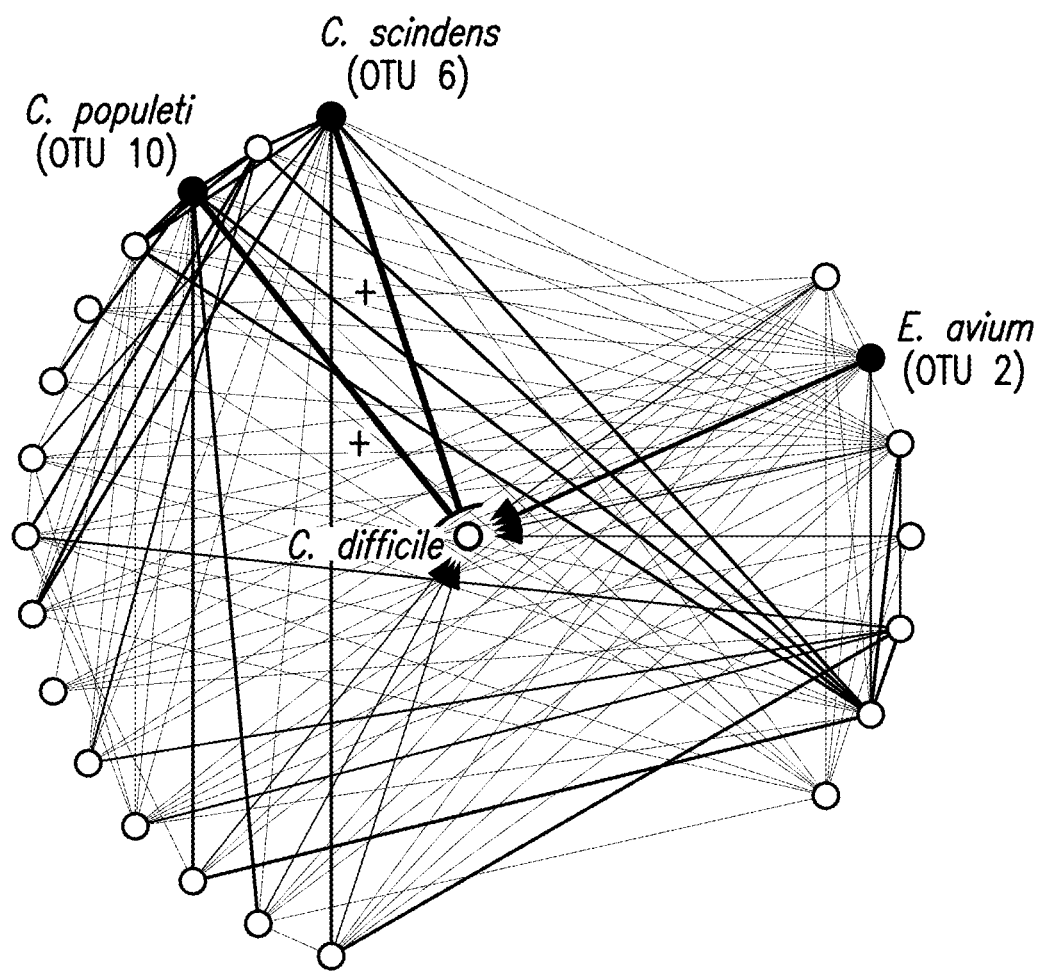

FIG. 5A-C. Native intestinal bacteria that inhibit *C. difficile* are conserved across murine and human microbiota. Quantification of colonization (*C. difficile*-negative to -positive) and clearance (*C. difficile*-positive to -negative) events among *C. difficile*-diagnosed and carrier patients included in the human microbiota interaction inference model (a). A restricted fraction of intestinal bacteria are predicted to strongly interact with *C. difficile* in both the human (n=24 subjects, 112 samples) and murine (n=68 subjects, 240 samples) intestinal microbiota (b). These bacterial OTUs exist in a conserved subnetwork predicted to inhibit (blue, +) or positively associate (red, arrow) with *C. difficile* (c).

Figure 6:
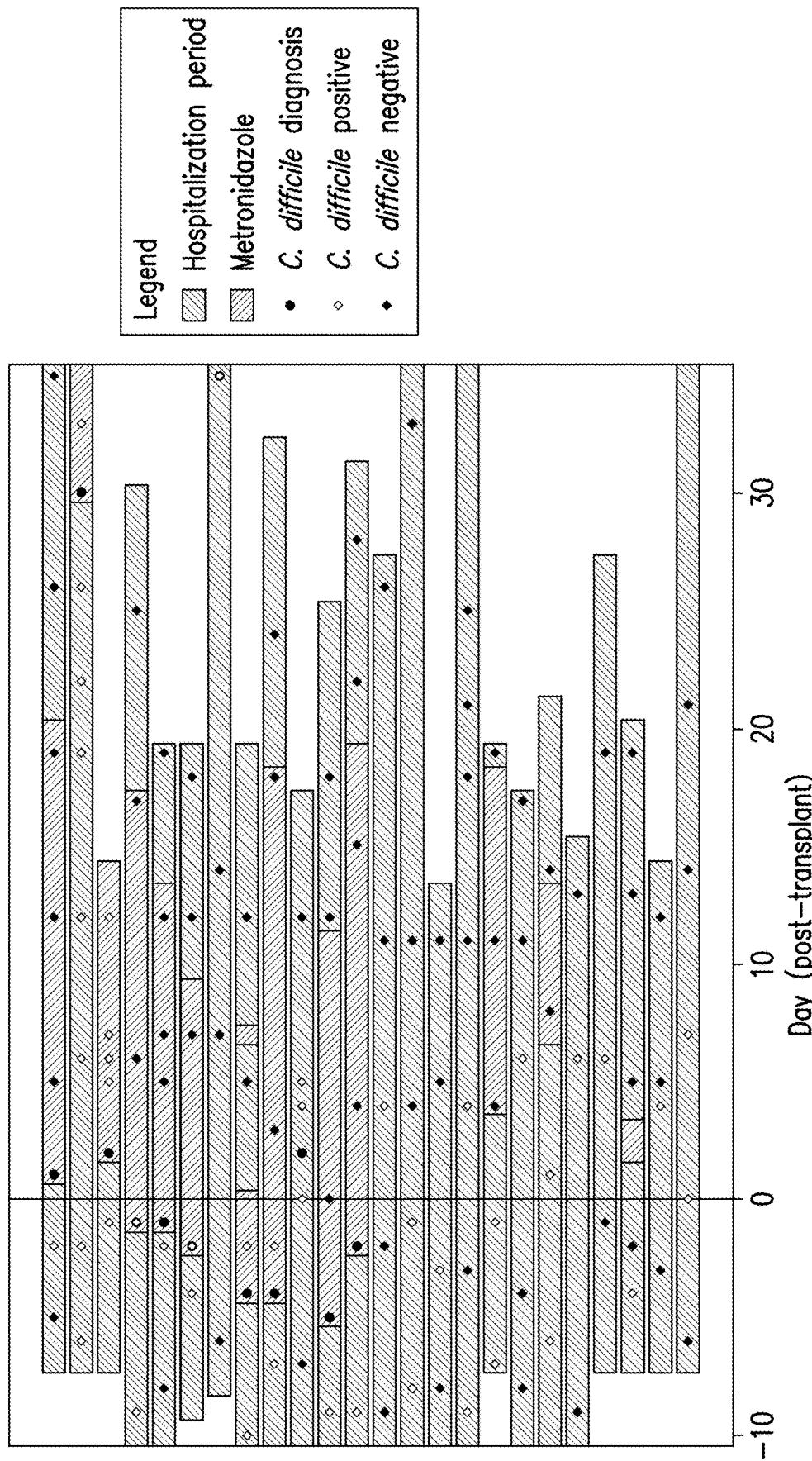

FIG. 6. Allo-HSCT patient timelines and *C. difficile* infection status transitions. Transitions between *C. difficile* (tcdB-positive) colonization status in patients receiving allogeneic hematopoietic stem cell transplantation, as measured by *C. difficile* 16S rRNA abundance during the period of hospitalization (light gray bars). Timepoints when *C. difficile* colonization was determined to be positive (red diamonds) and negative (blue diamonds), and when *C. difficile* infection was clinically diagnosed (black dots) and metronidazole was administered (dark gray bars), are displayed relative to the time of transplant per patient.

FIG. 7A-E. Identification of bacteria conserved across human and murine intestinal microbiota predicted to inhibit *C. difficile*. Identification of bacterial OTUs abundant in mice (n=68) and humans (n=24) (a) that account for a minority of OTU membership (b) but the majority of the structure of the intestinal microbiota of both host species following antibiotic exposure (c). Subnetworks of abundant OTUs predicted inhibit (blue, +) or positively associate with (red, arrow) *C. difficile* in murine (d) and human (e) intestinal microbiota.

FIG. 8. Phylogenetic distribution of resistance-associated intestinal bacteria and isolates selected for adoptive transfer. The maximum likelihood phylogenetic tree (Kimura model, bootstrap of 100 replicates) was constructed using the MEGA 6.06 package from representative sequences of intestinal bacteria associated with resistance to *C. difficile* infection (blue, +), including cultured representatives subsequently used in adoptive transfer experiments (bold). The tree was rooted using intestinal bacteria associated with susceptibility to infection (red, ++) as an out-group.

FIG. 9A-H. Adoptive transfer of resistance-associated intestinal bacteria following antibiotic exposure increases resistance to *C. difficile* infection. Following treatment with antibiotics and a washout period, resistance-associated intestinal bacteria or vehicle were administered to mice and subsequently challenged with 1,000 *C. difficile* spores (n=10 per group). Susceptibility to infection was evaluated by quantification of *C. difficile* CFU (a) and toxin production (b) in mouse feces 24 hours after infection challenge. Weight loss (c) and mortality (d) were monitored for 21 days post-infection challenge. Correlations of adoptively transferred bacteria engrafted with *C. difficile* susceptibility (e), as well as microbiota biodiversity (f) were confirmed using high throughput 16S rRNA sequencing. (g) shows *C. difficile* cfu 24 hours after infection challenge with individual isolates of *B. hansenii*, *B. intestihominis*, and *P. capillosus*, (h) shows intestinal bacterial density in feces from antibiotic-exposed mice administered suspensions containing the four bacteria (*B. hansenii, B. intestihominis, P. capillosus*, and *C. scindens*), *C. scindens* alone, or PBS vehicle as measured by rtPCR of 16S rRNA genes. **P<0.0001, *P<0.001, **P<0.01, *P<0.05, ns (not significant); Mann-Whitney (a, c (day 2, see Extended Data FIG. 8)), Spearman (two-tailed) (b) with Benjamini-Hochberg correction (e), Log-rank test for trend (d), Kruskal-Wallis with Dunn's correction (f). Center values (median (a), mean (f)), error bars (range (a), s.e.m. (f)). Results were representative of at least two independent experiments.

Figure 10:
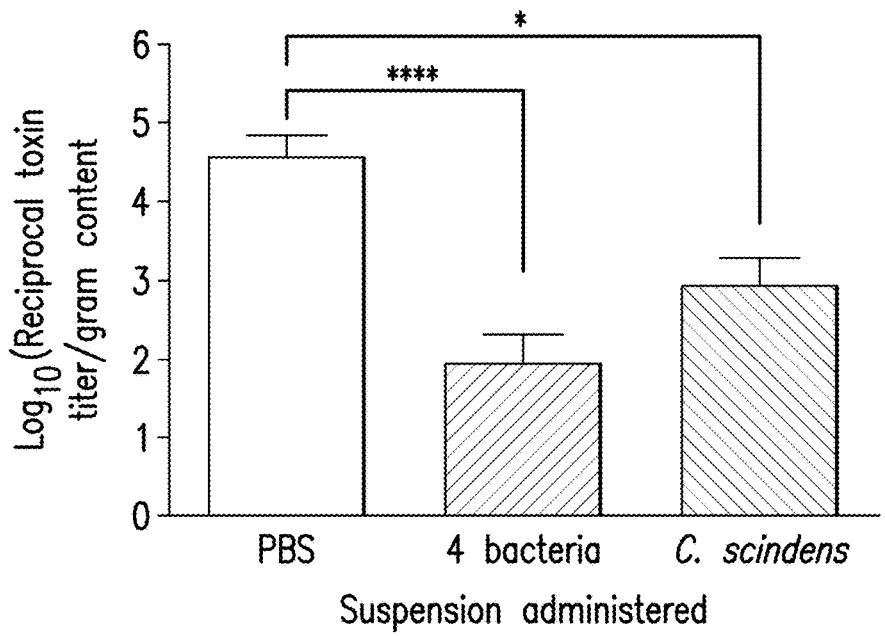

FIG. 10. Adoptive transfer of four-bacteria consortium or *C. scindens* reduces intestinal *C. difficile* cytotoxin load. Antibiotic-exposed mice were administered a suspension containing a 4-bacteria consortium, *C. scindens*, or vehicle (PBS) (n=10 per group) and subsequently challenged with 1,000 *C. difficile* spores. *C. difficile* toxin was quantitated in feces 24 hours after infection challenge using a cell-based assay. **P<0.0001, *P<0.001, **P<0.01, *P<0.05; Mann-Whitney (two-tailed). Center values (mean), error bars (s.e.m.). Results were representative of at least two independent experiments.

Figure 11:
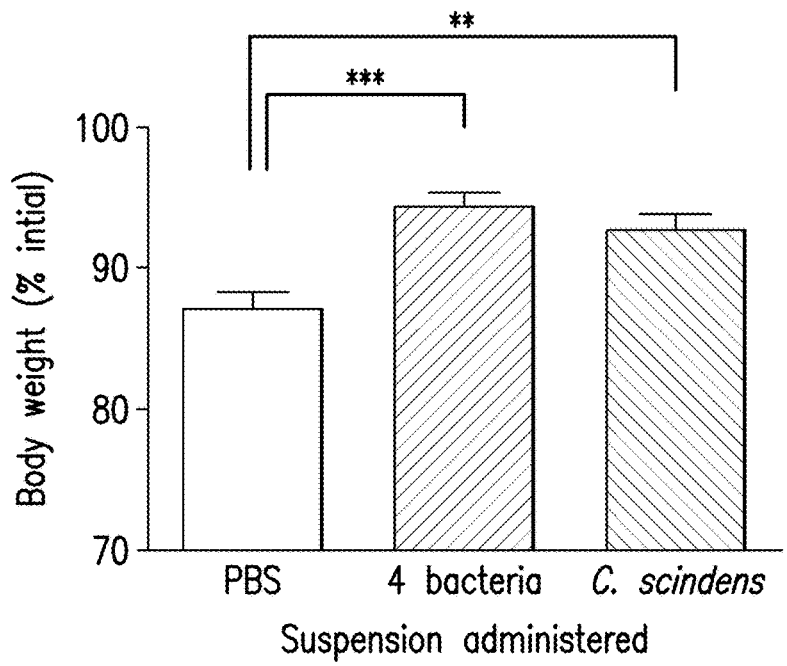

FIG. 11. Adoptive transfer of four-bacteria consortium or *C. scindens* protects mice from acute *C. difficile*-associated weight loss. Antibiotic-exposed mice were administered a suspension containing a 4-bacteria consortium, *C. scindens*, or vehicle (PBS) (n=10 per group) and subsequently challenged with 1,000 *C. difficile* spores. Animals were weighed 48 hours after infection challenge. *P<0.001, P<0.01; Mann-Whitney (two-tailed). Center values (mean), error bars (s.e.m.). Results were representative of at least two independent experiments.

Figure 12:
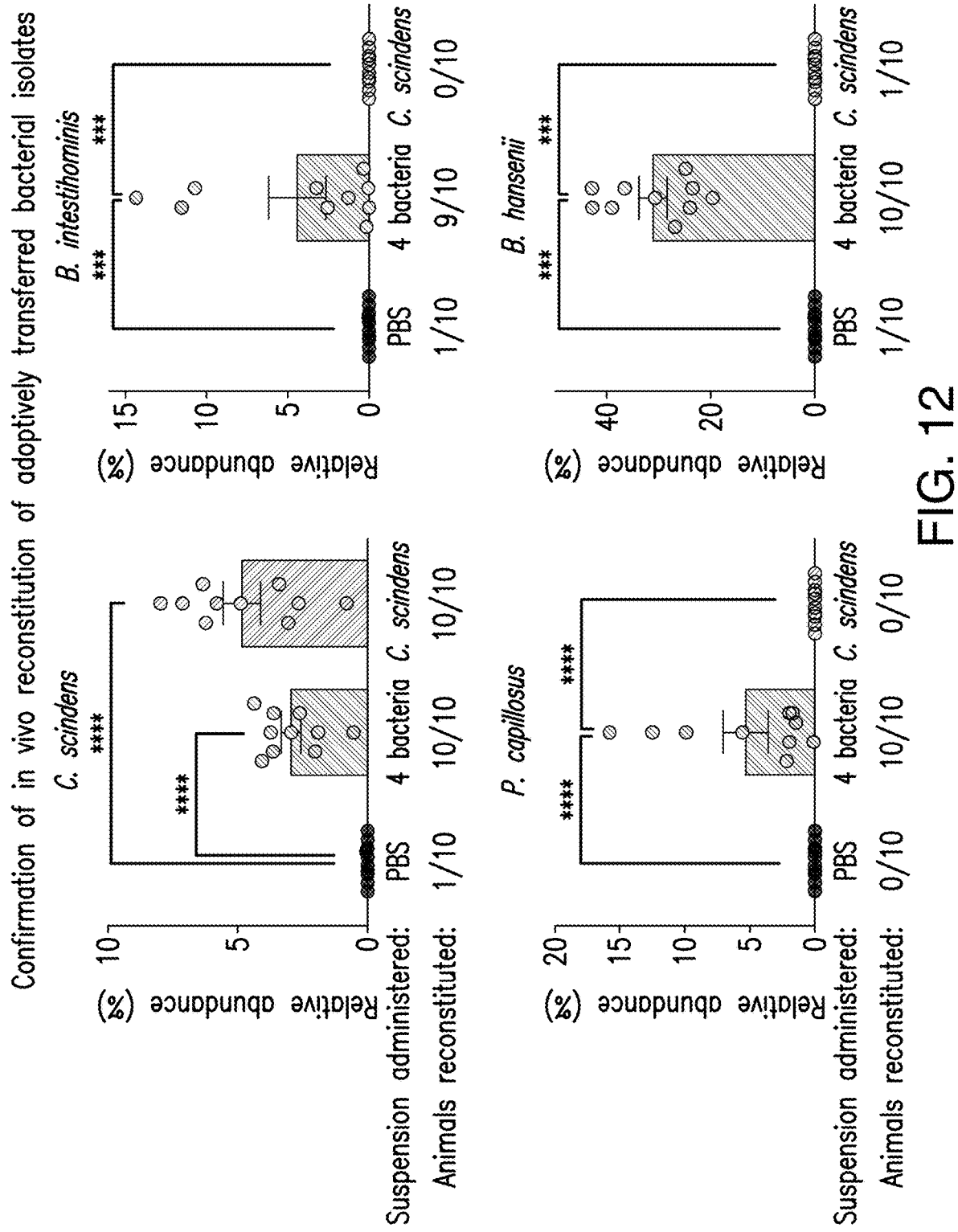

FIG. 12. Confirmation of in vivo reconstitution of adoptively transferred bacterial isolates. Engraftment of bacterial isolates in the intestinal microbiota of antibiotic-exposed animals was confirmed by analysis of high throughput rRNA sequencing of intestinal content (feces) obtained from mice two days following adoptive transfer of *B. intestihominis, P. capillosus, B. hansenii*, and/or *C. scindens*. Numbers under group columns denote the number of mice with detectable engraftment of the given bacterium (out of 10 possible separately-housed animals per group). **P<0.0001, *P<0.001, ns (not significant), Mann-Whitney (two-tailed). Center values (mean), error bars (s.e.m.).

FIG. 13A-H. *C. scindens*-mediated *C. difficile* inhibition is associated with secondary bile acid synthesis and dependent on bile endogenous to intestinal content. Secondary bile acid relative abundance, as measured by enzymatic assay (a), PICRUSt-predicted abundance of secondary bile acid biosynthesis gene family members (b) of intestinal content from antibiotic-exposed *C. difficile* susceptible (n=21), resistant (n=47), and pre-antibiotic (n=15) animals. Correlation of resistance to *C. difficile* infection with abundance of secondary bile acid biosynthesis gene family members in intestinal content samples (n=6) as quantified by shotgun sequencing (gylceroltransferase F51, endogenous reference gene) (c). Restoration of the intestinal abundance of the secondary bile acid deoxycholic acid (DCA) following adoptive transfer of the 4-bacteria consortium or *C. scindens* alone (n=10 per group)(d). Correlation of intestinal relative abundance of *C. scindens*, DCA, and baiCD among antibiotic-exposed, adoptively transferred animals (n=30). Shaded region around mean DCA abundance of 'pre-antibiotic (abx)' represents standard deviation of the mean (solid line)(e). Bile acid-dependent inhibition of *C. difficile* enumerated by recovery of CFU after inoculation of vegetative *C. difficile* into intestinal content from clindamycin-treated animals (n=6 per group) seeded with vehicle (PBS) or *C. scindens* (with or without cholestyramine co-incubation) (f). Bile acid dependent inhibition of *C. difficile* was enumerated by recovery of cfu after inoculation of vegetative *C. difficile* into cell-free (g) or whole (d) intestinal content harvested from C57BL/6J mice (n=5 or 6 per group), with or without pre-incubation with cholestyramine. **P<0.0001, *P<0.001, **P<0.01, *P<0.05; Mann-Whitney (two-tailed) (a,b,f,g,h), Spearman (two-tailed) (c,e), Kruskal-Wallis with Dunn correction (d). Center values (mean), error bars (s.e.m.). Results were representative of at least two independent experiments.

Figure 14:
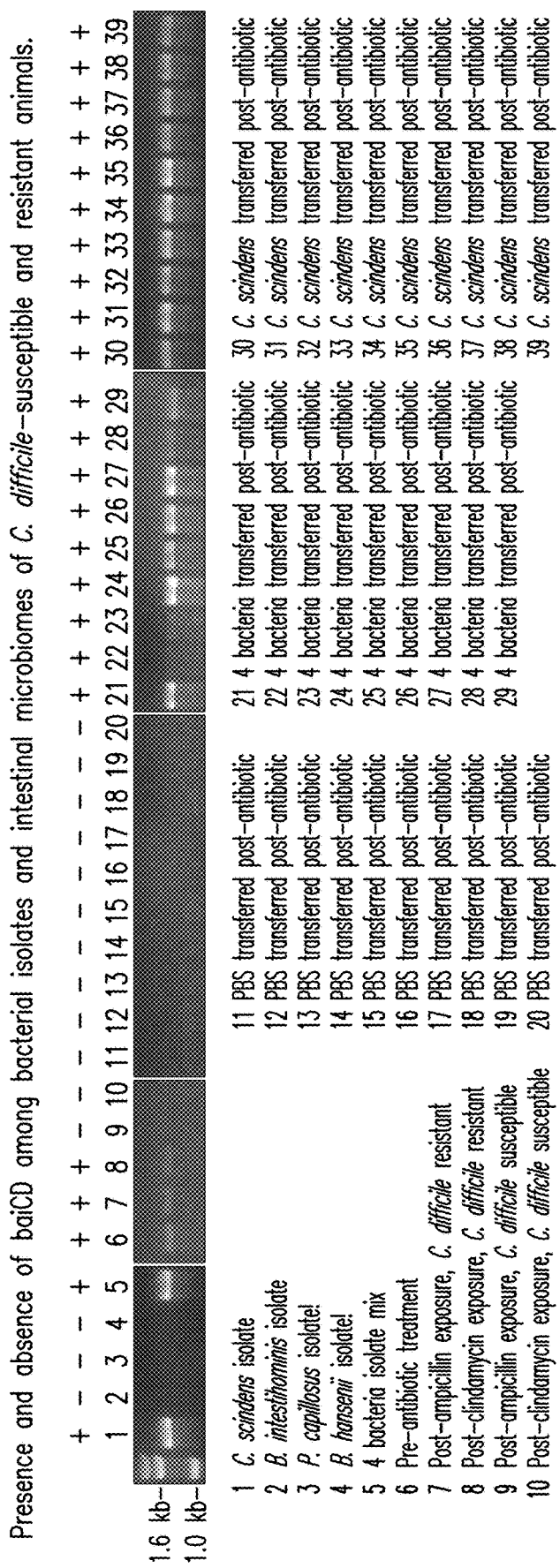

FIG. 14. Presence and absence of baiCD among bacterial isolates and intestinal microbiomes of *C. difficile*-susceptible and resistant animals. PCR-based detection of the 7α-HSDH-encoding baiCD gene in bacterial isolates, intestinal microbiomes (feces) of animals prior to antibiotic exposure, and intestinal microbiomes (feces) of animals that, following antibiotic exposure, remained *C. difficile*-susceptible or recovered resistance to infection spontaneously or following adoptive transfer of bacterial isolates.

Figure 15:
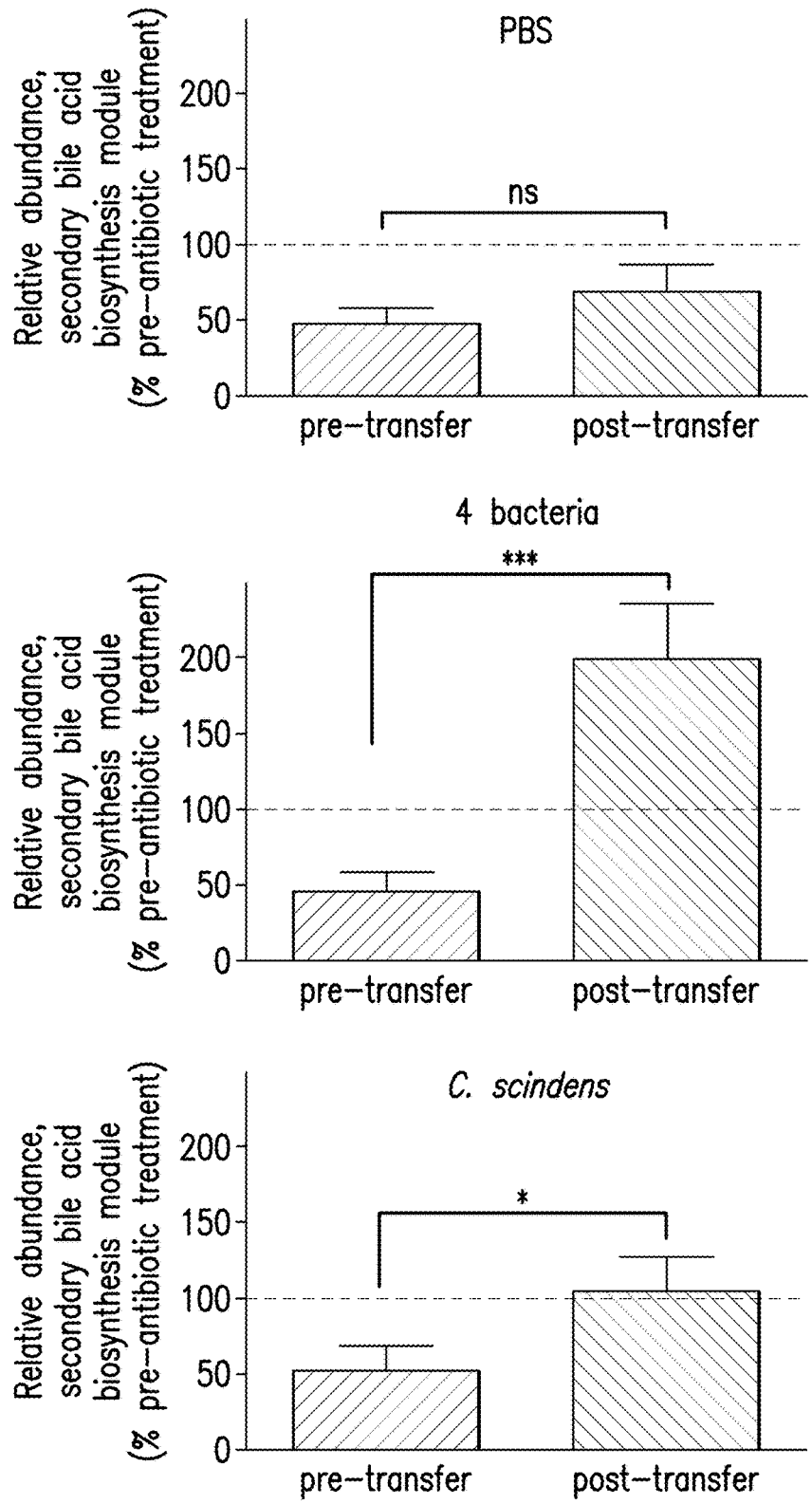

FIG. 15. Adoptive transfer of four-bacteria consortium or *C. scindens* restores secondary bile acid biosynthesis gene family abundance.
Adoptive transfer of the 4-bacteria consortium or *C. scindens* alone reconstitutes abundance of the secondary bile acid biosynthesis gene family in antibiotic-exposed animals (n=10 per group) according to predictive metagenomic functional profiling using PICRUSt. ***P<0.001, *P<0.05, ns (not significant); Mann-Whitney (two-tailed). Center values (mean), error bars (s.e.m.).

FIG. 16A-I. Impacts of bacteria adoptive transfers on intestinal abundance of bile acids. Adoptive transfer of the 4-bacteria consortium or *C. scindens* alone restores abundance of the secondary bile acid lithochoate (LCA) in antibiotic-exposed animals (n=10 per group) compared to unreconstituted antibiotic-exposed animals (a), but does not impact ursodeoxycholate (UDCA) levels (b), taurocholic acid (TCA) levels (c), cholic acid (CA) levels (d), chenodeoxycholic acid (CDCA) levels (e), or tauro-chenodeoxycholic acid (TCDCA) levels (f). (g) and (h) show that the addition of secondary bile acids DCA (g) or LCA (h) to culture media inhibits *C. difficile* growth. (i) shows the retention times for bile acids quantified by HPLC-MS. ****P<0.0001, *P<0.05, ns (not significant), Kruskal-Wallis test with Dunn's correction. Center values (mean), error bars (s.e.m.).

FIG. 17. Nucleic acid sequence of the gene encoding a 7α-hydroxysteroid dehydrogenase enzyme from *C. scindens*.

5. DETAILED DESCRIPTION OF THE INVENTION

The present invention relates to methods and compositions for reducing the risk and/or severity of *C. difficile* infection. For clarity of description, and not by way of limitation, this section is divided into the following subsections:

(i) Recombinant cells;
(ii) Therapeutic bacteria;
(iii) Pharmaceutical compositions;
(iv) Methods of treatment; and
(v) Non-limiting embodiments of the disclosure.

The following are terms relevant to the present invention:

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

An "effective amount" of a substance as that term is used herein is that amount sufficient to effect beneficial or desired results, including clinical results, and, as such, an "effective amount" depends upon the context in which it is being applied. In the context of administering a composition to reduce the risk ofClostridium difficile infection and/or increase resistance to Clostridium difficile infection in a subject, and/or administering a composition to reduce the severity of Clostridium difficile infection and/or decreasing the amount of Clostridium difficile toxin in a subject, an effective amount of a composition described herein is an amount sufficient to treat and/or ameliorate a Clostridium difficile infection, as well as decrease the severity and/or reduce the likelihood of a Clostridium difficile infection. The decrease can be a 10%, 20%, 30%, 40%, 50%, 60%, 70%, 80%, 90%, 95%, 98% or 99% decrease in severity of Clostridium difficile infection, or likelihood of becoming infected. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

The term "expression vector" is used to denote a nucleic acid molecule that is either linear or circular, into which another nucleic acid sequence fragment of appropriate size can be integrated. Such nucleic acid fragment(s) can include additional segments that provide for transcription of a gene encoded by the nucleic acid sequence fragment. The additional segments can include and are not limited to: promoters, transcription terminators, enhancers, internal ribosome entry sites, untranslated regions, polyadenylation signals, selectable markers, origins of replication and such, as known in the art. Expression vectors are often derived from plasmids, cosmids, viral vectors and yeast artificial chromosomes; vectors are often recombinant molecules containing nucleic acid sequences from several sources.

The term "operably linked," when applied to nucleic acid sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

A "nucleic acid molecule" is a single or double stranded covalently-linked sequence of nucleotides in which the 3' and 5' ends on each nucleotide are joined by phosphodiester bonds. The polynucleotide can be made up of deoxyribonucleotide bases or ribonucleotide bases. Polynucleotides include DNA and RNA, and can be manufactured synthetically in vitro or isolated from natural sources.

The term "promoter" as used herein denotes a region within a gene to which transcription factors and/or RNA polymerase can bind so as to control expression of an associated coding sequence. Promoters are commonly, but not always, located in the 5' non-coding regions of genes, upstream of the translation initiation codon. The promoter region of a gene can include one or more consensus sequences that act as recognizable binding sites for sequence specific nucleic acid binding domains of nucleic acid binding proteins. Nevertheless, such binding sites can also be located in regions outside of the promoter, for example in enhancer regions located in introns or downstream of the coding sequence.

A "regulatory gene" is a gene involved in controlling the expression of one or more other genes.

5.1 Recombinant Cells

The present invention provides for therapeutic compositions which increase resistance to C. difficile infection, and/or reduce the amount of C. difficile toxin, and/or inhibit proliferation and/or growth of C. difficile in a subject. Such therapeutic compositions can comprise, for example, small molecule, polypeptide, or nucleic acid molecules.

In one non-limiting embodiment, the composition comprises a recombinant cell expressing an enzyme that converts a bile salt or acid to a secondary bile acid. In a non-limiting example, the recombinant cell comprises one or more exogenous nucleic acids encoding said enzyme, wherein the one or more exogenous nucleic acids are operably linked to a promoter. In certain embodiments, the promoter can be an inducible promoter or a constitutively active promoter. The promoter can be a bai operon promoter, or can be another promoter active in the recombinant cell.

In one non-limiting embodiment, the composition comprises a recombinant cell expressing a bile acid-inducible (bai) 7α/β-dehydroxylation operon. In a non-limiting example, the recombinant cell comprises one or more exogenous nucleic acids encoding a bile acid-inducible (bai) 7α/β-dehydroxylation operon, wherein the one or more exogenous nucleic acids are operably linked to a promoter.

In certain non-limiting embodiments, a "bile acid-inducible (bai) 7α/β-dehydroxylation operon" refers to a cluster of genes encoding a protein with enzymatic activity to convert primary bile acids to secondary bile acids. For example, the protein can convert a primary bile acid such as cholic acid (CA) and/or chenodeoxycholic acid (CDCA), into secondary bile acids such as deoxycholic acid (DCA) and lithocholic acid (LCA). In certain embodiments, the protein exhibits dehydroxylation activity. In other embodiments, the protein comprises a 7α-hydroxysteroid dehydrogenase. Examples of such enzymes are 7α-hydroxysteroid dehydrogenase enzymes expressed by Clostridium scindens, Clostridium hiranonis, Clostridium hylemonae, Clostridium perfringens, Clostridium sordellii, Proteocatella sphenisci, Lachnospiraceae 5_1_57FAA, Clostridiales VE202-05 and Clostridiales VE202-26, as well as active fragments thereof, and recombinant forms of said enzymes.

In certain non-limiting embodiments, the 7α-hydroxysteroid dehydrogenase is the *C. scindens* enzyme having the following amino acid sequence:

```
                                                          (SEQ ID NO: 1)
  1  mrlkdkvilv  tastrgigla  iaqacakega  kvymgarnle  rakarademn  aaggnvkyvy 61  ndatkeetyv  tmieeiieqe  gridvlvnnf  gssnpkkdlg  iantdpevfi  ktvninlksv 121  fiasqtavky  maengggsii  nissvgglip  disqiaygts  kaainyltkl  iavhearhni 181  rcnavlpgmt  atdavqdnlt  ddfrnfflkh  tpiqrmglpe  eiaaavvyfa  sddaayttgq 241  iltvsggfgl  atpifgdlse  rsdarg
``` as set forth in GenBank Accession No. AAB61151, which may be encoded by a nucleic acid as set forth in GenBank Accession No. M58473, and as set forth in FIG. 17 (SEQ ID NO:2). In certain non-limiting embodiments, said enzyme may be provided by a host cell, such as a bacterium, engineered to contain a nucleic acid encoding SEQ ID NO:1 or a protein having one, two, or three conservative substitutions therein, operably linked to a constitutively or inducibly active promoter element, as described herein. In a certain non-limiting embodiment, said enzyme may be provided by a host cell, such as a bacterium, engineered to contain and express a nucleic acid comprising SEQ ID NO:2 or a nucleic acid having a sequence that is at least 90 percent, or at least 95 percent, or at least 99 percent homologous thereto (where homology may be determined using standard software such as BLAST or FASTA). In certain non-limiting embodiments, the enzyme may be one of the following, or a combination thereof: an enzyme having the amino acid sequence set forth in GenBank Accession No. EIA17829 (7α-hydroxysteroid dehydrogenase from *Clostridium perfringens*); and/or an enzyme having the amino acid sequence as set forth in GenBank Accession No. AAA53556 (7α-hydroxysteroid dehydrogenase from *Clostridium sordellii*).

In one non-limiting embodiment, the recombinant cell further comprises one or more exogenous nucleic acids encoding a bile salt hydrolase, antibiotic resistance gene, and/or antibiotic susceptibility gene, wherein the nucleic acids are operably linked to a promoter.

In certain embodiments, the bile salt hydrolase is a bacterial bile salt hydrolase, for example, as encoded by a bshA and/or bshb gene of *Lactobacillus acidophilus* (See, e.g., McAuliffe et al., Appl Environ Microbiol. 2005 August; 71 (8):4925-9). Other bile salt hydrolases are described in Begley et al., Appl Environ Microbiol. 2006 March; 72(3): 1729-38).

Without being bound to any particular theory, a conjugated bile acid is referred to as a bile salt. The production of a secondary bile acid from a bile salt involves a two-step process: 1) removal of a conjugated taurine or glycine by a bile salt hydrolase (BSH) enzyme and 2) removal of a hydroxyl group from the steroid ring by enzymes comprising an enzyme encoded by the bai-operon.

In certain embodiments, expression of an antibiotic resistance gene by the recombinant cell reduces the inhibition in growth or survival of the recombinant cell caused by exposure to an antibiotic such as, but not limited to, an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic, as described herein.

In certain embodiments, expression of an antibiotic susceptibility gene by the recombinant cell increases the inhibition in growth or survival of the recombinant cell caused by exposure to an antibiotic. In certain embodiments, such antibiotics can include, but are not limited to, an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic, as described herein. In other embodiments, the recombinant cell is susceptible to an antibiotic other than the foregoing antibiotics.

In certain embodiment, the enzyme that can convert a primary bile acid to a secondary bile acid, for example, 7α-hydroxysteroid dehydrogenase, can be administered directly to a subject as a therapeutic agent. If enzyme is administered in purified form, it may be administered in a liquid or solid form, optionally may be lyophilized, optionally may comprise a pharmaceutically suitable solvent and/or carrier.

In certain embodiments, compositions disclosed herein include nucleic acid sequences encoding a bile acid-inducible (bai) 7α/β-dehydroxylation operon, said nucleic acid sequences being part of expression vectors that express the bile acid-inducible (bai) 7α/β-dehydroxylation operon or functional fragments thereof in a suitable host. In certain embodiments, such nucleic acid sequences have promoters operably linked to the bile acid-inducible (bai) 7α/β-dehydroxylation operon coding region, said promoter being inducible or constitutive, and, optionally, tissue-specific. In certain embodiments, the promoter comprises a cytomegalovirus (CMV) promoter, or any other promoter known in the art that is effective for expressing a nucleic acid n a eukaryotic cell. For example, tissue-specific promoters as described by Atta, World J Gastroenterol. 2010 Aug. 28; 16(32): 4019-4030. In other embodiments, the promoter comprises a bacterial promoter.

Delivery of nucleic acid into a subject or cell, e.g., bacterial cells of the intestinal microbiota, can be either direct, in which case the subject or cell, e.g., bacterial cells of a subject's intestinal microbiota, is directly exposed to the nucleic acid or nucleic acid-carrying vectors, or indirect, in which case, cells, e.g., a host cell, such as isolated bacterial cells of the intestinal microbiota, are first transformed with the nucleic acids in vitro, then transplanted into the subject. These two approaches are known, respectively, as in situ or ex vivo gene therapy.

For general reviews of the methods of gene therapy, see Kron and Kreppel, Curr Gene Ther 12(5):362-73 (2012); Yi et al. Curr Gene Ther 11 (3):218-28 (2011); Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); Morgan and Anderson, Ann. Rev. Biochem. 62:191-217 (1993); and May, TIBTECH 11(5): 155-215 (1993). Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990).

In certain non-limiting examples, the methods of the present invention involve transferring a gene to a host cell in culture by such methods as electroporation, lipofection, calcium phosphate mediated transfection, or viral infection. Usually, the method of transfer includes the transfer of a selectable marker to the host cells. The cells are then placed under selection to isolate those host cells that have taken up and are expressing the transferred gene. Those host cells are then delivered to a patient.

In certain embodiments, the nucleic acid can be introduced into cells, e.g., bacterial host cells, prior to administration in vivo of the resulting recombinant cell by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985)), and can be used in accordance with the present disclosure, provided that the necessary developmental and physiological functions of the recipient cells are not disrupted.

In one non-limiting embodiment, the host cell may be a *Clostridium scindens, Lactobacillus, Lactococcus, Bacillus, Bifidobacterium*, or attenuated and non-*monocytogenes Listeria*. In one non-limiting embodiment, a combination of host cells may be used.

The resulting recombinant cells can be delivered to a patient by various methods known in the art. The amount of cells envisioned for use depends on the desired effect, patient state, etc., and can be determined by one skilled in the art.

In certain embodiments, nucleic acid sequences encoding a bile acid-inducible (bai) 7α/β-dehydroxylation operon are introduced into cells such that they are expressible by the cells or their progeny, and the recombinant cells are then administered in vivo for therapeutic effect. For example, a bacterial progenitor, or stem, or other progenitor cells can be used. Any stem and/or progenitor cells which can be isolated and maintained in vitro can potentially be used (see e.g. PCT Publication WO 94/08598; Porada and Porada, J. Genet Syndr Gene Ther., May 25; S1. p 11:011 (2012); Stemple and Anderson, Cell 71:973-985 (1992); Rheinwald, Meth. Cell Bio. 21A:229 (1980); and Pittelkow and Scott, Mayo Clinic Proc. 61:771 (1986)).

In certain embodiments, the terms "vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below. A "therapeutic vector" as used herein refers to a vector which is acceptable for administration to an animal, and particularly to a human.

Vectors typically include the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA can be from the same gene or from different genes, and can be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Suitable vectors include, for example, bacteriophages, cosmids, plasmids, naked DNA, DNA lipid complexes, and other recombination vehicles typically used in the art which have been described for expression in a variety of eukaryotic and prokaryotic hosts, and can be used for gene therapy as well as for simple protein expression.

5.2 Therapeutic Bacteria

In certain non-limiting embodiments, the compositions described herein comprise one or more therapeutic bacteria, or spores thereof, for example, a *C. scindens* bacterium such as described in Morris et al., "*Clostridium scindens* sp. nov., a Human Intestinal Bacterium with Desmolytic Activity on Corticoids," Int J Syst Bacteriol, October 1985, 35:478-481, and/or Krafft et al., "Purification and characterization of a novel form of 20 alpha-hydroxysteroid dehydrogenase from *Clostridium scindens*," J. Bacteriol. June 1989, 171:2925-2932. In certain non-limiting embodiments, a *C. scindens* bacterium is as deposited in, and available from, the American Type Culture Collection, accession number ATCC 35704, Strain Designation VPI 13733. *C. scindens* 16S ribosomal RNA gene sequence is set forth in GenBank Accession No. AF262238, and *C. scindens* genome nucleic acid sequence from a whole genome shotgun sequencing project is set forth in GenBank Accession No. ABFY 02000000. Non-limiting examples of characteristics of *C. scindens* are expression of the enzymes 20 alpha-hydroxysteroid dehydrogenase, 7-beta dehydrogenase, 7 alpha-dehydroxylase, and steroid desmolase.

In various non-limiting embodiments of the invention, bacteria may be administered in the proliferative state or as spores, or a mixture thereof.

In certain embodiments, the therapeutic bacteria described herein can be modified, for example, by introducing one or more nucleic acids into the bacteria, thereby producing recombinant bacteria. Such nucleic acids can comprise, for example, a bile acid-inducible (bai) 7α/β-dehydroxylation operon, antibiotic resistance gene, antibiotic susceptibility gene, and/or a bile salt hydrolase gene, as described herein. Such recombinant bacteria can be prepared as described herein.

In certain non-limiting embodiments, *C. scindens* may be administered in the form of purified bacteria or spores or other progenitors thereof, or alternatively may be administered as a constituent in a mixture of types of bacteria, optionally including one or more probiotic bacterium or yeast. In certain non-limiting embodiments, *C. scindens* may be administered in combination with one or more of *Barnesiella intestihominis* (e.g., phylum Bacteroidetes, see, e.g., Buffie and Pamer, Nature Reviews Immunology 13:790-801), and/or *Blautia hansenii* (e.g., phylum Firmicutes, Family Lachnospiraceae, ATCC 27752), and/or *Pseudoflavonifractor capillosus* (e.g., phylum Firmicutes), and/or *Clostridium hiranonis*, and/or *Clostridium hylemonae*, and/or *Clostridium perfringens*, and/or *Clostridium sordellii*, and/or *Proteocatella sphenisci*, and/or Lachnospiraceae 5_1_57FAA, Clostridiales VE202-05 and/or Clostridiales VE202-26. In non-limiting embodiments, the present invention provides for pharmaceutical compositions comprising such forms of *C. scindens* and optionally additional bacteria. The bacteria may be administered in the form of a liquid, a suspension, a dried (e.g. lyophilized) powder, a tablet, a capsule, or a suppository, and may be administered orally or rectally. In certain embodiments, the bacteria can be administered in a food product, for example, a yogurt food product. In certain embodiments, a "food product" means a product or composition that is intended for consumption by a human or a non-human animal. Such food products include any food, feed, snack, food supplement, liquid, beverage, treat, toy (chewable and/or consumable toys), meal substitute or meal replacement.

In certain non-limiting embodiments, the present invention provides for a composition comprising an isolated *Clostridium scindens* bacterium. In one embodiment, the bacterium is in a formulation for administration to a subject. In other embodiments, the composition further comprises a second, third or fourth bacterium selected from the group consisting of *Barnesiella intestihominis, Blautia hansenii, Pseudoflavonifractor capillosus* and combinations thereof.

In other embodiments, the composition comprises one, two, three, four, five, six, seven, eight, nine, or ten or more bacteria selected from the group consisting of *Clostridium scindens, Clostridium hiranonis, Clostridium hylemonae, Clostridium perfringens, Clostridium sordellii, Proteocatella sphenisci*, Lachnospiraceae 5_1_57FAA, Clostridiales VE202-05, Clostridiales VE202-26, *Barnesiella intestihominis, Blautia hansenii*, and *Pseudoflavonifractor capillosus*.

In certain non-limiting embodiments, the present invention provides for a composition comprising an isolated *Clostridium scindens* bacterium, an isolated *Barnesiella intestihominis* bacterium, an isolated *Blautia hansenii* bacterium, and an isolated *Pseudoflavonifractor capillosus* bacterium.

In one specific non-limiting embodiment, said bacterium is *C. scindens*, but alternate or additional bacteria may be comprised in the compositions described herein, for example, bacteria which may be naturally occurring or bacteria engineered to express a bile acid-inducible (bai) 7α/β-dehydroxylation operon, or peptides expressed therefrom, such as, for example, an enzyme that converts a primary bile acid to a secondary bile acid, for example, 7α-hydroxysteroid dehydrogenase. Specific non-limiting examples of naturally occurring bacteria other than *C. scindens* that may be used to provide said enzyme are *Clostridium hiranonis* and *Clostridium hylemonae* (Ridlon, J. Lipid Res. 53:66-76 (2012), Ridlon, J Lipid Res 47, 241-259 (2006)).

5.3 Pharmaceutical Compositions

In certain embodiments, the present disclosure provides for pharmaceutical compositions which include a therapeutic composition, as described herein, such as, for example, a bile acid-inducible (bai) 7α/β-dehydroxylation operon, and/or a recombinant cell expressing said bile acid-inducible (bai) 7α/β-dehydroxylation operon, and/or a therapeutic bacterium, as described herein. Such pharmaceutical compositions can further include at least one other agent, such as a stabilizing compound or additional therapeutic agent, and can be administered in any sterile, biocompatible pharmaceutical carrier, including, but not limited to, saline, buffered saline, dextrose, and water. The composition can be in a liquid or lyophilized form and includes a diluent (Tris, citrate, acetate or phosphate buffers) having various pH values and ionic strengths, solubilizer such as Tween or Polysorbate, carriers such as human serum albumin or gelatin, preservatives such as thimerosal, parabens, benzylalconium chloride or benzyl alcohol, antioxidants such as ascrobic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

In certain embodiments, the methods and compositions of the present disclosure find use in treating *Clostridium difficile* infection. Bile acid-inducible (bai) 7α/β-dehydroxylation operon nucleic acids, peptides expressed by a bile acid-inducible (bai) 7α/β-dehydroxylation operon, recombinant cells expressing a bile acid-inducible (bai) 7α/l-dehydroxylation operon, therapeutic bacteria, and/or secondary bile acids can be administered to the patient in a pharmaceutically acceptable carrier. The route of administration eventually chosen will depend upon a number of factors and can be ascertained by one skilled in the art.

In certain embodiments, the pharmaceutical compositions of the present disclosure can be formulated using pharmaceutically acceptable carriers well known in the art in dosages suitable for oral or rectal administration. Such carriers enable the pharmaceutical compositions to be formulated as tablets, pills, capsules, liquids, gels, syrups, slurries, suspensions and the like, for oral, rectal or nasal ingestion by a patient to be treated.

Pharmaceutical compositions suitable for use in the present disclosure include, in certain embodiments, compositions where the active ingredients are contained in an effective amount to achieve the intended purpose. The amount will vary from one individual to another and will depend upon a number of factors, including the overall physical condition of the patient, e.g., severity of the *Clostridium difficile* infection.

In certain embodiments, the compositions of the present disclosure can be administered for prophylactic and/or therapeutic treatments. For example, in alternative embodiments, pharmaceutical compositions of the present disclosure are administered in an amount sufficient to treat, prevent and/or ameliorate *Clostridium difficile* infection. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Accordingly, in certain embodiments, a bile acid-inducible (bai) 7α/β-dehydroxylation operon nucleic acid, peptides expressed by a bile acid-inducible (bai) 7α/β-dehydroxylation operon, recombinant cells expressing a bile acid-inducible (bai) 7α/β-dehydroxylation operon, therapeutic bacteria, and/or secondary bile acid can be administered to a patient alone, or in combination with one or more other drugs, nucleotide sequences, lifestyle changes, etc. used in the treatment or prevention of *Clostridium difficile* infection, or symptoms thereof, or in pharmaceutical compositions where it is mixed with excipient(s) or other pharmaceutically acceptable carriers.

Single or multiple administrations of formulations can be given depending on the dosage and frequency as required and tolerated by the patient. In certain embodiments, the formulations should provide a sufficient quantity of active agent to effectively treat, prevent or ameliorate the *Clostridium difficile* infection, or symptoms or complications thereof as described herein.

5.4 Methods of Treatment

In certain non-limiting embodiments, the present invention provides for a method of reducing the risk of *C. difficile* infection and/or improving resistance to *C. difficile* infection, and/or reducing the severity of *C. difficile* infection and/or decreasing the amount of *C. difficile* toxin, comprising administering, to a subject in need of such treatment, an effective amount of a composition described herein, for example, a recombinant cell and/or a composition comprising one or more therapeutic bacteria, for example, *Clostridium scindens* optionally in combination with one or more of *Barnesiella intestihominis, Blautia hansenii,* and *Pseudoflavonifractor capillosus*. In certain embodiments, the method of reducing the severity or risk of *C. difficile* infection comprises reducing the severity or risk of a *C. difficile*-associated disease, as described herein.

Subjects in need of such treatment or compositions include subjects who are either at risk for developing *C. difficile* infection and/or subjects who have existing *C. difficile* infection.

Subjects at risk for *C. difficile* infection include individuals who are or have been treated with an antibiotic; individuals who are very young (juvenile) or who are old (geriatric, e.g. humans aged 65 years or older); individuals suffering from an inflammatory bowel disease or condition (including human inflammatory bowel disease IBD and Crohn's Disease); individuals who are hospitalized or in a long-term care facility or who have been, in the past 2, 3, 4, 5, or 6 weeks, hospitalized or in a long-term care facility; individuals with cancer including those undergoing anticancer treatment and/or stem cell or bone marrow transplant recipients; individuals who have previously suffered *C. difficile* infection, and individuals undergoing immunosuppressive therapy or with an otherwise compromised immune system (e.g. subjects infected with an immunodeficiency causing retrovirus such as HIV, FIV, FLV, etc.).

Non-limiting examples of antibiotics associated with risk of *C. difficile* infection include β-lactam antibiotics such as penicillin, ampicillin, and amoxicillin; clindamycin; cephalosporins such as but not limited to cefixime; quinolone antibiotics such as ciprofloxacin, levofloxacin and fluoroquinolone; macrolide antibiotics; trimethoprim; or sulfonamide antibiotics. In one specific non-limiting embodiment, the antibiotic is not enrofloxacin.

*C. difficile* infection, as that term is used herein, is distinct from the mere presence of the bacterium or *C. difficile* spores in the host gastrointestinal tract; infection is indicated by the presence of one or more symptom, such as intestinal tenderness, pain, and/or cramping; diarrhea for example watery diarrhea occurring at least 3, at least 5, or at least 8 times per day; blood or pus in stool or diarrhea; fever; loss of appetite; and/or nausea; and/or one or more clinical sign such as an elevated white blood cell count, decreased serum albumin, and/or the appearance of pseudomembrane in the intestinal and/or rectal mucosa. In a specific, non-limiting embodiment, *C. difficile* infection in a human may be manifested (in the case of a serious infection) by a fever of at least 38.3° C., a white blood cell count of greater than 15,000 cells/mm$^3$, serum albumin less than 2.5 g/dl, and age greater than 60 years (Zar et al., Clin. Infect. Dis. 45:302-307, 2007).

In certain non-limiting embodiments, a "*C. difficile*-associated disease" refers to any disease involving unwanted growth, toxin production, or tissue invasion in the bowel by *C. difficile*. *C. difficile*-associated diseases are known in the art and include antibiotic-associated diarrhea (i.e., *C. difficile* colitis), pseudomembranous colitis, and *C. difficile*-associated toxic megacolon. *C. difficile* colitis generally refers to profuse, watery diarrheal illness associated with the presence of at least one *C. difficile* toxin. In certain embodiments, pseudomembranous colitis refers to a severe form of *C. difficile* colitis further characterized by bloody diarrhea, fever, and bowel wall invasion by *C. difficile*. The appearance of pseudomembranes on the surface of the colon or rectum, or in the intestinal and/or rectal mucosa, is diagnostic of the condition. In certain embodiments, the pseudomembranes are composed principally of inflammatory debris and white blood cells.

In certain non-limiting embodiments, the present invention provides for a method for reducing the risk of *C. difficile* infection and/or improving resistance to *C. difficile* infection, comprising administering, to a subject in need of such treatment, an effective amount of a composition or therapeutic bacteria described herein, for example, *C. scindens* bacteria.

An effective amount of a composition or therapeutic bacteria described herein, for example, *C. scindens*, is an amount which increases resistance to *C. difficile* infection, reduces the amount of *C. difficile* toxin, and/or inhibits proliferation and/or growth of *C. difficile* in a subject. In certain non-limiting embodiments, an effective amount of *C. scindens* bacteria is at least $10^5$ bacteria, or at least $10^6$ bacteria, or at least $10^7$ bacteria, or at least $10^8$ bacteria, or at least $10^9$ bacteria.

In certain non-limiting embodiments, the present invention provides for a method for reducing the severity of *C. difficile* infection, and/or decreasing the amount of *C. difficile* toxin, and/or reducing the risk of *C. difficile* infection, and/or improving resistance to *C. difficile* infection, comprising administering, to a subject in need of such treatment, an effective amount of a composition described herein, for example, a recombinant cell or a therapeutic bacteria such as a *C. scindens* bacteria.

Reducing the severity of *C. difficile* infection refers to an amelioration in the clinical symptoms or signs of infection, for example, but not by way of limitation, one or more of the following: a decrease in the frequency or volume of diarrhea; a decrease in fever; a decrease in abdominal cramping, pain, and/or tenderness; a reduction in white blood cells in the blood; an increase in serum albumin; weight maintenance or gain; and a decrease the appearance of pseudomembrane in the intestinal and/or rectal mucosa.

In certain non-limiting embodiments, the present invention provides for a method of reducing the severity of *C. difficile* infection, and/or decreasing the amount of *C. difficile* toxin, and/or reducing the risk of *C. difficile* infection, and/or improving resistance to *C. difficile* infection, comprising administering, to a subject in need of such treatment, an effective amount of an enzyme of *C. scindens* (see Ridlon, J. Lipid Res. 54:2437-2449 (2013)).

In certain non-limiting embodiments, the present invention provides for a method for reducing the severity of *C. difficile* infection, and/or decreasing the amount of *C. difficile* toxin, and/or reducing the risk of *C. difficile* infection, and/or improving resistance to *C. difficile* infection, comprising administering, to a subject in need of such treatment, an effective amount of an enzyme that converts a bile acid to a secondary bile acid.

In certain non-limiting embodiments, the present invention provides for a method for reducing the severity of *C. difficile* infection, and/or decreasing the amount of *C. difficile* toxin, and/or reducing the risk of *C. difficile* infection, and/or improving resistance to *C. difficile* infection, comprising administering, to a subject in need of such treatment, an effective amount of a bile acid-inducible (bai) 7α/β-dehydroxylation operon nucleic acid, peptides expressed by a bile acid-inducible (bai) 7α/β-dehydroxylation operon, recombinant cells expressing a bile acid-inducible (bai) 7α/β-dehydroxylation operon, therapeutic bacteria, and/or secondary bile acid. In certain non-limiting embodiments, the compositions of the present invention are administered in purified form. In certain non-limiting embodiments, the compositions are contained in and/or produced in the subject by a bacterium or a mixture of bacteria.

In certain non-limiting embodiments, the present invention provides for a method for reducing the severity of *C. difficile* infection, and/or decreasing the amount of *C. difficile* toxin, and/or reducing the risk of *C. difficile* infection, and/or improving resistance to *C. difficile* infection, comprising administering, to a subject in need of such treatment, an effective amount of a secondary bile acid. Non-limiting examples of secondary bile acids which may be used include deoxycholic acid, lithocholic acid, or a combination thereof.

In one non-limiting embodiment, the present disclosure provides for a method for decreasing the severity of one or more symptoms of an intestinal disorder comprising administering, to a subject in need of such treatment, an effective amount of one or more of a recombinant cell; composition comprising one or more therapeutic bacteria; and an agent selected from the group consisting of an enzyme that converts a bile acid to a secondary bile acid, a secondary bile acid, purified bacteria or spores thereof expressing an enzyme that converts a bile acid to a secondary bile acid, and combinations thereof, as described herein. In certain embodiments, the symptoms are selected from the group consisting of frequency and/or volume of diarrhea; fever; abdominal cramping, pain, and/or tenderness; elevated level of white blood cells in the blood; loss of serum albumin; weight loss; appearance of pseudomembrane in the intestinal and/or rectal mucosa; and combinations thereof.

A subject treated according to the invention may be concurrently or sequentially treated with one or more agent that reduces the risk of and/or ameliorates *C. difficile* infection, for example, but not limited to, one or more antibiotic for example, but not limited to, vancomycin, metronidazole, and/or fidaxomicin; an immunotherapeutic agent such as an anti-toxin antibody; an herbal remedy such as *Puerariae radix, Scutellariae radix, Rhizoma coptidis*, garlic, or one or more extract thereof; and/or a probiotic remedy including for example, but not limited to, *Lactobaccilus acidophilus, Lactobacillus casei, Bifidobacteriua, Streptococcus thermophiles*, and/or *Saccharomyces boulardii*. In certain non-limiting embodiments, the treatment does not further comprise administration of cholestyramine.

The present disclosure also provides for methods of diagnosing or identifying a subject with a *C. difficile* infection, or at risk for *C. difficile* infection.

In certain embodiments, such methods comprise determining the level of one more bacterium present in an intestinal microbiota sample of a subject that can convert a primary bile acid to a secondary bile acid, for example, *C. scindens*, wherein the subject is diagnosed or identified as having a *C. difficile* infection, or at risk for *C. difficile* infection, when the level or amount of the one or more bacterium in the subject's microbiota is lower than a bacterium reference level. In one embodiment, a bacterium reference level is a level of bacterium, for example, *C. scindens* or any other bacteria that can convert a primary bile acid to a secondary bile acid, present in intestinal microbiota, a level below which is indicative of *C. difficile* infection, or risk of *C. difficile* infection, as determined by a medical doctor or person of skill in the art. In one non-limiting example, such a reference level can be the level of said bacterium in the microbiota of a subject who does not have a *C. difficile* infection, or at risk for *C. difficile* infection.

In other embodiments, such methods comprise determining the activity or level of 7α-hydroxysteroid dehydrogenase enzyme present in the intestinal microbiota of a subject, wherein the subject is diagnosed or identified as having a *C. difficile* infection, or at risk for *C. difficile* infection, when the activity or level of 7α-hydroxysteroid dehydrogenase enzyme in the subject's microbiota is lower than a 7α-hydroxysteroid dehydrogenase enzyme reference level. In one embodiment, a 7α-hydroxysteroid dehydrogenase enzyme reference level is an activity or level of 7α-hydroxysteroid dehydrogenase enzyme present in intestinal microbiota, a level or activity below which is indicative of *C. difficile* infection, or risk of *C. difficile* infection, as determined by a medical doctor or person of skill in the art. In one non-limiting example, such a reference level can be the activity or level of 7α-hydroxysteroid dehydrogenase in the microbiota of a subject who does not have a *C. difficile* infection, or at risk for *C. difficile* infection.

In other embodiments, such methods comprise quantifying the level of bile acid-inducible (bai) 7α/β-dehydroxylation operon nucleic acid present in a fecal sample of a subject, wherein the subject is diagnosed or identified as having a *C. difficile* infection, or at risk for *C. difficile* infection, when the level of bile acid-inducible (bai) 7α/β-dehydroxylation operon nucleic acid present in the fecal sample is lower than a bile acid-inducible (bai) 7α/β-dehydroxylation operon nucleic acid reference level. In one embodiment, a bile acid-inducible (bai) 7α/β-dehydroxylation operon nucleic acid reference level is the level of bile acid-inducible (bai) 7α/β-dehydroxylation operon nucleic acid present in a fecal sample, a level below which is indicative of *C. difficile* infection, or risk of *C. difficile* infection, as determined by a medical doctor or person of skill in the art. In one non-limiting example, such a reference level can be the level of bile acid-inducible (bai) 7α/β-dehydroxylation operon nucleic acid present in a fecal sample of a subject who does not have a *C. difficile* infection, or at risk for *C. difficile* infection. In certain embodiments, the level of nucleic acid is quantified using metagenomic sequencing, quantitative PCR, or any other method known in the art for quantifying nucleic acid in a sample.

In certain embodiments, when the level or activity of the one more bacterium present in an intestinal microbiota sample of a subject that can convert a primary bile acid to a secondary bile acid, the 7α-hydroxysteroid dehydrogenase enzyme in the subject's microbiota, and/or the level of bile acid-inducible (bai) 7α/β-dehydroxylation operon nucleic acid present in the fecal sample is above their respective reference levels, the subject is not administered an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

5.5 Non-Limiting Embodiments of the Disclosure

As described herein, the present disclosure provides for compositions and methods for reducing the severity and/or risk of *Clostridium difficile* infection.

In one non-limiting embodiment, the present disclosure provides a recombinant cell expressing a bile acid-inducible (bai) 7α/β-dehydroxylation operon, wherein the recombinant cell comprises one or more exogenous nucleic acids encoding a bile acid-inducible (bai) 7α/β-dehydroxylation operon, wherein the one or more exogenous nucleic acids are operably linked to a promoter. In certain embodiments, the recombinant cell further comprises one or more nucleic acids encoding a bile salt hydrolase, antibiotic resistance protein, and/or antibiotic susceptibility protein.

In one example, the one or more exogenous nucleic acids comprises a baiCD gene encoding a 7α-hydroxysteroid dehydrogenase enzyme.

In other embodiments, the 7α-hydroxysteroid dehydrogenase is a bacterial 7α-hydroxysteroid dehydrogenase, wherein the bacteria is selected from the group consisting of *Clostridium scindens, Clostridium hiranonis, Clostridium hylemonae, Clostridium perfringens, Clostridium sordellii, Proteocatella sphenisci*, Lachnospiraceae 5_1_57FAA, Clostridiales VE202-26, Clostridiales VE202-05 and combinations thereof.

In certain embodiments, the recombinant cell is a bacterium or spore thereof, for example, a bacterium selected from the group consisting of *Clostridium scindens, Lactobacillus, Lactococcus, Bacillus, Bifidobacterium*, and attenuated and non-*monocytogenes Listeria* strains.

In certain non-limiting embodiments, the bile acid-inducible (bai) 7α/β-dehydroxylation operon is expressed by the recombinant cell in an amount sufficient to transform a primary bile acid to a secondary bile acid by 7α/β-dehydroxylation.

In one non-limiting embodiment, the present disclosure provides for a composition comprising an isolated *Clostridium scindens* bacterium, wherein the bacterium is in a formulation for administration to a subject. In certain embodiments, the composition further comprises a second bacterium selected from the group consisting of *Barnesiella intestihominis, Blautia hansenii, Pseudoflavonifractor capillosus* and combinations thereof. In certain embodiments, the composition comprises one or more, two or more, three or more, or four of the foregoing bacteria.

In one embodiment, the recombinant cell or compositions described herein are formulated for oral or rectal administration, and can optionally further comprise a probiotic bacterium, probiotic yeast, or a combination thereof.

In one example, the formulation for oral or rectal administration is a liquid, suspension, dried powder, tablet, capsule or food product.

The present disclosure also provides for a method for reducing the risk of *Clostridium difficile* infection and/or increasing resistance to *Clostridium difficile* infection in a subject, comprising administering, to a subject in need of such treatment, an effective amount of a recombinant cell and/or composition as described herein.

The present disclosure also provides for a method for reducing the severity of *Clostridium difficile* infection and/or decreasing the amount of *Clostridium difficile* toxin in a subject, comprising administering, to a subject in need of such treatment, an effective amount of a recombinant cell and/or composition as described herein.

The present disclosure also provides for a method for reducing the risk of *Clostridium difficile* infection and/or increasing resistance to *Clostridium difficile* infection in a subject, comprising administering, to a subject in need thereof, an effective amount of an agent selected from the group consisting of an enzyme that converts a bile acid to a secondary bile acid, a secondary bile acid, purified bacteria or spores thereof expressing an enzyme that converts a bile acid to a secondary bile acid, and combinations thereof.

The present disclosure also provides for a method for reducing the severity of *Clostridium difficile* infection and/or decreasing the amount of *Clostridium difficile* toxin in a subject, comprising administering, to a subject in need thereof, an effective amount of an agent selected from the group consisting of an enzyme that converts a bile acid to a secondary bile acid, a secondary bile acid, purified bacteria or spores thereof expressing an enzyme that converts a bile acid to a secondary bile acid, and combinations thereof.

The present disclosure also provides for a method for decreasing the severity of a symptom of an intestinal disorder comprising administering, to a subject in need of such treatment, an effective amount of one or more of a recombinant cell or composition described herein, and an agent selected from the group consisting of an enzyme that converts a bile acid to a secondary bile acid, a secondary bile acid, purified bacteria or spores thereof expressing an enzyme that converts a bile acid to a secondary bile acid, and combinations thereof, wherein the symptom is selected from the group consisting of frequency and/or volume of diarrhea; fever; abdominal cramping, pain, and/or tenderness; elevated level of white blood cells in the blood; loss of serum albumin; weight loss; appearance of pseudomembrane in the intestinal and/or rectal mucosa; and combinations thereof.

In one example, the enzyme that converts a bile salt to a secondary bile acid is a 7α-hydroxysteroid dehydrogenase enzyme.

In another example, the recombinant cell, composition or agent can be administered to the subject in an amount effective to inhibit proliferation of *Clostridium difficile* in the subject.

In yet other examples, the recombinant cell, composition or agent is administered to the subject in an amount effective to reduce one or more clinical symptoms of *Clostridium difficile* infection selected from the group consisting of frequency and/or volume of diarrhea; fever; abdominal cramping, pain, and/or tenderness; elevated level of white blood cells in the blood; loss of serum albumin; weight loss; appearance of pseudomembrane in the intestinal and/or rectal mucosa; and combinations thereof.

In certain embodiments, the composition administered to a subject comprises a purified bacterium or spore thereof selected from the group consisting of *Clostridium scindens, Clostridium hiranonis, Clostridium hylemonae, Clostridium perfringens, Clostridium sordellii, Proteocatella sphenisci,* Lachnospiraceae 5_1_57FAA, Clostridiales VE202-26, Clostridiales VE202-05 and combinations thereof.

In one example, the bacterium is a purified *Clostridium scindens* bacterium.

In other examples, the composition further comprises a second bacterium selected from the group consisting of *Barnesiella intestihominis, Blautia hansenii, Pseudoflavonifractor capillosus,* and combinations thereof.

In other examples, the composition is a secondary bile acid, for example, a secondary bile acid selected from the group consisting of deoxycholic acid, lithocholic acid, and a combination thereof.

In certain embodiments, the methods described herein further comprise administering to the subject, an antibiotic, an immunotherapeutic agent, an herbal remedy, a probiotic, or combinations thereof.

In one non-limiting embodiment, the methods described herein, further comprise identifying a subject with a *Clostridium difficile* infection, or at risk for *Clostridium difficile* infection, comprising obtaining an intestinal microbiota sample from a subject and determining the level of one or more bacterium present in the intestinal microbiota sample; comparing the level of the one or more bacterium in the sample with a reference bacterium level; and administering the recombinant cell, composition or agent to the subject when the level of one or more bacterium in the sample is lower than the bacterium reference level. In certain embodiments, the one or more bacterium is selected from the group consisting of *Clostridium scindens, Clostridium hiranonis, Clostridium hylemonae, Clostridium perfringens, Clostridium sordellii, Proteocatella sphenisci,* Lachnospiraceae 5_1_57FAA. Clostridiales VE202-05, Clostridiales VE202-26, and combinations thereof. In certain embodiments, the method further comprising administering an antibiotic to the subject, wherein, when the level of the one or more bacterium in the sample is equal to or greater than the bacterium reference level, the antibiotic administered to the subject is not an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

In other non-limiting embodiments, the methods described herein further comprise identifying a subject with a *Clostridium difficile* infection, or at risk for *Clostridium difficile* infection, comprising obtaining an intestinal microbiota sample from a subject and determining the activity or level of 7α-hydroxysteroid dehydrogenase enzyme present in the intestinal microbiota sample; comparing the activity or level of 7α-hydroxysteroid dehydrogenase enzyme in the sample with a reference 7α-hydroxysteroid dehydrogenase enzyme activity or level; and administering the recombinant cell, composition or agent to the subject when the activity or level of 7α-hydroxysteroid dehydrogenase enzyme in the sample is lower than the reference 7α-hydroxysteroid dehydrogenase enzyme activity or level.

The present disclosure also provides for a method of diagnosing a subject with a *Clostridium difficile* infection, or at risk for *Clostridium difficile* infection, comprising obtaining an intestinal microbiota sample from a subject and determining the level of one or more bacterium present in the intestinal microbiota sample; comparing the level of one or more bacterium in the sample with a reference bacterium level; and diagnosing the subject as having a *Clostridium difficile* infection, or at risk for *Clostridium difficile* infection, when the level of the one or more bacterium in the sample is lower than the bacterium reference level. In certain embodiments, the one or more bacterium is selected from the group consisting of *Clostridium scindens, Clostridium hiranonis, Clostridium hylemonae, Clostridium perfringens, Clostridium sordellii, Proteocatella sphenisci,* Lachnospiraceae 5_1_57FAA, Clostridiales VE202-05, Clostridiales VE202-26, and combinations thereof. In certain embodiments, the method further comprising administering an antibiotic to the subject, wherein, when the level of the one or more bacterium in the sample is equal to or greater than the bacterium reference level, the antibiotic administered to the subject is not an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

In other embodiments, the present disclosure provides for a method of diagnosing a subject with a *Clostridium difficile* infection, or at risk for *Clostridium difficile* infection, comprising obtaining an intestinal microbiota sample from a subject and determining the activity or level of 7α-hydroxysteroid dehydrogenase enzyme present in the intestinal microbiota sample; comparing the activity or level of 7α-hydroxysteroid dehydrogenase enzyme in the sample with a reference 7α-hydroxysteroid dehydrogenase enzyme activity or level; and diagnosing the subject as having a *Clostridium difficile* infection, or at risk for *Clostridium difficile* infection, when the activity or level of 7α-hydroxysteroid dehydrogenase enzyme in the sample is lower than the reference 7α-hydroxysteroid dehydrogenase enzyme activity or level.

In other non-limiting embodiments, the methods described herein further comprise identifying a subject with a *Clostridium difficile* infection, or at risk for *Clostridium difficile* infection, comprising obtaining a fecal sample from a subject and quantifying the level of bile acid-inducible (bai) 7α/β-dehydroxylation operon nucleic acid present in the fecal sample; comparing the level of bile acid-inducible (bai) 7α/β-dehydroxylation operon nucleic acid in the fecal sample with a reference bile acid-inducible (bai) 7α/β-dehydroxylation operon nucleic acid level; and administering the recombinant cell, composition or agent to the subject when the level of bile acid-inducible (bai) 7α/β-dehydroxylation operon nucleic acid in the fecal sample is lower than the reference level.

In other embodiments, the present disclosure provides for a method of diagnosing a subject with a *Clostridium difficile* infection, or at risk for *Clostridium difficile* infection, comprising obtaining a fecal sample from a subject and quantifying the level of bile acid-inducible (bai) 7α/β-dehydroxylation operon nucleic acid present in the fecal sample; comparing the level of bile acid-inducible (bai) 7α/l-dehydroxylation operon nucleic acid present in the fecal sample with a reference bile acid-inducible (bai) 7α/β-dehydroxylation operon nucleic acid level; and diagnosing the subject as having a *Clostridium difficile* infection, or at risk for *Clostridium difficile* infection, when the level of bile acid-inducible (bai) 7α/β-dehydroxylation operon nucleic acid present in the fecal sample is lower than the reference level.

In certain non-limiting embodiments, the methods described herein further comprise administering an antibiotic to the subject, wherein, when the level of one or more bacterium in the sample is equal to or greater than the bacterium reference level; when the activity or level of 7α-hydroxysteroid dehydrogenase enzyme in the sample is greater than the reference 7α-hydroxysteroid dehydrogenase enzyme activity or level; or when the level of bile acid-inducible (bai) 7α/β-dehydroxylation operon nucleic acid present in the fecal sample is greater than the reference level; wherein the antibiotic administered to the subject is not an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

In other non-limiting embodiments, the present disclosure provides for a method of reducing risk of developing *Clostridium difficile*-associated disease in a subject receiving antibiotic therapy, comprising administering, to a subject in need of such treatment, an effective amount of a recombinant cell or composition described herein.

In other embodiments, the present disclosure provides for a method of preventing or treating *Clostridium difficile*-associated disease in a subject comprising administering, to a subject in need of such treatment, an effective amount of a recombinant cell or composition described herein. In certain embodiments, the *Clostridium difficile*-associated disease is *Clostridium difficile* colitis or pseudomembranous colitis. In certain embodiments, the subject is, has or will receive antibiotic therapy The present disclosure also provides for a kit comprising the recombinant cell, and/or agent, and/or therapeutic composition described herein.

6. EXAMPLE

The presently disclosed subject matter will be better understood by reference to the following Example, which is provided as exemplary of the invention, and not by way of limitation.

6. Example: Native Intestinal Bacteria Augment Resistance to *C. difficile* Infection Through Secondary Bile Acid Biosynthesis As demonstrated by the experiments described below, and utilizing mouse models of *C. difficile* infection and a cohort of infection-susceptible patients, we have characterized and modeled the dynamics of microbiome composition and infection resistance in mice and humans. After leveraging this information to precisely identify native intestinal bacteria associated with infection resistance, we developed a murine bacterial transfer model informed by Koch's postulates, FMT protocols, and bioinformatic approaches to confirm that as few as one species of resistance-associated bacterium, *Clostridium scindens*, could mitigate *C. difficile* infection and associated disease. Finally, we present evidence that *C. scindens* enhances *C. difficile* resistance by chemically transforming host-produced bile salts, suggesting approaches to improve the identification and treatment of *C. difficile*-susceptible individuals.

6.1 Variance of Antibiotic Impacts

The use of multiple different antibiotic classes is associated with *C. difficile* infection in hospital settings (Rupnik, Nat Rev Microbiol 7, 526-536 (2009); Surawicz, Nat Rev Gastroenterol Hepatol 8, 330-339 (2011)), but the kinetics of infection susceptibility following antibiotic use is not well described. We characterized the impact of agents with diverse antimicrobial spectra on *C. difficile* infection resistance by treating independently-housed colonies of C57BL/6J mice with one of three antibiotic classes for three days and challenging mice from these colonies with 1000 *C. difficile* spores (VPI10463) at five intervals throughout a 21-day period following antibiotic cessation. Susceptibility was determined by enumeration of *C. difficile* from the large intestine of animals sacrificed 24 hours after challenge.

Consistent with previous findings (Buffie 2012), treatment with the *C. difficile*-associated lincosaminde antibiotic clindamycin resulted in increased infection susceptibility for the entire 21-day period post-antibiotic in at least one of six colonies (FIG. 1A). In contrast, treatment with the β-lactam (ampicillin) resulted in a relatively short-lived period of susceptibility, with all three ampicillin-treated colonies recovering resistance to infection by day 10 post-antibiotic (FIG. 1B). Treatment with enrofloxacin did not increase susceptibility to *C. difficile* infection (FIG. 1C), perhaps reflecting the resistance of the mouse colonies to this antibiotic. *C. difficile* toxin expression correlated significantly with *C. difficile* abundance in the intestine (FIG. 2b). FIG. 2a shows the strategy for determining *C. difficile* susceptibility during post-antibiotic exposure. Quantitative RT-PCR of total 16S indicated that none of the antibiotic regimens resulted in substantial decreases in bacterial density (FIG. 2C). Quantification of *C. difficile* toxin expression in the supernatant from large intestine content correlated strongly with *C. difficile* abundance, confirming the infection virulence (FIG. 1D). Longitudinal characterization of the intestinal microbiota by 454 pyrosequencing of the bacterial 16S V1-3 region before (FIGS. 1E-G) and after *C. difficile* challenge revealed that the three antibiotics had diverse impacts on the bacterial phylotype composition as well.

6.2 Resistance-Associated Mouse Microbiota

We exploited the variance in intestinal bacterial composition and infection susceptibility among mice treated with different antibiotics to determine relationships between *C. difficile* inhibition and intestinal microbiota structure. A prior study of 10 human patients correlated *C. difficile* infection with reduced alpha diversity (i.e. diversity within individuals) of the intestinal microbiota[38], and a separate study associated recovery of alpha diversity with the clearance of *C. difficile* using a murine infection model[35]. Consistent with these findings, we found that decreased alpha diversity correlated with susceptibility to infection while the alpha diversity of resistant samples was comparable to pre-treatment microbiota (FIG. 3a).

Considering beta diversity (i.e. diversity between individuals) of microbiota samples, we found that clindamycin and ampicillin administration induced distinct but overlapping microbiota changes associated with infection susceptibility as indicated by the time-resolved trajectories in unweighted UniFrac[39] principal coordinate plots. Following antibiotic-mediated perturbation, recovery of infection resistance correlated with return to a common coordinate space shared by pre-treatment samples (with unperturbed microbiota) (FIG. 3b). However, these resistance- and susceptibility-associated coordinate spaces overlapped and did not completely resolve seven animals with respect to infection susceptibility. These exceptions generally corresponded to animals transitioning from susceptible to resistant states at early timepoints post-antibiotic and harbored microbiota with low alpha diversity. Interestingly, like beta diversity measured by UniFrac distances, microbiota alpha diversity correlated poorly with infection resistance during this early period following antibiotic exposure, suggesting that recovery of more precise microbiota features (e.g. individual taxa) resulted in enhanced infection resistance.

We correlated resistance with individual bacterial species abundances, corresponding to operational taxonomic units (OTUs) grouped at ≥97% 16S sequence identity (FIG. 4), and discovered that 11 bacterial OTUs correlated strongly with infection resistance (FIG. 3 c). These OTUs represent a small fraction of the microbiota membership (6%) and were comprised primarily by *Clostridium* cluster XIVa, including the OTU with the strongest resistance correlation, *Clostridium scindens*. Importantly, *C. scindens* was also one of two OTUs correlated with resistance among animals harboring low-biodiversity microbiota (FIG. 3a, red box) that nevertheless remained resistant to *C. difficile* (FIG. 3c).

6.3 Inter-Species *C. difficile* Resistance

To assess the relevance of specific bacterial species to *C. difficile* resistance in humans, we extended our study to a cohort of patients undergoing allogeneic hematopoietic stem cell transplantation (allo-HSCT). The majority of these patients have been diagnosed with a hematological malignancy and receive conditioning with high doses of chemotherapy and/or total body irradiation as well as various antibiotics during the course of their transplantation, especially while neutropenic and immunodeficient (Table 1). They incur reduced microbiota biodiversity, which is associated with increased risk of bacterial blood stream infections[40] as well as *C. difficile* infection[41]. In contrast to carefully-controlled animal studies, temporal variation in antibiotic administration and sampling times among patients complicates the study of relationships between microbiota composition and susceptibility to infection.

Figure 7A:
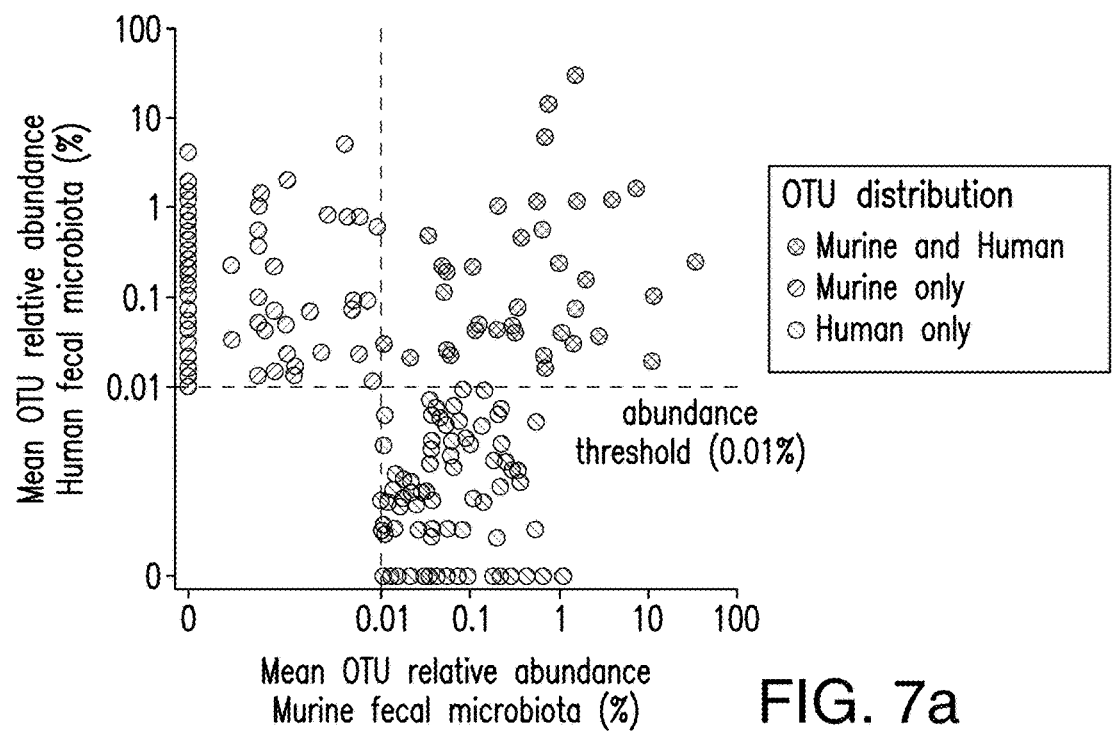
Figure 7B:
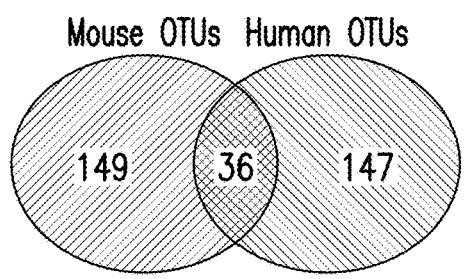
Figure 7C:
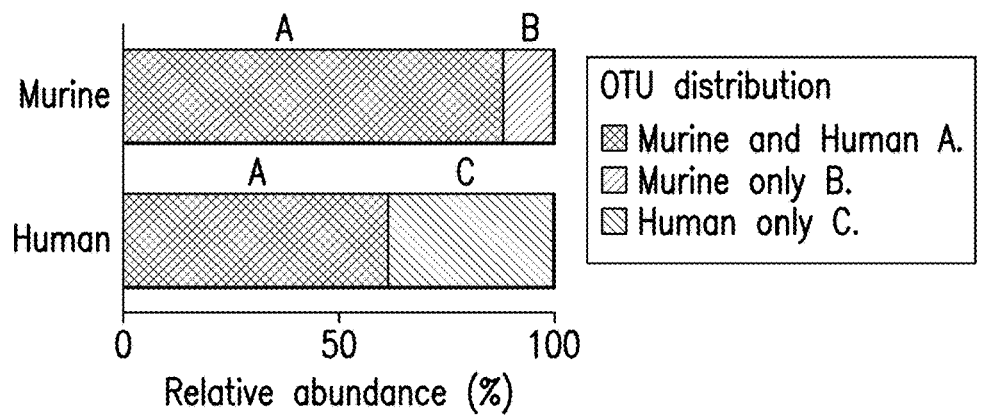
Figure 7D:
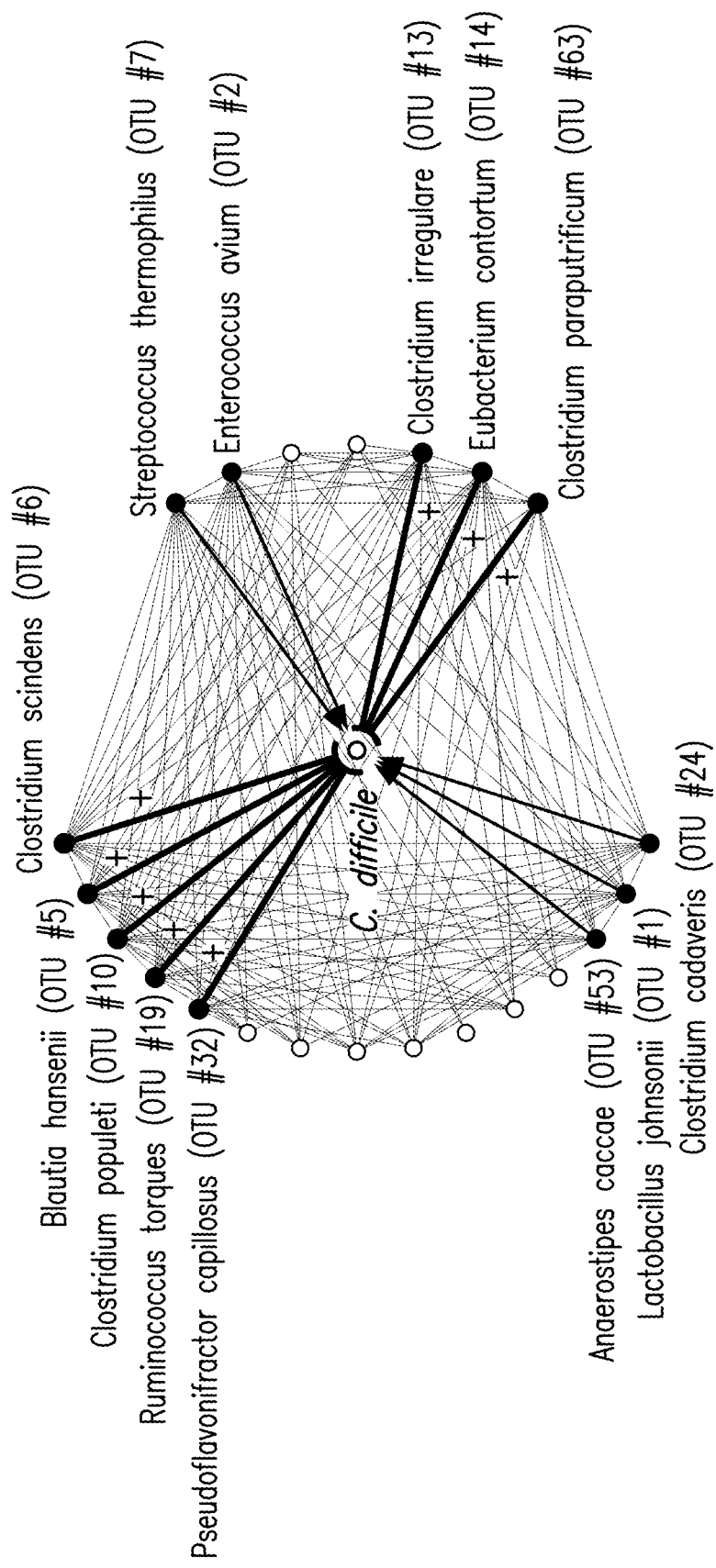
Figure 7E:
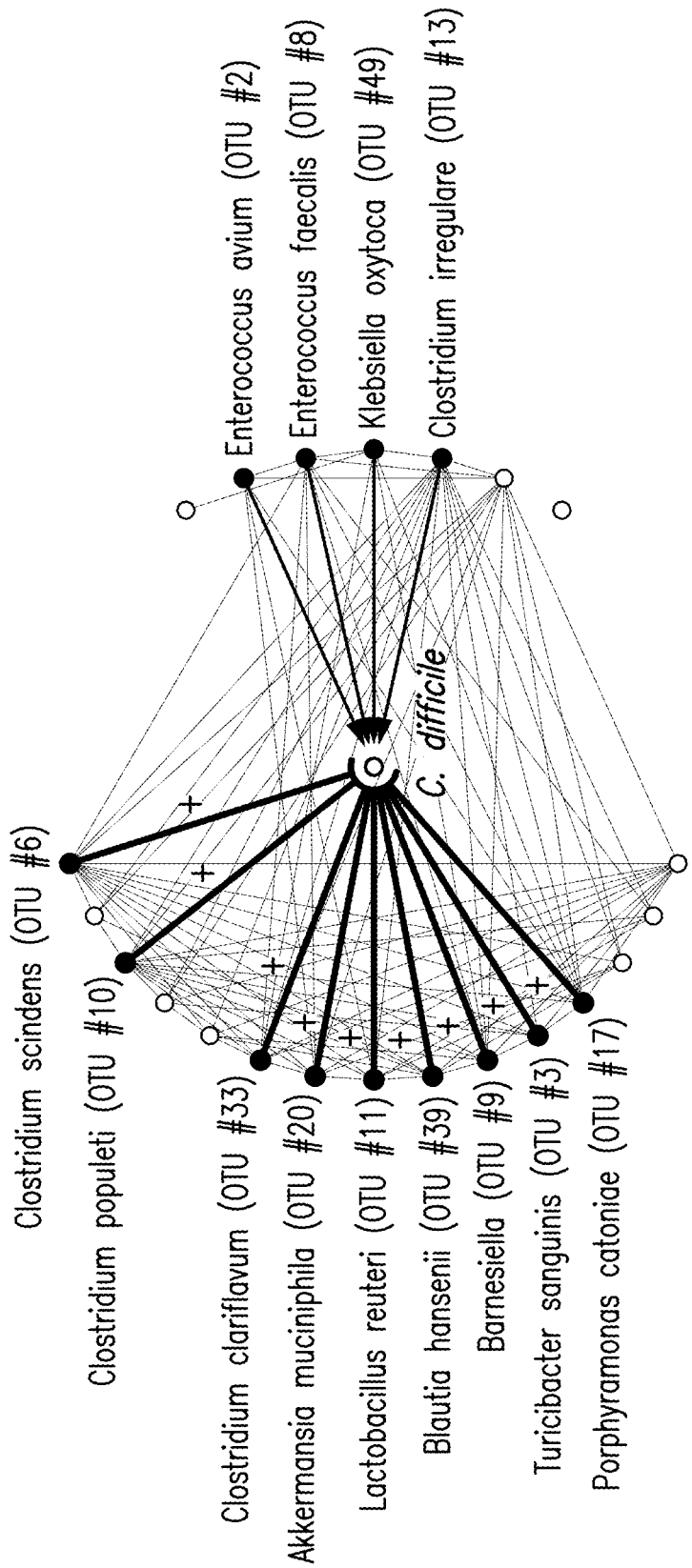

To address these challenges and evaluate resistance associations of intestinal OTUs in a *C. difficile*-colonized allo-HSCT patient cohort, we employed a recently developed systems biology approach[42], which integrates antibiotic delivery schedules and time-resolved microbiota sequencing data to mathematically model the contributions of antibiotic sensitivity, bacterial growth rates, and bacteria-bacteria interactions to intestinal microbiota composition dynamics. This model in turn enables the inference of native intestinal bacterial populations that inhibit *C. difficile*. For our analysis we included allo-HSCT patients with fecal samples PCR-positive for *C. difficile* 16S and *C. difficile* toxin B (tcdB) within 7 days post-stem cell infusion (n=24), including 12 patients clinically diagnosed with *C. difficile* infection and 12 patients that were discovered to be transient *C. difficile* carriers by retrospective testing (FIG. 5a, FIG. 6, Table 1), with full information on antibiotic treatment, fecal microbiota composition (from 16S rRNA pyrosequencing), as well as total and *C. difficile*-specific 16S rRNA copies per gram of stool. In parallel, we applied this same modeling approach to our murine *C. difficile* susceptibility timecourse study. To facilitate comparisons across the mouse and patient datasets, we clustered murine and human microbiota together to define OTUs (≥97% sequence similarity) and identified 36 phylogenetically diverse OTUs abundant in both mouse and human datasets (>0.01% mean relative abundance) (FIG. 7a, b) that together accounted for a majority of both the human and mouse microbiota structure (FIG. 7c).

Application of the inference method to the murine dataset identified 9 OTUs displaying strong inhibition against *C. difficile* (FIG. 5b), including 5 OTUs correlated with resistance in our previous analyses (FIG. 3c). A comparison of the normalized interaction networks from the human (FIG. 7d) and the murine models (FIG. 7e) revealed some differences in the interactions among OTUs. Despite these differences, the human model identified two OTUs strongly inhibiting *C. difficile* that were also among the *C. difficile*-inhibitory OTUs identified in the murine model (FIG. 5b, c). The OTU that displayed the strongest *C. difficile* inhibition was *C. scindens*, the OTU with the strongest resistance correlations identified in our murine infection susceptibility study (FIG. 3c). Additionally, in both the murine and human models, *Blautia* was predicted to inhibit (albeit different OTUs), and one OTU was predicted to positively interact with *C. difficile*. Overall these comparisons indicate that while there are differences in microbiota membership across host species, there may be conserved bacterial species, and perhaps underlying microbial ecology principles, that govern microbiota-mediated resistance against *C. difficile* infection.

6.4 Rational Restoration of Infection Resistance

To evaluate whether the relationships we identified between native intestinal bacteria and *C. difficile* infection resistance were causal, we developed a protocol informed by Koch's postulates and bioinformatic approaches to adoptively transfer resistance-associated bacteria. Drawing from our in-house collection and public repositories, we identified and cultured a phylogenetically diverse consortium of four intestinal bacterial isolates with species-level 16S homology to OTUs that were correlated with infection resistance and predicted to inhibit *C. difficile* in our mouse and human analyses (FIG. 7). This 4-bacteria consortium included *Barnesiella intestihominis* (OTU 9), *Blautia hansenii* (OTU 39), *Pseudoflavonifractor capillosus* (OTU 32) and *C. scindens* (OTU 6) (FIG. 8). Following antibiotic administration[43] and a two-day antibiotic washout period, 10 separately-housed mice were administered a suspension containing the 4-bacteria consortium or vehicle (PBS) once daily for two days prior to a *C. difficile* infection challenge (1,000 spores). Additionally, since *C. scindens* had the strongest resistance correlation in mice (including animals harboring low-biodiversity intestinal microbiota) (FIG. 3c) and was conserved in the human microbiota as the strongest *C. difficile* inhibitor (FIG. 5b), we administered a suspension containing only this bacterium in a third arm.

Figure 9A:
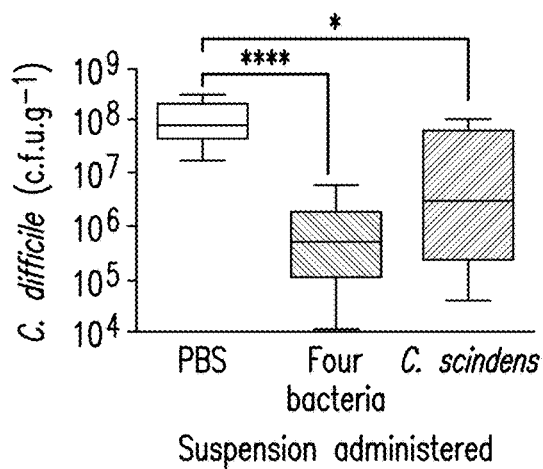
Figure 9B:
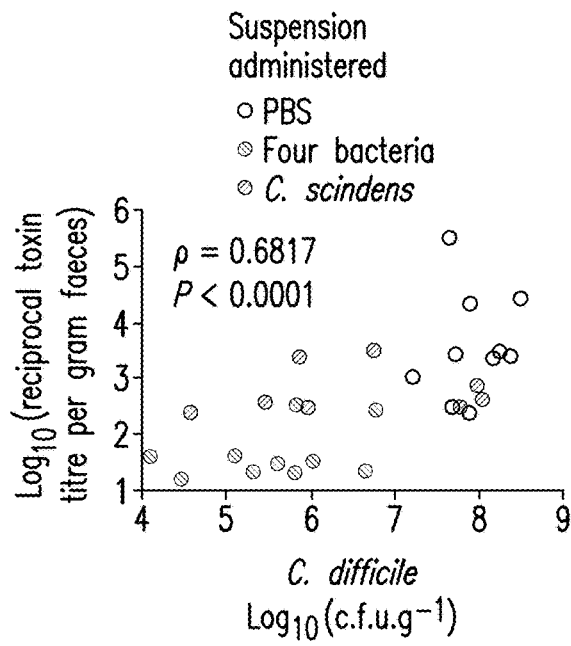
Figure 9C:
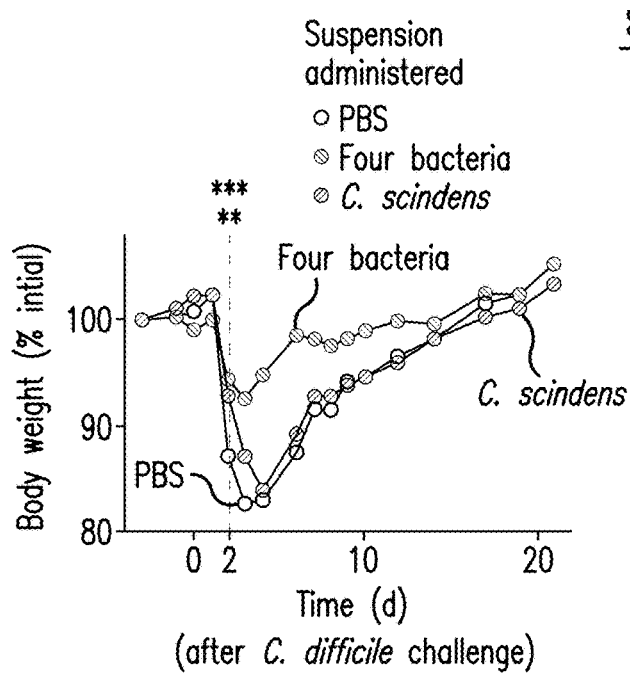
Figure 9D:
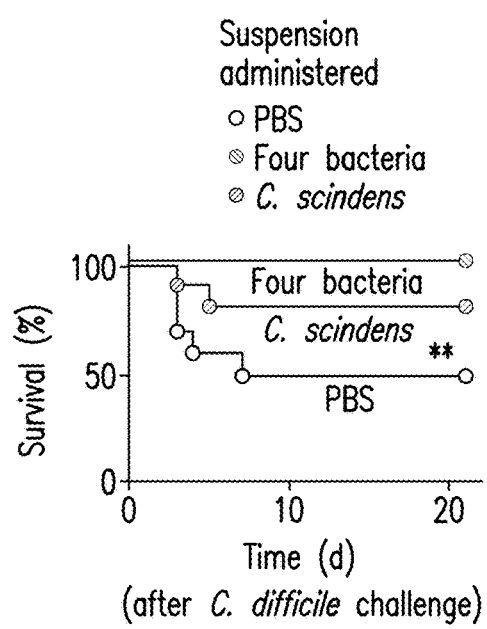

Adoptive transfer of the 4-bacteria consortium ameliorated *C. difficile* infection (FIG. 9a, b, FIG. 10) as well as associated weight loss (FIG. 9c, FIG. 11) and mortality (FIG. 9d) significantly compared to control. Transfer of the three isolates (*B. hansenii, B. intestihominis*, and *P. capillosus*) individually however, did not significantly enhance infection resistance (FIG. 9g). Remarkably, transfer of *C. scindens* alone was also able to significantly mitigate *C. difficile* infection by these metrics (FIG. 9a, b, c, d, FIGS. 10, 11). Engraftment of the adoptively transferred bacteria was confirmed (FIG. 12) by their 16S sequence homology to the input suspension as well as the native intestinal bacteria associated with resistance in our initial *C. difficile* susceptibility timecourse experiments (FIGS. 3,5), thus fulfilling Koch's criteria for establishing causal relationships (albeit between a microbe and a beneficial health outcome rather than a disease, in this case). Additionally, engraftment of *C. scindens* across all experiment arms correlated significantly with *C. difficile* infection resistance (FIG. 9e), accounting for a substantial amount of the variability in protection observed among the mice administered *C. scindens*, suggesting that improving the efficiency of bacterial engraftment may enhance the protective effects of the adoptive transfer. Importantly, adoptive transfer and engraftment of bacteria was precise and did not produce significant changes in the overall microbiota structure that resulted in increased microbiota biodiversity or density compared to control (FIG. 9f,h).

6.5 Bile Acid-Dependent Infection Resistance

Microbiota-derived products can inhibit intestinal pathogens through host-dependent and direct antimicrobial mechanisms, but the bacterial source of most protective products remains undefined. For example, some secondary bile acids can inhibit *C. difficile* in vitro[44] and are abundant in the intestines of mice and humans[45], but the precise origin of these compounds and their relative contribution to *C. difficile* inhibition in vivo remains unclear. Noting that *C. scindens* expresses enzymes crucial for secondary bile acid synthesis[46] that are uncommon among intestinal bacteria[47], we hypothesized that the *C. difficile*-protective effects of *C. scindens* may be associated with and dependent upon this rare biosynthetic capacity.

Figure 13A:
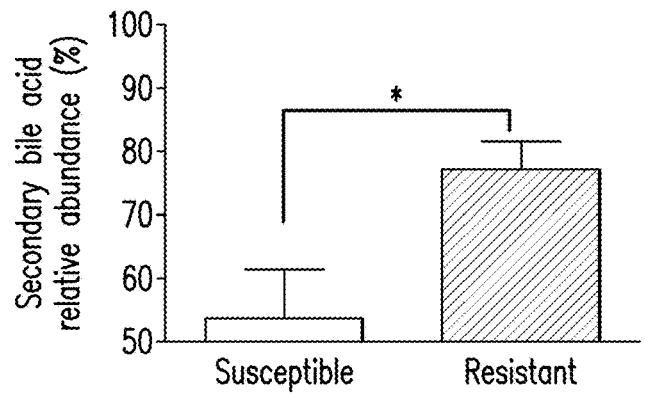
Figure 13B:
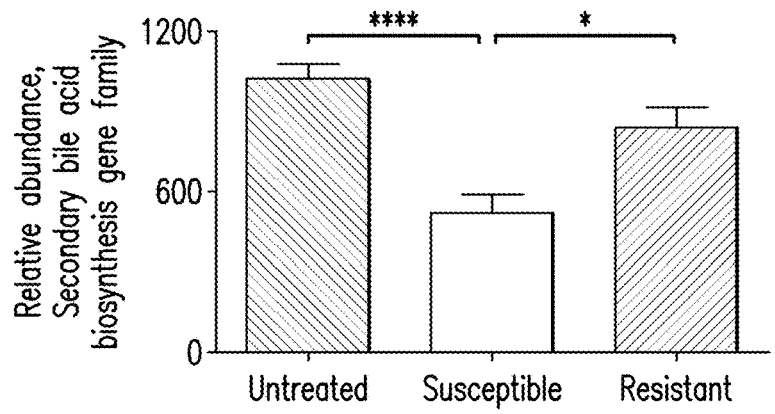
Figure 13C:
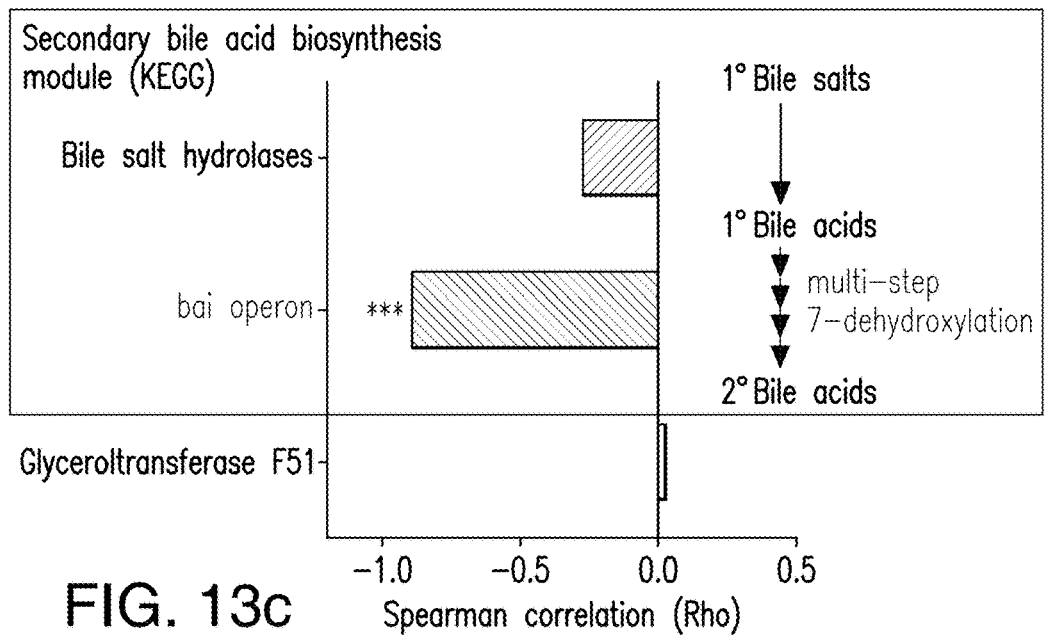
Figure 13D:
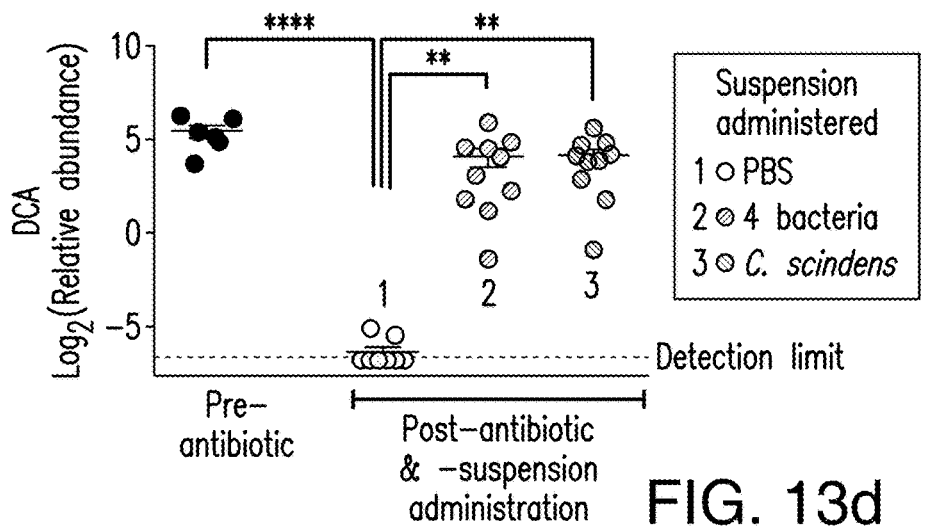
Figure 13E:
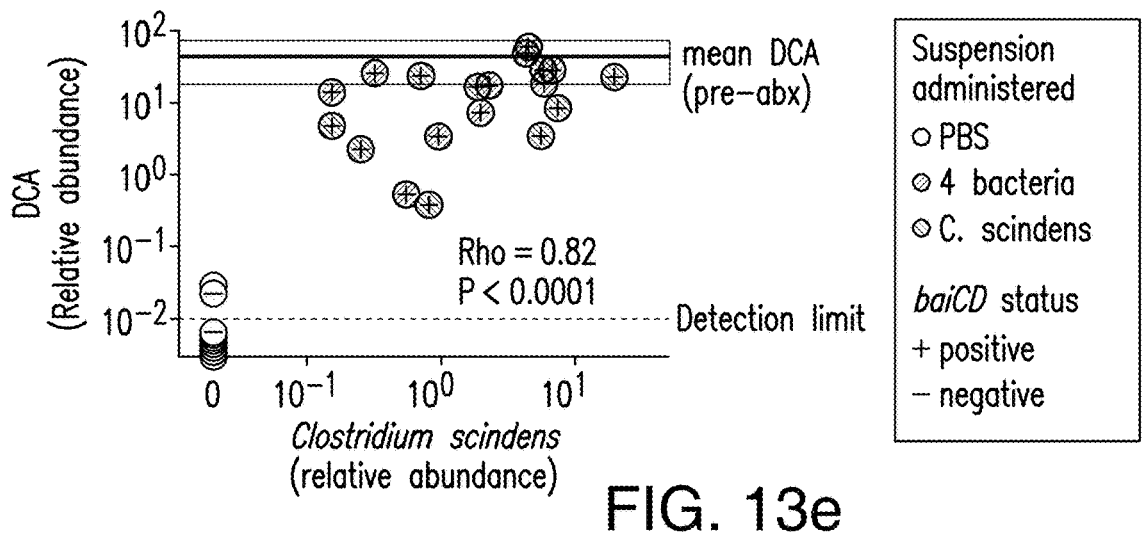
Figure 13F:
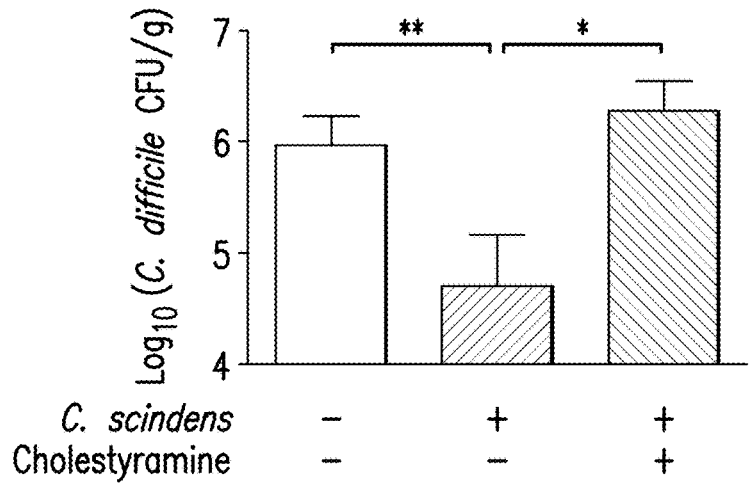
Figure 13H:
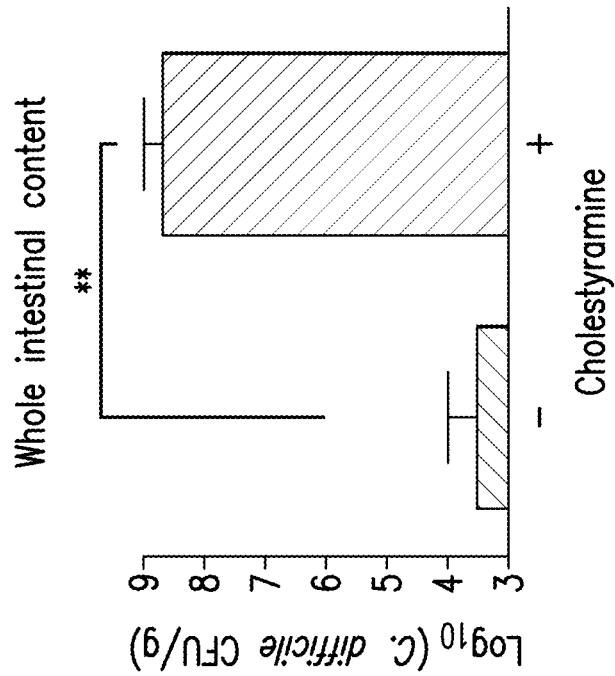

Biochemical quantification of bile acid species indicated that recovery of secondary bile acids correlated with *C. difficile* resistance following antibiotic exposure (FIG. 13a). Using the computational approach PICRUSt[48] to infer the abundance of gene families in bacterial communities from our initial murine intestinal microbiota 16S sequencing (FIGS. 1, 3), we found that increased abundance of the secondary bile acid biosynthesis gene family was correlated significantly with *C. difficile* resistance (FIG. 13b). To confirm the predictive metagenomic results, we subjected intestinal content samples from a representative subset of the same antibiotic-exposed animals to shotgun metagenomic sequencing and targeted quantification of secondary bile acid biosynthesis gene family members. These included bile salt hydrolases and genes comprising the bile acid-inducible (bai) 7α/β-dehydroxylation operon possessed by *C. scindens*. Our analysis revealed that abundance of the bai operon was correlated significantly with resistance to *C. difficile* infection (FIG. 13c) while the bile salt hydrolases (BSHs) were not, consistent with reports indicating that BSH-encoding genes are widely distributed among intestinal bacterial species while an extremely small fraction of the microbiota is estimated to possess a complete secondary bile acid synthesis pathway[47].

Figure 16C:
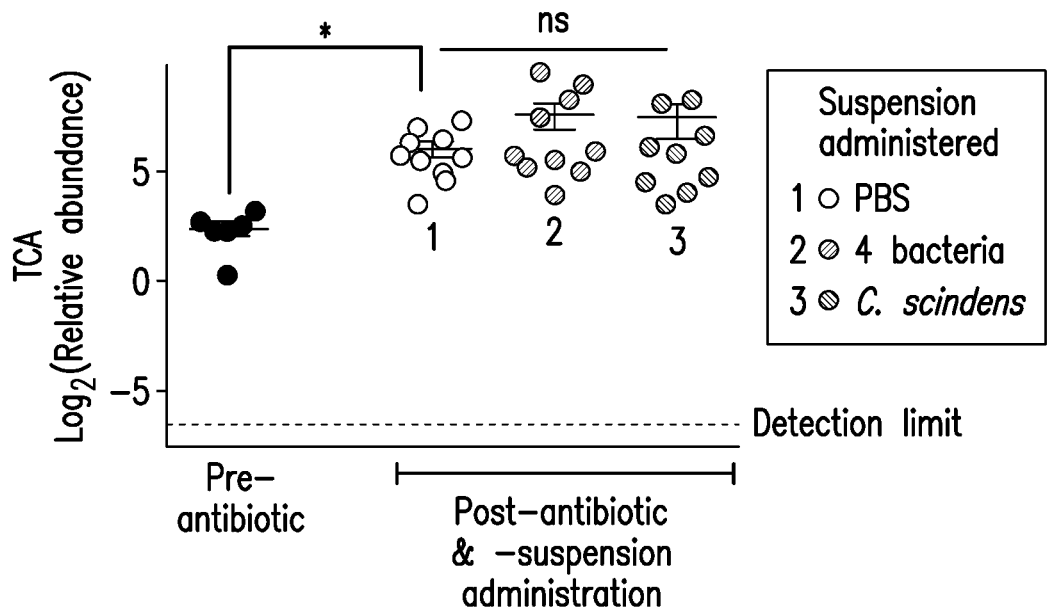
Figure 16D:
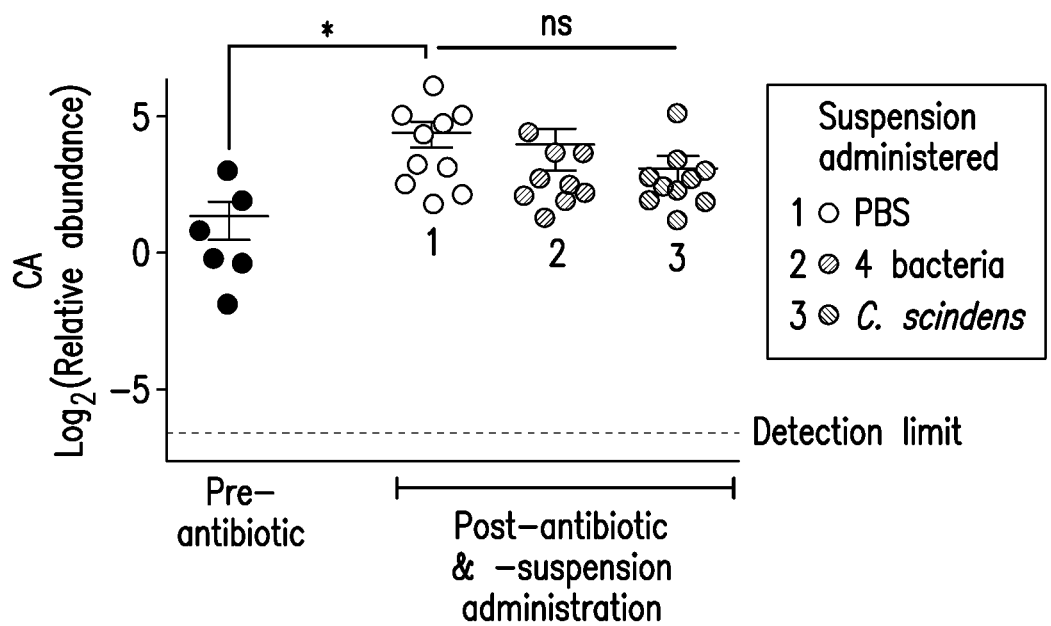
Figure 16E:
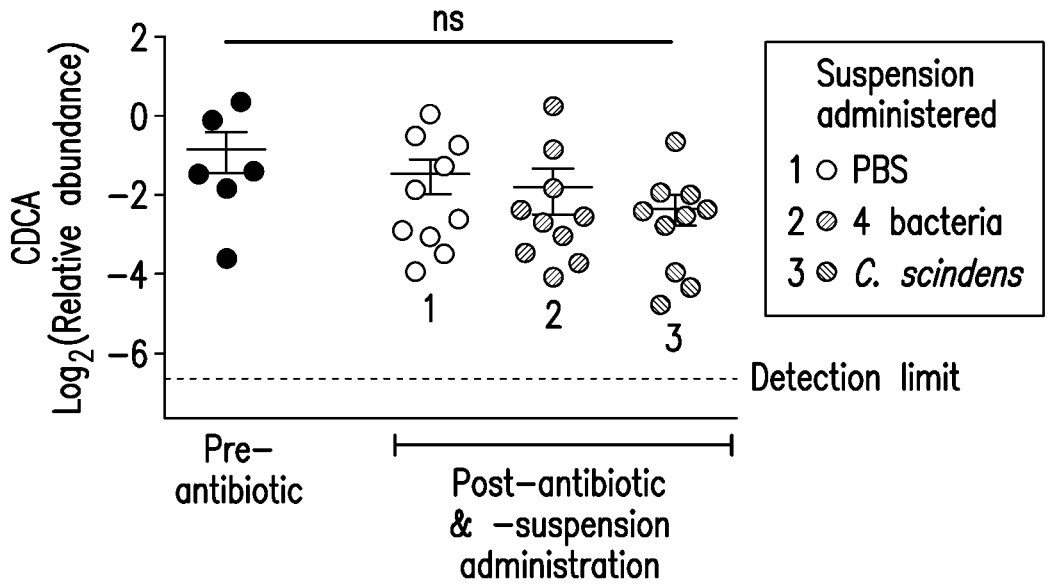
Figure 16F:
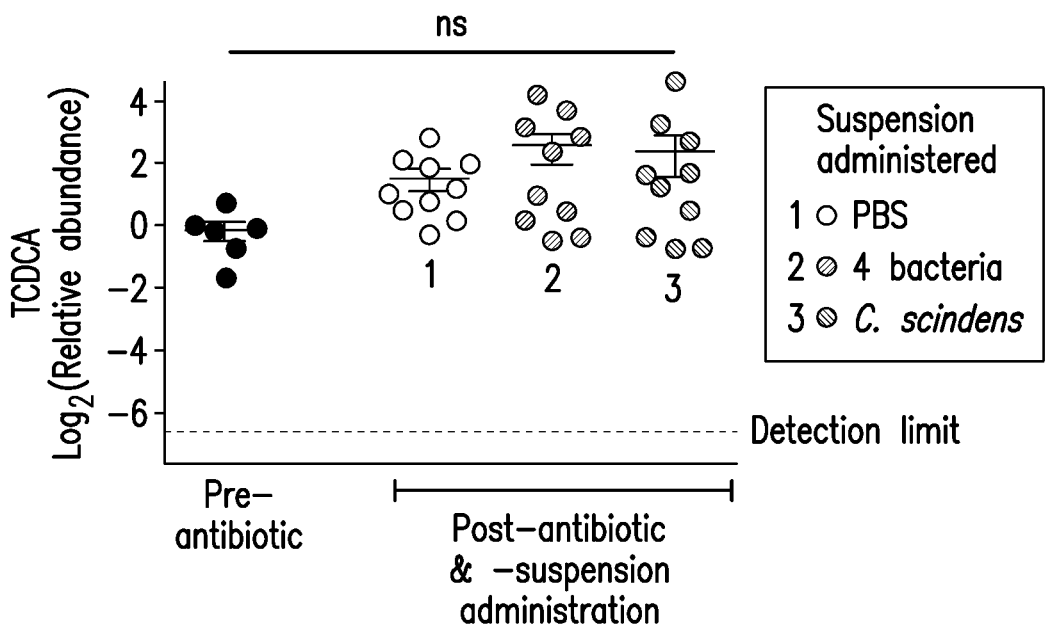

Using a PCR-based assay for baiCD[49], the gene encoding the 7α-hydroxysteroid dehydrogenase enzyme critical for converting primary bile acids to secondary species, we confirmed the presence of this gene in the intestinal microbiomes of animals prior to antibiotic exposure and following recovery of *C. difficile* resistance, as well as its absence among antibiotic-exposed animals who had not recovered resistance (FIG. 14). We also confirmed that mice receiving the 4-bacterium consortium or *C. scindens* alone, but not those receiving vehicle (PBS), harbored a baiCD+ microbiome. Predictive metagenomic analysis also indicated that the secondary bile acid biosynthesis gene family abundance was restored to pre-antibiotic administration levels in antibiotic-exposed animals that received the 4-bacteria consortium or *C. scindens*, but not in those that received vehicle (PBS) (FIG. 15). We confirmed that adoptive transfer of the consortium or *C. scindens* alone restored relative abundance of the secondary bile acids lithochoate (LCA) (FIG. 16a) as well as deoxycholate (DCA) (FIG. 13d), a species previously shown to inhibit *C. difficile* in vitro[44], and both of which inhibit *C. difficile* in a dose-dependent fashion (FIG. 16g,h) Notably, this increased synthesis of secondary bile acids does not significantly reduce primary substrates, such as ursodeoxycholate (UDCA) (FIG. 16b), a species associated with host health benefits[50], or significantly alter the abundance of primary bile acids taurocholic acid (TCA), cholic acid (CA), chenodeoxycholic acid (CDCA), and tauro-chenodeoxycholic acid (TCDCA) (FIG. 16c,d,e,f).

Figure 13G:
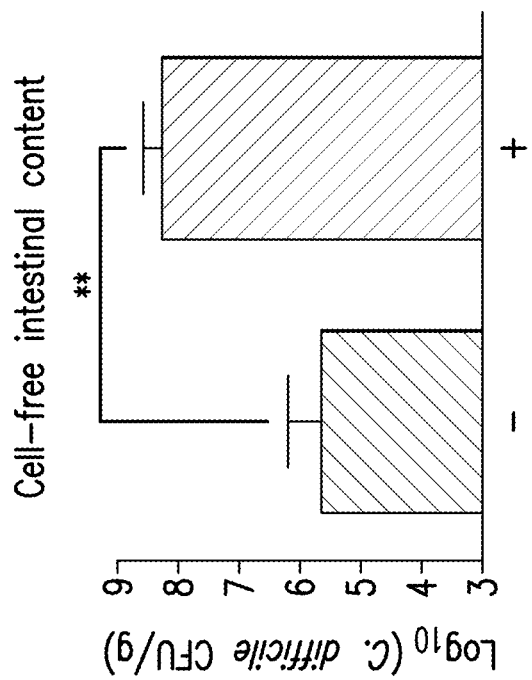

We also evaluated the bile acid-dependence of *C. scindens*-mediated *C. difficile* inhibition using a murine ex vivo model of adoptive transfer and infection. Pre-incubation of intestinal content from antibiotic-naive animals with cholestyramine, a bile acid sequestrant, permitted *C. difficile* growth (FIG. 13g,h). Recapitulating in vivo findings, adoptive transfer of *C. scindens* significantly inhibited *C. difficile* in the intestinal content from antibiotic-exposed mice. Critically, this effect was neutralized when intestinal content was pre-incubated with the bile acid-sequestrant cholestyramine (FIG. 13f), indicating that *C. scindens*-mediated inhibition of *C. difficile* is dependent upon accessing and modifying bile salts endogenous to the intestinal metabolome.

6.6 Conclusions

Taken together, we offer evidence that a small fraction of the murine and human intestinal microbiota, as precise as a single bacterial species, confers resistance against *C. difficile* through its relatively rare capacity to synthesize *C. difficile*-inhibiting metabolites from host-derived bile salts. The conservation of this finding across host species is underscored by our use of a human intestinal microbiota-derived *C. scindens* isolate to augment *C. difficile* inhibition in murine in vivo and ex vivo systems, and emphasizes the therapeutic and diagnostic potential of these findings. Surveys of the intestinal microbiota indicate that the high activity bile acid 7-dehydroxylating bacteria are among of a group of cluster XIVa Clostridia closely related to one another[47,51,52] and the OTUs identified in this study, suggesting that either the genes or the organisms themselves may serve as specific, functionally meaningful biomarkers in individuals at risk for *C. difficile* infection. Additionally, this suggests that other bacteria with 16S homology to *C. scindens* and OTUs identified in this study, many of which have been shown or predicted to possess genes critical for secondary bile acid synthesis[51], may also similarly contribute to *C. difficile* inhibition. The phylogenetic similarity of these Clostridia can present challenges when assigning taxonomy[53-56], highlighting the importance of integrating functional genomic (e.g. secondary bile acid synthesis genes) and metabolomic (e.g. secondary bile acid species) interrogation with 16S rRNA profiling when screening and validating intestinal microbes of interest, as we have done in this study.

Intriguingly, recent metabolomic studies indicate that a broad range of intestinal metabolites are altered during antibiotic treatment[57,58] and that FMT can restore secondary bile acids to physiological levels concurrent with resolution of recurrent *C. difficile* infection in afflicted patients 58, suggesting that replenishment of secondary bile acids and/or the bacteria that synthesize them (such as *C. scindens*) contributes to the therapeutic efficacy of FMT. Inadvertent modulation of the intestinal bile acid pool may also contribute to the observed benefits[59] of anion exchange resins (ex. cholestyramine) as adjunctive therapy for recurrent *C. difficile* infection, as such resins can sequester primary bile acids that promote *C. difficile* spore germination[60]. However, some strains of *C. difficile* are not dependent upon bile salts for germination[61], and germination inhibitors[62] are not effective across all strains either[61]. Thus, broadly sequestering the bile pool would theoretically reduce germinants for some *C. difficile* strains, but would also neutralize secondary bile acids, sometimes disproportionately[63], effectively disinhibiting vegetative *C. difficile* growth. Since *C. scindens* consumes primary bile salts as substrate (e.g. decreasing *C. difficile* spore germinants) in the synthesis of secondary bile acids (e.g. increasing vegetative *C. difficile* inhibitors), remodeling bile species proportions in this fashion may exploit the therapeutic potential of bile modulation better than broad neutralization using sequestrants.

Direct manipulation of intestinal bile acids may be effective for treatment and prevention of *C. difficile* infection, but caution is warranted since some bile species, including secondary bile acids, have been implicated in the promotion of cholesterol gallstone disease and gastrointestinal cancers[64]. Other bile species, such as UDCA, may ameliorate or protect against such diseases[50], and remain at physiological levels in antibiotic-exposed animals reconstituted with *C. scindens* in our study. In these regards, such potent microbiome-mediated chemistry may be therapeutically optimal when driven by the bacteria of origin; other aspects of *C. scindens* physiology and ecology may be critical to ensure secondary bile acid is synthesized, targeted, and otherwise regulated to ensure effective pathogen colonization resistance while avoiding pathological imbalances. Knowledge of these mechanisms, coupled with an appreciation for the ecological context of those microbes responsible, will facilitate amplification of natural microbiota-mediated pathogen resistance in individuals at risk for *C. difficile* infection.

REFERENCES

1. Turnbaugh, P. J., Hamady, M., Yatsunenko, T., Cantarel, B. L., et al. A core gut microbiome in obese and lean twins. Nature 457, 480-484 (2009).
2. Koeth, R. A., Wang, Z., Levison, B. S., Buffa, J. A., et al. Intestinal microbiota metabolism of l-carnitine, a nutrient in red meat, promotes atherosclerosis. Nat Med (2013).
3. Rakoff-Nahoum, S., Paglino, J., Eslami-Varzanch, F., Edberg, S. & Medzhitov, R. Recognition of commensal microflora by toll-like receptors is required for intestinal homeostasis. Cell 118, 229-241 (2004).
4. Ivanov, I. I., Atarashi, K., Manel, N., Brodie, E. L., et al. Induction of intestinal Th17 cells by segmented filamentous bacteria. Cell 139, 485-498 (2009).
5. Chung, H., Pamp, S. J., Hill, J. A., Surana, N. K., et al. Gut immune maturation depends on colonization with a host-specific microbiota. Cell 149, 1578-1593 (2012).
6. Diehl, G. E., Longman, R. S., Zhang, J. X., Breart, B., et al. Microbiota restricts trafficking of bacteria to mesenteric lymph nodes by CX(3)CR1(hi) cells. Nature 494, 116-120 (2013).
7. Duan, J., Chung, H., Troy, E. & Kasper, D. L. Microbial colonization drives expansion of IL-1 receptor 1-expressing and IL-17-producing gamma/delta T cells. Cell Host Microbe 7, 140-150 (2010).
8. Farache, J., Koren, I., Milo, I., Gurevich, I., et al. Luminal Bacteria Recruit CD103(+) Dendritic Cells into the Intestinal Epithelium to Sample Bacterial Antigens for Presentation. Immunity 38, 581-595 (2013).
9. Olszak, T., An, D., Zeissig, S., Vera, M. P., et al. Microbial exposure during early life has persistent effects on natural killer T cell function. Science 336, 489-493 (2012).
10. Wingender, G., Stepniak, D., Krebs, P., Lin, L., et al. Intestinal microbes affect phenotypes and functions of invariant natural killer T cells in mice. Gastroenterology 143, 418-428 (2012).
11. Hand, T. W., Dos Santos, L. M., Bouladoux, N., Molloy, M. J., et al. Acute gastrointestinal infection induces long-lived microbiota-specific T cell responses. Science 337, 1553-1556 (2012).
12. Hill, D. A., Siracusa, M. C., Abt, M. C., Kim, B. S., et al. Commensal bacteria-derived signals regulate basophil hematopoiesis and allergic inflammation. Nat Med 18, 538-546 (2012).
13. Lathrop, S. K., Bloom, S. M., Rao, S. M., Nutsch, K., et al. Peripheral education of the immune system by colonic commensal microbiota. Nature 478, 250-254 (2011).
14. Macpherson, A. J. & Uhr, T. Induction of protective IgA by intestinal dendritic cells carrying commensal bacteria. Science 303, 1662-1665 (2004).
15. Basler, M., Ho, B. T. & Mekalanos, J. J. Tit-for-tat: type VI secretion system counterattack during bacterial cell-cell interactions. Cell 152, 884-894 (2013).
16. Basler, M., Pilhofer, M., Henderson, G. P., Jensen, G. J. & Mekalanos, J. J. Type VI secretion requires a dynamic contractile phage tail-like structure. Nature 483, 182-186 (2012).
17. Rea, M. C., Dobson, A., O'Sullivan, O., Crispie, F., et al. Effect of broad- and narrow-spectrum antimicrobials on *Clostridium difficile* and microbial diversity in a model of the distal colon. Proc Natl Acad Sci USA 108 Suppl 1, 4639-4644 (2011).
18. Rea, M. C., Sit, C. S., Clayton, E., O'Connor, P. M., et al. Thuricin CD, a posttranslationally modified bacteriocin with a narrow spectrum of activity against *Clostridium difficile*. Proc Natl Acad Sci USA 107, 9352-9357 (2010).
19. Abt, M. C., Osborne, L. C., Monticelli, L. A., Doering, T. A., et al. Commensal bacteria calibrate the activation threshold of innate antiviral immunity. Immunity 37, 158-170 (2012).
20. Huse, S. M., Dethlefsen, L., Huber, J. A., Mark Welch, D., et al. Exploring microbial diversity and taxonomy using SSU rRNA hypervariable tag sequencing. PLoS Genet 4, e1000255 (2008).
21. Dethlefsen, L. & Relman, D. A. Incomplete recovery and individualized responses of the human distal gut microbiota to repeated antibiotic perturbation. Proc Natl Acad Sci USA 108 Suppl 1, 4554-4561 (2011).
22. Buffie, C. G., Jarchum, I., Equinda, M., Lipuma, L., et al. Profound alterations of intestinal microbiota following a single dose of clindamycin results in sustained susceptibility to *Clostridium difficile*-induced colitis. Infect Immun 80, 62-73 (2012).
23. Brandl, K., Plitas, G., Mihu, C. N., Ubeda, C., et al. Vancomycin-resistant enterococci exploit antibiotic-induced innate immune deficits. Nature 455, 804-807 (2008).
24. Ubeda, C., Taur, Y., Jenq, R. R., Equinda, M. J., et al. Vancomycin-resistant *Enterococcus* domination of intestinal microbiota is enabled by antibiotic treatment in mice and precedes bloodstream invasion in humans. J Clin Invest 120, 4332-4341 (2010).
25. Ferreira, R. B., Gill, N., Willing, B. P., Antunes, L. C., et al. The intestinal microbiota plays a role in *Salmonella*-induced colitis independent of pathogen colonization. PLoS One 6, e20338 (2011).

26. Rupnik, M., Wilcox, M. H. & Gerding, D. N. *Clostridium difficile* infection: new developments in epidemiology and pathogenesis. Nat Rev Microbiol 7, 526-536 (2009).
27. Kyne, L., Hamel, M. B., Polavaram, R. & Kelly, C. P. Health care costs and mortality associated with nosocomial diarrhea due to *Clostridium difficile*. Clin Infect Dis 34, 346-353 (2002).
28. Zilberberg, M. D., Shorr, A. F. & Kollef, M. H. Increase in adult *Clostridium difficile*-related hospitalizations and case-fatality rate, United States, 2000-2005. Emerg Infect Dis 14, 929-931 (2008).
29. Surawicz, C. M. & Alexander, J. Treatment of refractory and recurrent *Clostridium difficile* infection. Nat Rev Gastroenterol Hepatol 8, 330-339 (2011).
30. Marsh, J. W., Arora, R., Schlackman, J. L., Shutt, K. A., et al. Association of relapse of *Clostridium difficile* disease with BI/NAP1/027. J Clin Microbiol 50, 4078-4082 (2012).
31. Bakken, J. S., Borody, T., Brandt, L. 3., Brill, J. V., et al. Treating *Clostridium difficile* infection with fecal microbiota transplantation. Clin Gastroenterol Hepatol 9, 1044-1049 (2011).
32. van Nood, E., Vrieze, A., Nieuwdorp, M., Fuentes, S., et al. Duodenal infusion of donor feces for recurrent *Clostridium difficile*. N Engl J Med 368, 407-415 (2013).
33. Pamer, E. G. Fecal microbiota transplantation: effectiveness, complexities, and lingering concerns. Mucosal Immunol 7, 210-214 (2014).
34. Reeves, A. E., Theriot, C. M., Bergin, I. L., Huffnagle, G. B., et al. The interplay between microbiome dynamics and pathogen dynamics in a murine model of *Clostridium difficile* Infection. Gut Microbes 2, 145-158 (2011).
35. Lawley, T. D., Clare, S., Walker, A. W., Stares, M. D., et al. Targeted restoration of the intestinal microbiota with a simple, defined bacteriotherapy resolves relapsing *Clostridium difficile* disease in mice. PLoS Pathog 8, e1002995 (2012).
36. Petrof, E. O., Gloor, G. B., Vanner, S. J., Weese, S. J., et al. Stool substitute transplant therapy for the eradication of *Clostridium difficile* infection: 'RePOOPulating' the gut. Microbiome 1, 3 (2013).
37. Hamilton, M. J., Weingarden, A. R., Unno, T., Khoruts, A. & Sadowsky, M. J. High-throughput DNA sequence analysis reveals stable engraftment of gut microbiota following transplantation of previously frozen fecal bacteria. Gut Microbes 4, 125-135 (2013).
38. Chang, J. Y., Antonopoulos, D. A., Kalra, A., Tonelli, A., et al. Decreased diversity of the fecal Microbiome in recurrent *Clostridium difficile*-associated diarrhea. J Infect Dis 197, 435-438 (2008).
39. Lozupone, C. & Knight, R. UniFrac: a new phylogenetic method for comparing microbial communities. Appl Environ Microbiol 71, 8228-8235 (2005).
40. Taur, Y., Xavier, J. B., Lipuma, L., Ubeda, C., et al. Intestinal domination and the risk of bacteremia in patients undergoing allogeneic hematopoietic stem cell transplantation. Clin Infect Dis 55, 905-914 (2012).
41. Kinnebrew, M. A., Lee, Y. J., Jenq, R. R., Lipuma, L., et al. Early *Clostridium difficile* Infection during Allogeneic Hematopoietic Stem Cell Transplantation. PLoS One 9, e90158 (2014).
42. Stein, R. R., Bucci, V., Toussaint, N. C., Buffie, C. G., et al. Ecological modeling from time-series inference: insight into dynamics and stability of intestinal microbiota. PLoS Comput Biol 9, e1003388 (2013).
43. Chen, X., Katchar, K., Goldsmith, J. D., Nanthakurnar, N., et al. A mouse model of *Clostridium difficile*-associated disease. Gastroenterology 135, 1984-1992 (2008).
44. Sorg, J. A. & Sonenshein, A. L. Bile salts and glycine as cogerminants for *Clostridium difficile* spores. J Bacteriol 190, 2505-2512 (2008).
45. de Aguiar Vallim, T. Q., Tarling, E. J. & Edwards, P. A. Pleiotropic roles of bile acids in metabolism. Cell Metab 17, 657-669 (2013).
46. Kang, D. J., Ridlon, J. M., Moore, D. R., Barnes, S. & Hylemon, P. B. *Clostridium scindens* baiCD and baiH genes encode stereo-specific 7alpha/7beta-hydroxy-3-oxo-delta4-cholenoic acid oxidoreductases. Biochim Biophys Acta 1781, 16-25 (2008).
47. Ridlon, J. M., Kang, D. J. & Hylemon, P. B. Bile salt biotransformations by human intestinal bacteria. J Lipid Res 47, 241-259 (2006).
48. Langille, M. G., Zaneveld, J., Caporaso, J. G., McDonald, D., et al. Predictive functional profiling of microbial communities using 16S rRNA marker gene sequences. Nat Biotechnol 31, 814-821 (2013).
49. Wells, J. E., Williams, K. B., Whitehead, T. R., Heuman, D. M. & Hylemon, P. B. Development and application of a polymerase chain reaction assay for the detection and enumeration of bile acid 7α-dehydroxylating bacteria in human feces. Clinica Chimica Acta 331, 127-134 (2003).
50. Barrasa, J. I., Olmo, N., Lizarbe, M. A. & Turnay, J. Bile acids in the colon, from healthy to cytotoxic molecules. Toxicol In Vitro 27, 964-977 (2013).
51. Kitahara, M., Takamine, F., Imamura, T. & Benno, Y. Assignment of *Eubacterium* sp. VPI 12708 and related strains with high bile acid 7alpha-dehydroxylating activity to *Clostridium scindens* and proposal of *Clostridium hylemonae* sp. nov., isolated from human faeces. Int J Syst Evol Microbiol 50 Pt 3, 971-978 (2000).
52. Wells, E. & Hylemon, B. Identification and Characterization of a Bile Acid 7alpha-Dehydroxylation Operon in *Clostridium* sp. Strain TO-931, a Highly Active 7alpha-Dehydroxylating Strain Isolated from Human Feces. Applied and Environmental Microbiology 66, 1107-1113 (2000).
53. Collins, M. D., Lawson, P. A., Willems, A., Cordoba, J. J., et al. The phylogeny of the genus *Clostridium*: proposal of five new genera and eleven new species combinations. Int J Syst Bacteriol 44, 812-826 (1994).
54. Liu, C., Finegold, S. M., Song, Y. & Lawson, P. A. Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. Int J Syst Evol Microbiol 58, 1896-1902 (2008).
55. Carlier, J. P., Bedora-Faure, M., K'ouas, G., Alauzet, C. & Mory, F. Proposal to unify *Clostridium orbiscindens* Winter et al. 1991 and *Eubacterium plautii* (Séguin 1928) Hofstad and Aasjord 1982, with description of *Flavonifractor plautii* gen. nov., comb. nov., and reassignment of *Bacteroides capillosus* to *Pseudoflavonifractor capillosus* gen. nov., comb. nov. Int J Syst Evol Microbiol 60, 585-590 (2010).
56. Yutin, N. & Galperin, M. Y. A genomic update on clostridial phylogeny: Gram-negative spore formers and other misplaced clostridia. Environ Microbiol 15, 2631-2641 (2013).

57. Theriot, C. M., Koenigsknecht, M. J., Carlson, P. E., Hatton, G. E., et al. Antibiotic-induced shifts in the mouse gut microbiome and metabolome increase susceptibility to *Clostridium difficile* infection. Nature Communications 5, (2014).
58. Weingarden, A. R., Chen, C., Bobr, A., Yao, D., et al. Microbiota transplantation restores normal fecal bile acid composition in recurrent *Clostridium difficile* infection. Am J Physiol Gastrointest Liver Physiol 306, G310-G319 (2014).
59. Louie, T. J., Peppe, J., Watt, C. K., Johnson, D., et al. Tolevamer, a novel nonantibiotic polymer, compared with vancomycin in the treatment of mild to moderately severe *Clostridium difficile*-associated diarrhea. Clin Infect Dis 43, 411-420 (2006).
60. Giel, J. L., Sorg, J. A., Sonenshein, A. L. & Zhu, J. Metabolism of bile salts in mice influences spore germination in *Clostridium difficile*. PLoS One 5, e8740 (2010).
61. Heeg, D., Burns, D. A., Cartman, S. T. & Minton, N. P. Spores of *Clostridium difficile* clinical isolates display a diverse germination response to bile salts. PLoS One 7, e32381 (2012).
62. Sorg, J. A. & Sonenshein, A. L. Chenodeoxycholate is an inhibitor of *Clostridium difficile* spore germination. J Bacteriol 191, 1115-1117 (2009).
63. Out, C., Groen, A. K. & Brufau, G. Bile acid sequestrants: more than simple resins. Curr Opin Lipidol 23, 43-55 (2012).
64. Bernstein, H., Bernstein, C., Payne, C. M., Dvorakova, K. & Garewal, H. Bile acids as carcinogens in human gastrointestinal cancers. Mutat Res 589, 47-65 (2005).
65. Edgar, R. C., Haas, B. J., Clemente, J. C., Quince, C. & Knight, R. UCHIME improves sensitivity and speed of chimera detection. Bioinformatics 27, 2194-2200 (2011).
66. Schloss, P. D., Westcott, S. L., Ryabin, T., Hall, J. R., et al. Introducing mothur: open-source, platform-independent, community-supported software for describing and comparing microbial communities. Appl Environ Microbiol 75, 7537-7541 (2009).
67. Human Microbiome Project Consortium Structure, function and diversity of the healthy human microbiome. Nature 486, 207-214 (2012).
68. Caporaso, J. G., Lauber, C. L., Walters, W. A., Berg-Lyons, D., et al. Ultra-high-throughput microbial community analysis on the Illumina HiSeq and MiSeq platforms. ISME J 6, 1621-1624 (2012).
69. Ubeda, C., Bucci, V., Caballero, S., Djukovic, A., et al. Intestinal microbiota containing *Barnesiella* cures vancomycin-resistant *Enterococcus faecium* colonization. Infect Immun 81, 965-973 (2013).
70. Sheneman, L., Evans, J. & Foster, J. A. Clearcut: a fast implementation of relaxed neighbor joining. Bioinformatics 22, 2823-2824 (2006).
71. J G Caporaso, J Kuczynski, J Stombaugh, K Bittinger, F D Bushman, E K Costello, N Fierer, A G Peia, J K Goodrich, J I Gordon, G A Huttlcy, S T Kelley, D Knights, J E Koenig, R E Ley, C A Lozupone, D McDonald, B D Muegge, M Pirrung, J Reeder, J R Sevinsky, P J Turnbaugh, W A Walters, J Widmann, T Yatsunenko, J Zaneveld, R Knight, QIIME allows analysis of high-throughput community sequencing data., Nat Methods. 2010 May; 7(5):335-6.
72. Hall, B. G. Building phylogenetic trees from molecular data with MEGA. Mol Biol Evol 30, 1229-1235 (2013).
73. Zhao, Y., Tang, H. & Ye, Y. RAPSearch2: a fast and memory-efficient protein similarity search tool for next-generation sequencing data. Bioinformatics 28, 125-126 (2012).
74. Cohen, J. Statistical power analysis for the behavioral sciences (Routledge, Hillsdale, N J, 1988).
75. Stein, R. R., Bucci, V., Toussaint, N. C., Buffie, C. G., et al. Ecological modeling from time-series inference: insight into dynamics and stability of intestinal microbiota. PLoS Comput Biol 9, e1003388 (2013).
76. Bartlett J G, Chang T W, Gurwith M et al., 1978. Antibiotic-associated pseudomembranous colitis due to toxin-producing clostridia. N. Engl. J. Med. 298:531-534.
77 Buffie and Pamer, 2013. Microbiota-mediated colonization resistance against intestinal pathogens. Nature Reviews Immunology 13:790-801.
78. Chen X and Lamont J T, 2013. Overview of *Clostridium difficile* infection: implications for China. Gastroenterology Report 1:153-158.
79. Ridlon J M et al., 2013. *Clostridium scindens*: a human gut microbe with a high potential to convert glucocorticoids into androgens. J. Lipid Res. 54:2437-2449.
80. Ridlon J M and Hylemon P B, 2012. Identification and characterization of two bile-acid coenzyme A transferases from *Clostridium scindens*, a bile acid 7α-dehydroxylating intestinal bacterium. J. Lipid Res. 53:66-76.
81. Ridlon J M et al., 2006. Bile salt biotransformations by Human Intestinal bacteria. J. Lipid Res. 47:241-259.
82. Zar F A, Bakkanagari S R et al., 2007. A comparison of vancomycin and metronidazole for the treatment of *Clostridium difficile*-associated diarrhea, stratified by disease severity. Clin. Infect. Dis. 45:302-307.

Various references and sequence accession numbers are cited herein, the contents of which are hereby incorporated by reference in their entireties.

We claim:

1. A method for reducing the risk of *Clostridium difficile* infection or reducing the severity of *Clostridium difficile* infection in a subject in need thereof, comprising administering to the subject a therapeutically effective amount of a composition, which comprises at least one isolated bacteria or spores thereof, which is selected from Clostridiales VE202-05, Clostridiales VE202-26, or both.

2. The method of claim 1, wherein the composition further comprises one or more additional isolated bacteria or spores thereof, which is selected from *Clostridium scindens, Clostridium hiranonis, Clostridium hylemonae, Clostridium perfringens, Clostridium sordelli, Proteocatella sphenisci,* Lachnospiraceae 5_1_57FAA, *Barnesiella intestihominis, Blautia hansenii, Pseudoflavonifractor capillosus,* or combinations thereof.

3. The method of claim 1, wherein one or more of the isolated bacteria or spores thereof of the composition are capable of engrafting in the gastrointestinal tract of the subject.

4. The method of claim 1, wherein administering the composition increases the amount of a secondary bile acid in the gastrointestinal tract of the subject.

5. The method of claim 1, further comprising administering to the subject an antibiotic, an immunotherapeutic agent, an herbal remedy, a probiotic, or combinations thereof.

6. The method of claim 5, wherein the antibiotic comprises a vancomycin, a metronidazole, a fidaxomicin, or combinations thereof.

7. The method of claim 5, wherein the antibiotic is not selected from the group consisting of a β-lactam antibiotic, a clindamycin, a cephalosporin, a quinolone antibiotic, a levofloxacin, a fluoroquinolone, a macrolide antibiotic, a trimethoprim, a sulfonamide antibiotic, and combinations thereof.

8. The method of claim 1, wherein the subject is receiving an antibiotic therapy.

9. The method of claim 2, wherein the additional isolated bacteria or spores thereof is *Clostridium scindens*.

10. The method of claim 2, wherein the additional isolated bacteria or spores thereof is *Pseudoflavonifractor capillosus*.

11. The method of claim 1, wherein the composition is administered to the subject via oral or rectal administration.

12. The method of claim 1, wherein one or more of the isolated bacteria or spores thereof of the composition are lyophilized.

13. The method of claim 1, wherein the subject has previously suffered a *Clostridium difficile* infection.

14. A method for reducing the risk of developing *Clostridium difficile*-associated disease or treating a *Clostridium difficile*-associated disease in a subject in need thereof, comprising administering to the subject a therapeutically effective amount of a composition, which comprises at least one isolated bacteria or spores thereof, which is selected from Clostridiales VE202-05, Clostridiales VE202-26, or both.

15. The method of claim 14, wherein the composition further comprises one or more additional isolated bacteria or spores thereof, which is selected from *Clostridium scindens, Clostridium hiranonis, Clostridium hylemonae, Clostridium perfringens, Clostridium sordelli, Proteocatella sphenisci,* Lachnospiraceae 5_1_57FAA, *Barnesiella intestihominis, Blautia hansenii, Pseudoflavonifractor capillosus,* or combinations thereof.

16. The method of claim 14, wherein the *Clostridium difficile*-associated disease comprises a *Clostridium difficile* colitis, a pseudomembranous colitis, or both.

* * * * *